(12) United States Patent  (10) Patent No.: US 8,513,462 B2
Nugent et al.  (45) Date of Patent: Aug. 20, 2013

(54) PESTICIDES AND USES THEREOF

(75) Inventors: Benjamin M. Nugent, Brownsburg, IN (US); Ann M. Buysse, Carmel, IN (US); Jonathan M. Babcock, Carmel, IN (US); Matthias S. Ober, Midland, MI (US); Timothy P. Martin, Noblesville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 13/607,843

(22) Filed: Sep. 10, 2012

(65) Prior Publication Data

US 2013/0012385 A1 Jan. 10, 2013

Related U.S. Application Data

(62) Division of application No. 12/171,323, filed on Jul. 11, 2008, now Pat. No. 8,288,589.

(60) Provisional application No. 60/962,217, filed on Jul. 27, 2007.

(51) Int. Cl.
*C07C 313/00* (2006.01)

(52) U.S. Cl.
USPC ......... 564/102; 548/243; 546/281.4; 546/330

(58) Field of Classification Search
None
See application file for complete search history.

(56) References Cited

U.S. PATENT DOCUMENTS

| | | | |
|---|---|---|---|
| 8,288,589 B2 * | 10/2012 | Nugent et al. ............... 564/102 |
| 2005/0228027 A1 | 10/2005 | Zhu et al. |
| 2007/0203191 A1 | 8/2007 | Loso et al. |
| 2008/0058390 A1 | 3/2008 | Loso et al. |
| 2008/0058394 A1 | 3/2008 | Loso et al. |
| 2008/0108665 A1 | 5/2008 | Huang et al. |
| 2008/0108666 A1 | 5/2008 | Loso et al. |
| 2008/0108667 A1 | 5/2008 | Zhu et al. |

FOREIGN PATENT DOCUMENTS

| | | |
|---|---|---|
| WO | WO-2006/037945 | 4/2006 |
| WO | PCT/US2008/069722 | 5/2009 |

* cited by examiner

*Primary Examiner* — Sudhakar Katakam
(74) *Attorney, Agent, or Firm* — Carl D. Corvin

(57) ABSTRACT

The invention disclosed in this document is related to field of pesticides and their use in controlling pests. In particular compounds having the following formula are disclosed.

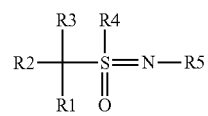

7 Claims, No Drawings

PESTICIDES AND USES THEREOF

CROSS-REFERENCE TO RELATED APPLICATION

This application claims priority from U.S. provisional application 60/962,217 filed Jul. 27, 2007 the entire disclosure of which is hereby incorporated by reference. This application also claims priority from U.S. patent application Ser. No. 12/171,323 filed Jul. 11, 2008 the entire disclosure of which is hereby incorporated by reference.

FIELD OF THE INVENTION

The invention disclosed in this document is related to field of pesticides and their use in controlling pests.

BACKGROUND OF THE INVENTION

Pests cause millions of human deaths around the world each year. Furthermore, there are more than ten thousand species of pests that cause losses in agriculture. These agricultural losses amount to billions of U.S. dollars each year. Termites cause damage to various structures such as homes. These termite damage losses amount to billions of U.S. dollars each year. As final note, many stored food pests eat and adulterate stored food. These stored food losses amount to billions of U.S. dollars each year, but more importantly, deprive people of needed food.

There is an acute need for new pesticides. Insects are developing resistance to pesticides in current use. Hundreds of insect species are resistant to one or more pesticides. The development of resistance to some of the older pesticides, such as DDT, the carbamates, and the organophosphates, is well known. But resistance has even developed to some of the newer pesticides. Therefore, a need exists for new pesticides and particularly for pesticides that have new modes of action.

Substituents (Non-Exhaustive List)

The examples given for the substituents are (except for halo) non-exhaustive and must not be construed as limiting the invention disclosed in this document.

"alkenyl" means an acyclic, unsaturated (at least one carbon-carbon double bond), branched or unbranched, substituent consisting of carbon and hydrogen, for example, vinyl, allyl, butenyl, pentenyl, hexenyl, heptenyl, octenyl, nonenyl, and decenyl.

"alkenyloxy" means an alkenyl further consisting of a carbon-oxygen single bond, for example, allyloxy, butenyloxy, pentenyloxy, hexenyloxy, heptenyloxy, octenyloxy, nonenyloxy, and decenyloxy.

"alkoxy" means an alkyl further consisting of a carbon-oxygen single bond, for example, methoxy, ethoxy, propoxy, isopropoxy, 1-butoxy, 2-butoxy, isobutoxy, tert-butoxy, pentoxy, 2-methylbutoxy, 1,1-dimethylpropoxy, hexoxy, heptoxy, octoxy, nonoxy, and decoxy.

"alkyl" means an acyclic, saturated, branched or unbranched, substituent consisting of carbon and hydrogen, for example, methyl, ethyl, propyl, isopropyl, 1-butyl, 2-butyl, isobutyl, tert-butyl, pentyl, 2-methylbutyl, 1,1-dimethylpropyl, hexyl, heptyl, octyl, nonyl, and decyl.

"alkynyl" means an acyclic, unsaturated (at least one carbon-carbon triple bond, and any double bonds), branched or unbranched, substituent consisting of carbon and hydrogen, for example, ethynyl, propargyl, butynyl, pentynyl, hexynyl, heptynyl, octynyl, nonynyl, and decynyl.

"alkynyloxy" means an alkynyl further consisting of a carbon-oxygen single bond, for example, pentynyloxy, hexynyloxy, heptynyloxy, octynyloxy, nonynyloxy, and decynyloxy.

"aryl" means a cyclic, aromatic substituent consisting of hydrogen and carbon, for example, phenyl, naphthyl, and biphenylyl.

"cycloalkenyl" means a monocyclic or polycyclic, unsaturated (at least one carbon-carbon double bond) substituent consisting of carbon and hydrogen, for example, cyclobutenyl, cyclopentenyl, cyclohexenyl, cycloheptenyl, cyclooctenyl, cyclodecenyl, norbornenyl, bicyclo[2.2.2]octenyl, tetrahydronaphthyl, hexahydronaphthyl, and octahydronaphthyl.

"cycloalkenyloxy" means a cycloalkenyl further consisting of a carbon-oxygen single bond, for example, cyclobutenyloxy, cyclopentenyloxy, cyclohexenyloxy, cycloheptenyloxy, cyclooctenyloxy, cyclodecenyloxy, norbornenyloxy, and bicyclo[2.2.2]octenyloxy.

"cycloalkyl" means a monocyclic or polycyclic, saturated substituent consisting of carbon and hydrogen, for example, cyclopropyl, cyclobutyl, cyclopentyl, cyclohexyl, cycloheptyl, cyclooctyl, cyclodecyl, norbornyl, bicyclo[2.2.2]octyl, and decahydronaphthyl.

"cycloalkoxy" means a cycloalkyl further consisting of a carbon-oxygen single bond, for example, cyclopropyloxy, cyclobutyloxy, cyclopentyloxy, cyclohexyloxy, cycloheptyloxy, cyclooctyloxy, cyclodecyloxy, norbornyloxy, and bicyclo[2.2.2]octyloxy.

"halo" means fluoro, chloro, bromo, and iodo.

"haloalkyl" means an alkyl further consisting of, from one to the maximum possible number of, identical or different, halos, for example, fluoromethyl, difluoromethyl, trifluoromethyl, 1-fluoromethyl, 2-fluoroethyl, 2,2,2-trifluoroethyl, chloromethyl, trichloromethyl, and 1,1,2,2-tetrafluoroethyl.

"heterocyclyl" means a cyclic substituent that may be fully saturated, partially unsaturated, or fully unsaturated, where the cyclic structure contains at least one carbon and at least one heteroatom, where said heteroatom is nitrogen, sulfur, or oxygen, for example, benzofuranyl, benzoisothiazolyl, benzoisoxazolyl, benzoxazolyl, benzoxolyl, benzothienyl, benzothiazolyl cinnolinyl, furanyl, indazolyl, indolyl, imidazolyl, isoindolyl, isoquinolinyl, isothiazolyl, isoxazolyl, 1,3,4 oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, 1,2,3,4-tetrazolyl, thiazolinyl, thiazolobenzoxadiazolyl, thiazolyl, thienyl, 1,2,3-triazinyl, 1,2,4-triazinyl, 1,3,5-triazinyl, 1,2,3-triazolyl, and 1,2,4-triazolyl.

DETAILED DESCRIPTION OF THE INVENTION

The general formula for the compounds in this invention follows

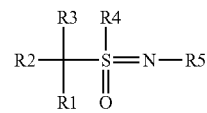

wherein

R1 is an unsubstituted heterocyclyl or a substituted heterocyclyl, wherein the substituted heterocyclyl has one or more substituents independently selected from alkenyl, alkenyloxy, alkoxy, alkyl, alkynyl, alkynyloxy, aryl, cycloalkenyl, cycloalkenyloxy, cycloalkyl, cycloalkoxy, halo, haloalkyl, and heterocyclyl;

R2 is H, alkenyl, alkenyloxy, alkoxy, alkyl, alkynyl, alkynyloxy, aryl, cycloalkenyl, cycloalkenyloxy, cycloalkyl, cycloalkoxy, halo, haloalkyl, or heterocyclyl;

R3 is H, alkenyl, alkenyloxy, alkoxy, alkyl, alkynyl, alkynyloxy, aryl, cycloalkenyl, cycloalkenyloxy, cycloalkyl, cycloalkoxy, halo, haloalkyl, or heterocyclyl;

R2 and R3 may form a ring wherein the ring contains 3 or more ring atoms optionally containing an O or N atom;

R2 and R4 may form a ring wherein the ring contains 3 or more ring atoms optionally containing an O or N atom;

R4 is H, alkenyl, alkenyloxy, alkoxy, alkyl, alkynyl, alkynyloxy, aryl, cycloalkenyl, cycloalkenyloxy, cycloalkyl, cycloalkoxy, halo, haloalkyl, or heterocyclyl; and R5 is an unsubstituted heterocyclyl or a substituted heterocyclyl, wherein the substituted heterocyclyl has one or more substituents independently selected from alkenyl, alkenyloxy, alkoxy, alkyl, alkynyl, alkynyloxy, aryl, cycloalkenyl, cycloalkenyloxy, cycloalkyl, cycloalkoxy, halo, haloalkyl, heterocyclyl, —O⁻ (such as,

CN, C1-C6 alkyl-O—C(=O)—, C1-C6 alkyl-O—C1-C6 alkyl, C1-C6 alkylthio-C1-C6 alkyl, and NO2, optionally, the substituents (that can be further substituted) on a substituted heterocyclyl are also substituted with one or more substituents independently selected from alkenyl, alkenyloxy, alkoxy, alkyl, alkynyl, alkynyloxy, aryl, cycloalkenyl, cycloalkenyloxy, cycloalkyl, cycloalkoxy, halo, haloalkyl, heterocyclyl, CN, C1-C6 alkyl-O—C(=O)—, and NO2.

In one embodiment of the compounds herein R1 is a substituted pyridyl.

In another embodiment R1 is a substituted pyridyl, which is substituted with one or more halogens.

In another embodiment R1 is a substituted pyridyl, which is substituted with one or more C1-C6 haloalkyls.

In another embodiment R2 is a C1-C6 alkyl.

In another embodiment R2 is a H.

In another embodiment R2 and R4 form a C3-C6 alkyl bridge.

In another embodiment R3 is H.

In another embodiment R4 is a C1-C6 alkyl.

In another embodiment R5 is a (mono or multi)substituted, or unsubstituted, benzothiazolyl, oxazolyl, pyridyl, pyrimidinyl, thiadiazolyl, thiazolyl, thiazolobenzoxadiazolyl, and thienyl, wherein the substituents are independently selected from halo, NO2, C1-C6 alkyl, C1-C6 haloalkyl, aryl, benzyl, CN, C1-C6 alkyl-O—C(=O)—, C1-C6 alkoxy, —O⁻, substituted aryl, C1-C6 alkyl —O—C1-C6 alkyl, C1-C6 cycloalkyl, substituted heterocyclyl, heterocyclyl, and C1-C6 alkylthio-C1-C6 alkyl.

In another embodiment of this invention,
R1 is

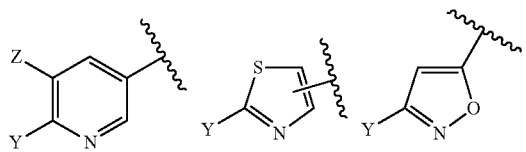

wherein Y is alkenyl, alkenyloxy, alkoxy, alkyl, alkynyl, alkynyloxy, aryl, cycloalkenyl, cycloalkenyloxy, cycloalkyl, cycloalkoxy, halo, haloalkyl, and heterocycyclyl and Z is H, halo, azido, alkyl, alkoxy, haloalkyl, haloalkoxy, aryl, or heterocyclyl, R2 is H, alkyl, halo, or haloalkyl;

R3 is H, alkyl, halo, or haloalkyl;

R2 and R3 may form a ring wherein the ring contains 3 or more ring atoms optionally containing an O or N atom;

R4 is H, alkyl, halo, or haloalkyl; and

R5 is an unsubstituted heterocyclyl or a substituted heterocyclyl, wherein the substituted heterocyclyl has one or more substituents selected independently from alkenyl, alkenyloxy, alkoxy, alkyl, alkynyl, alkynyloxy, aryl, cycloalkenyl, cycloalkenyloxy, cycloalkyl, cycloalkoxy, halo, haloalkyl, and heterocyclyl.

In another embodiment of this invention,
R1 is

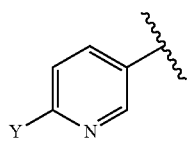

wherein Y is halo or C1-C4 haloalkyl;

R2 is H, alkyl, halo, or haloalkyl;

R3 is H, alkyl, halo, or haloalkyl;

R4 is C1-C4 alkyl; and

R5 is

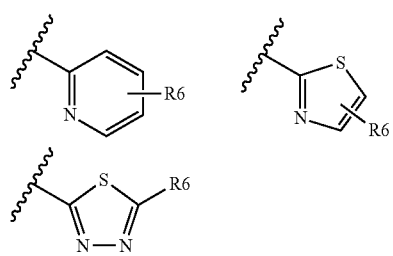

with one or more R6 where R6 is H, halo, haloalkyl, or nitro.

In the above embodiments the number of carbon atoms can varied a great deal, for example, C1-C20, C1-C10, C1-C6, C1-C3, C2-C20, C2-C10, C2-C6, C3-C6, C3-C8, and each number within these ranges.

These compounds can be made by any method known in the art, and examples thereof are presented below.

EXAMPLES

The examples are for illustration purposes and are not to be construed as limiting the invention disclosed in this document to only the embodiments disclosed in these examples.

Example I

Preparation of 3-[1-ethyl(N-(2-(5-fluoro)pyridine)-sulfoximinyl)(methyl)]-6-trifluoromethylpyridine (1)

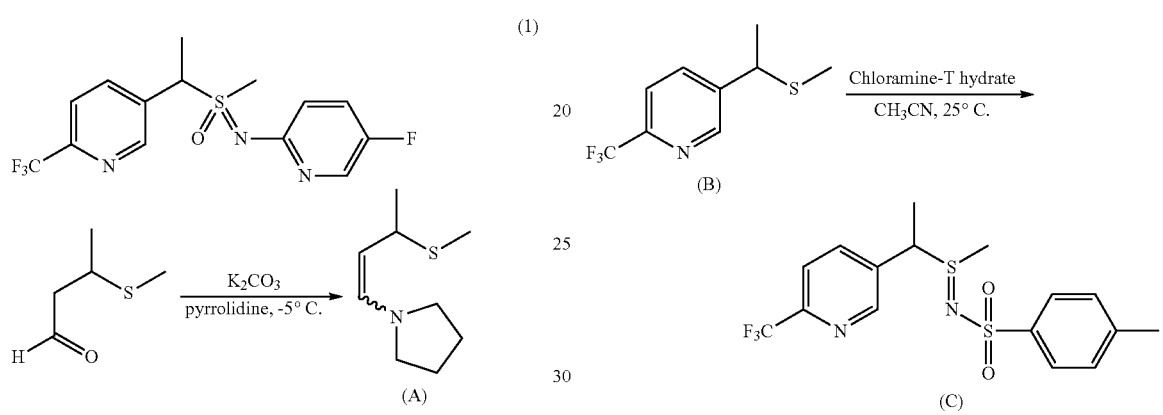

To a magnetically stirred suspension of 6.9 g (0.05 mol) of anhydrous potassium carbonate in 20 ml of freshly distilled pyrrolidine under nitrogen at −5° C. was added dropwise 11.8 g (0.01 mol) of 3-thiomethylbutyraldehyde over 10 min. The reaction mixture was warmed to room temperature over 3 hr. and was filtered through a sintered glass funnel washing the residue thoroughly with 150 ml of anhydrous ether. After removing the solvent on the rotary evaporator, Kugelrohr distillation at 90-95° C./1 mm gave 1-pyrrolidyl-3-thiomethyl-1-butene (A) as a near colorless liquid in a 96% yield.

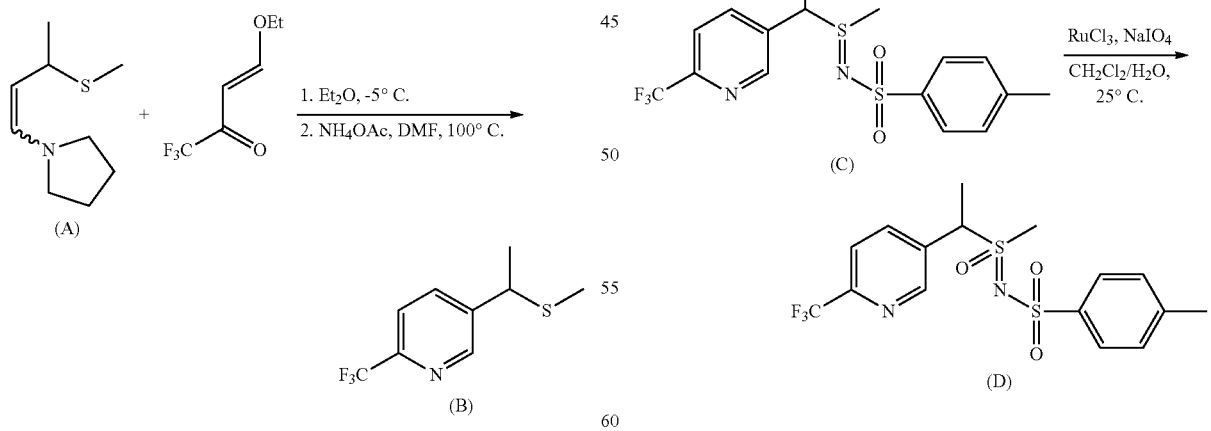

To a magnetically stirred solution of 1.68 g (0.01 mol) of (E)-4-ethoxy-1,1,1-trifluoro-but-3-en-2-one (EFTBO) in 10 ml of anhydrous ether at −5° C. under nitrogen was added dropwise a solution of 1.71 g (0.01 mol) of 1-pyrrolidyl-3-thiomethyl-1-butene (A) in 2 ml of ether over 2 min. The reaction was warmed to room temperature over 3 hr and turned yellow. After removing the solvent on the rotary evaporator, 10 ml of dimethylformamide (DMF) and 1.54 g (0.02 mol) of ammonium acetate were added. The reaction mixture was heated to 100° C. for 2 hr, allowed to cool to room temperature, and added to 100 ml ether and 25 ml of sat. NaCl. The organic layer was washed with 3×25 ml of sat NaCl, dried (MgSO$_4$), and solvent removed to give 1.75 g of an orange oil. Column chromatography, eluting with 5% EtOAc/hexane, furnished 2-trifluoromethyl-5-(1-methylthio)ethylpyridine (B) in 41.4% yield. $^1$H NMR 1.62 (d, 3H, J=7), 1.94 (s, 3H), 3.93 (q, 1H, J=7), 7.67 (d, 1H, J=8.2), 7.89 (dd, 1H, J=8.2, 1.8), 8.66 (d, 1H, J=1.8). Calc'd for C$_9$H$_{10}$F$_3$NS: C, 48.86; H, 4.56; N, 6.33: S, 14.49. Found: C, 49.43; H, 4.69; N, 5.97: S, 15.47.

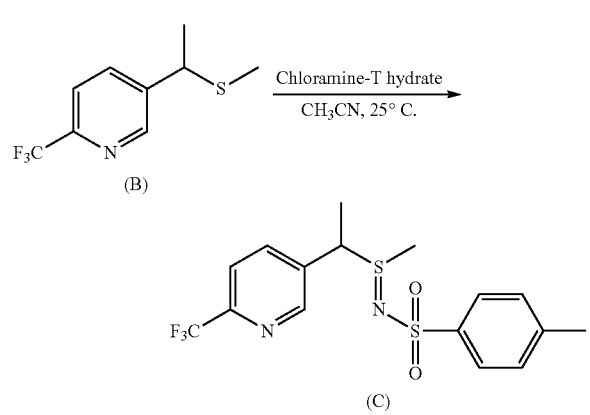

To a solution of 2-trifluoromethyl-5-(1-methylthio)ethylpyridine (B) (10 g, 45 mmol) in acetonitrile (350 mL) was added chloramine-T (13.4 g, 47 mmol). The mixture was stirred overnight, then ethyl acetate (200 mL) was added. The crude reaction mixture was then passed through a silica gel plug (acetone eluent) and concentrated to furnish sulfilimine (C) as a white, fluffy solid in 40% yield. LC-MS (ESI): Mass calcd for C$_{16}$H$_{17}$F$_3$N$_2$O$_2$S$_2$ [M]$^+$, 390. Found 390.

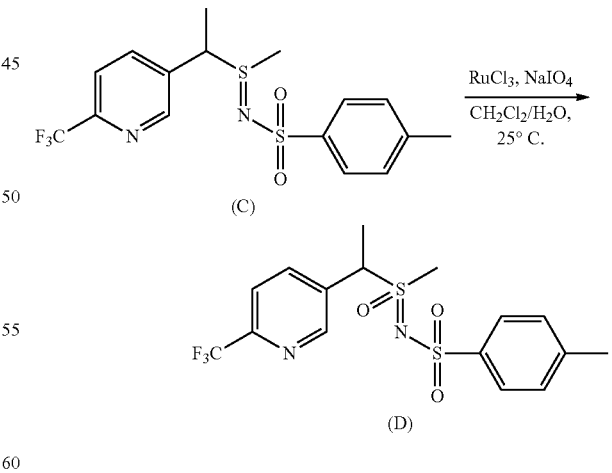

To a solution of NaIO$_4$ (2.2 g, 10 mmol) in H$_2$O (18 mL) at 25° C. was added CH$_2$Cl$_2$ (18 mL) followed by RuCl$_3$ (29 mg, 0.13 mmol). To the dark brown mixture was then added a solution of sulfilimine (C) (2.0 g, 5.1 mmol) in CH$_2$Cl$_2$ (16 mL). The mixture was stirred for 3 h, then the stirring was stopped and the reaction mixture was allowed stand until the layers were defined. The organic layer was removed and filtered through a frit filled with sand, alumina, and celite (acetone eluent). The filtrate was concentrated to furnish the sulfoximine (D) as a white solid in 40% yield. LC-MS (ESI): Mass calcd for $C_{16}H_{18}F_3N_2O_3S_2$ [M+H]$^+$, 407. Found 407.

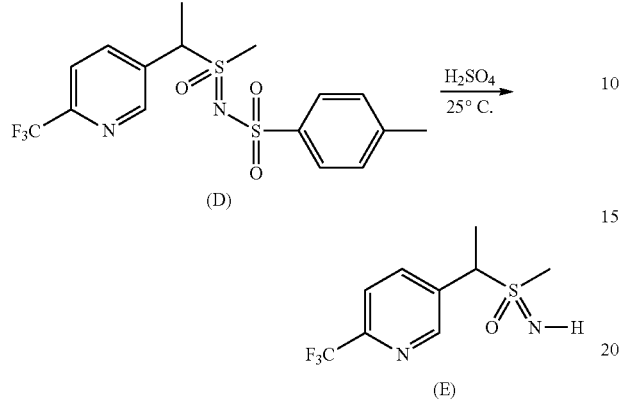

Sulfoximine (D) (1.0 g, 2.5 mmol) was dissolved in conc. $H_2SO_4$ (15 mL) and stirred for 6 h. The crude reaction mixture was then poured into a flask with ice and solid NaHCO$_3$ was added slowly until the aqueous layer was neutral. The aqueous layer was extracted with CH$_2$Cl$_2$ and the combined organic extracts were dried over MgSO$_4$ and concentrated to furnish 5-[1-(methylsulfonimidoyl)ethyl]-2-trifluoromethylpyridine (E) as a white solid in 84% yield. LC-MS (ESI): Mass calcd for $C_9H_{11}F_3N_2OS$ [M]$^+$, 252. Found 252.

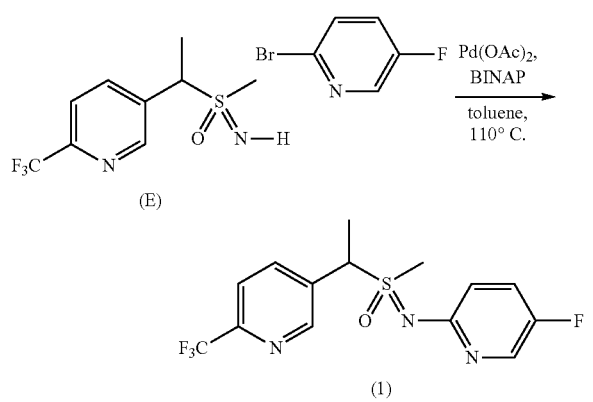

To a mixture of palladium(II) acetate (7 mg, 0.03 mmol) and rac-2,2'-bis(diphenylphosphino)-1,1'binaphthyl (30 mg, 0.05 mmol) in toluene (3 mL) was added 2-bromo-5-fluoropyridine (119 mg, 0.67 mmol), 5-[1-(methylsulfonimidoyl)ethyl]-2-trifluoromethylpyridine (E) (200 mg, 0.8 mmol) and cesium carbonate (310 mg, 0.95 mmol). The mixture was heated to 110° C. overnight, then the crude reaction was filtered through celite, concentrated and purified by column chromatography (40% acetone/60% hexanes) to furnish 3-[1-ethyl(N-(2-(5-fluoro)pyridine)-sulfoximinyl)(methyl)]-6-trifluoro-methylpyridine (1) as an orange oil in 52% yield as a 1:1 mixture of diastereomers. $^1$H NMR (400 MHz, CDCl$_3$) δ (mixture of diastereomers) 8.79 (d, 1H), 8.78 (d, 1H), 8.02-8.09 (m, 4H), 7.74 (d, 1H), 7.72 (d, 1H), 7.24-7.29 (m, 2H), 6.78 (dd, 1H), 6.72 (dd, 1H), 5.16 (q, 1H), 5.07 (q, 1H), 3.14 (s, 3H), 3.06 (s, 3H), 1.92 (d, 3H), 1.89 (d, 3H); LC-MS (ESI): Mass calcd for $C_{14}H_{13}F_4N_3OS$ [M]$^+$, 348. Found 348.

Example II

Preparation of 3-[1-ethyl(N-(2-(5-chloro)pyridine)-sulfoximinyl)(methyl)]-6-trifluoromethylpyridine (2)

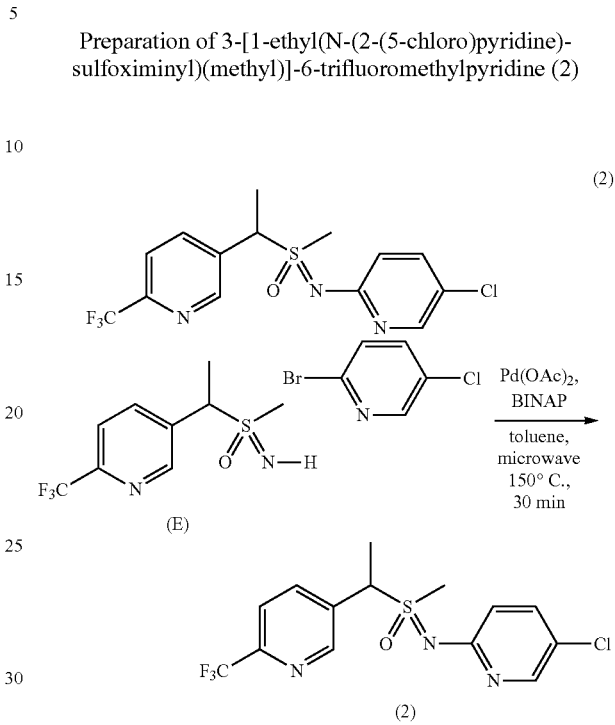

To a mixture of palladium(II) acetate (2 mg, 0.01 mmol) and rac-2,2'-Bis(diphenylphosphino)-1,1' binaphthyl (7.5 mg, 0.01 mmol) in toluene (1 mL) was added 2-chloro-5-fluoropyridine (32 mg, 0.17 mmol), 5-[1-(methylsulfonimidoyl)ethyl]-2-trifluoromethylpyridine (E) (50 mg, 0.2 mmol) and cesium carbonate (77 mg, 0.24 mmol). The mixture was heated in a microwave at 150° C. for 30 minutes, then the crude reaction was diluted with CH$_2$Cl$_2$ (1 mL), filtered through celite, concentrated and purified by column chromatography (SiO$_2$, 40% acetone/60% hexanes) to furnish 3-[1-ethyl(N-(2-(5-chloro)pyridine)-sulfoximinyl)(methyl)]-6-trifluoromethylpyridine (2) as an orange oil in 99% yield as a 1:1 mixture of diastereomers. $^1$H NMR (400 MHz, CDCl$_3$) δ (mixture of diastereomers) 8.75-8.80 (m, 2H), 8.06-8.15 (m, 4H), 7.74 (m, 2H), 7.48 (dd, 1H), 7.45 (dd, 1H), 6.76 (d, 1H), 6.70 (d, 1H), 5.18 (q, 1H), 5.08 (q, 1H), 3.16 (s, 3H), 3.08 (s, 3H), 1.93 (d, 3H), 1.90 (d, 3H); LC-MS (ESI): Mass calcd for $C_{14}H_{14}ClF_3N_3OS$ [M+H]$^+$, 365. Found 365.

Example III

Preparation of 3-[1-ethyl(N-(2-(4-fluoro)pyridine)-sulfoximinyl)(methyl)]-6-trifluoromethylpyridine (3)

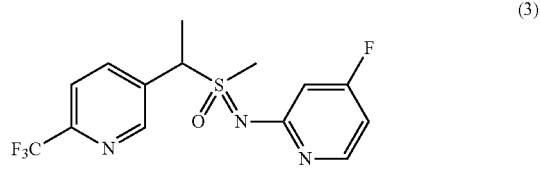

-continued

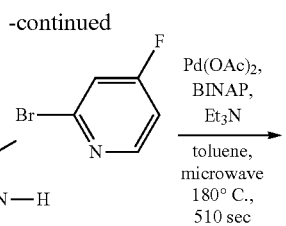
(E)

Pd(OAc)₂,
BINAP,
Et₃N
————→
toluene,
microwave
180° C.,
510 sec

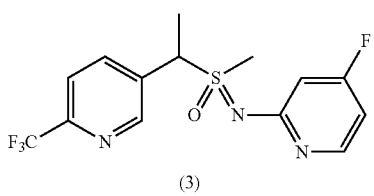
(3)

To a solution of toluene (3 ml), palladium(II) acetate (0.007 g, 0.032 mmol) and rac-2,2'-Bis(diphenylphosphino)-1,1' binaphthyl (0.029 g, 0.048 mmol) was added 5-[1-(methylsulfonimidoyl)ethyl]-2-trifluoromethylpyridine (E) (0.2 g, 0.793 mmol), 2-bromo-4-fluoropyridine (0.088 g, 0.674 mmol), cesium carbonate (0.309 g, 0.951 mol) and triethylamine (0.110 ml, 0.793 mmol). The reaction was heated in a microwave at 180° C. for 510 seconds. The solution was concentrated to dryness and the dark solid was suspended in water and extracted with EtOAc (3×100 ml). The EtOAc layers were combined, dried (MgSO₄), filtered and concentrated to dryness. The crude product was purified by chromatography on silica gel (eluent: 50-60% EtOAc/hexanes) to give a 3:2 mixture of diastereomers of 3-[1-ethyl(N-(2-(4-fluoro)pyridine)-sulfoximinyl)(methyl)]-6-trifluoromethylpyridine (3) as a yellow oil (0.036 g, 15%). $^1$H NMR (δ, CDCl₃): 8.8 (m, 2H), 8.1 (m, 4H), 7.7 (m, 2H), 6.5 (m, 4H), 5.1 (m, 2H), 3.2 (s, 3H), 3.1 (s, 3H), 1.9 (m, 6H); M+2H=349.2.

TABLE 1

Compounds

| Cmpd # | Structure | Route | Characterization |
|---|---|---|---|
| 4 | 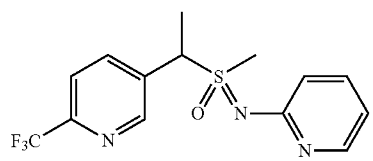 [SMILES: CC(c1ccc(C(F)(F)F)nc1)S(C)(=O)=Nc1ccccn1] | A | 1:1 mixture of two diastereomers $^1$H NMR (400 MHz, CDCl₃) δ 8.79 (d, 2H), 8.07-8.19 (m, 4H), 7.72 (dd, 2H), 7.48-7.55 (m, 2H), 6.82 (m, 4H), 5.31 (q, 1H), 5.18 (q, 1H), 3.17 (s, 3H), 3.08 (s, 3H), 1.93 (d, 3H), 1.89 (d, 3H); LC-MS (ESI): Mass calcd for C₁₄H₁₄F₃N₃OS [M]⁺, 329. Found 329. |
| 5 | 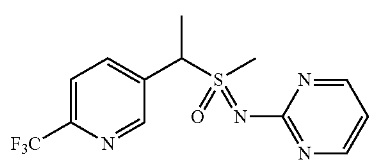 [SMILES: CC(c1ccc(C(F)(F)F)nc1)S(C)(=O)=Nc1ncccn1] | A | 1:1 mixture of two diastereomers $^1$H NMR (400 MHz, CDCl₃) δ 8.84 (d, 1H), 8.79 (d, 1H), 8.48 (dd, 2H), 8.28 (dd, 1H), 8.14 (dd, 1H), 7.77 (d, 2H), 6.82 (m, 2H), 4.99 (q, 1H), 4.95 (q, 1H), 3.21 (s, 3H), 3.18 (s, 3H), 2.01 (d, 3H), 1.98 (d, 3H); LC-MS (ESI): Mass calcd for C₁₃H₁₄F₃N₄OS [M + H]+, 331. Found 331. |
| 6 | 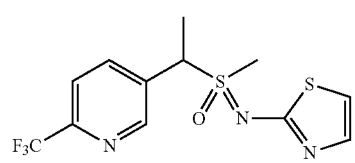 [SMILES: CC(c1ccc(C(F)(F)F)nc1)S(C)(=O)=Nc1nccs1] | A | 1:1 mixture of two diastereomers $^1$H NMR (400 MHz, CDCl₃) δ 8.81 (dd, 2H), 8.09-8.11 (m, 2H), 7.72-7.81 (m, 2H), 7.22-7.29 (m, 2H), 6.74-6.77 (m, 2H), 5.27 (q, 1H), 5.16 (q, 1H), 3.22 (s, 3H), 3.11 (s, 3H), 1.97 (d, 3H), 1.93 (d, 3H); LC-MS (ESI): Mass calcd for C₁₂H₁₂F₃N₃OS₂ [M]⁺, 335. Found 335. |
| 7 | 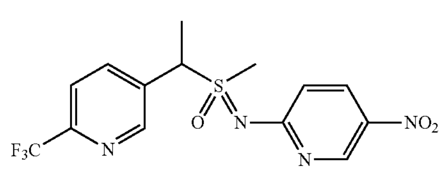 [SMILES: CC(c1ccc(C(F)(F)F)nc1)S(C)(=O)=Nc1ccc([N+](=O)[O-])cn1] | B | 1:1 mixture of two diastereomers $^1$H NMR (300 MHz, CDCl₃) δ 9.10 (dd, 2H), 8.83 (dd, 2H), 8.30 (m, 2H), 8.12 (m, 2H), 7.79 (dd, 2H), 6.88 (d, 1H), 6.80 (d, 1H), 5.11 (q, 1H), 5.08 (q, 1H), 3.30 (s, 3H), 3.23 (s, 3H), 1.99 (d, 3H), 1.95 (d, 3H); LC-MS (ESI): Mass calcd for C₁₄H₁₄F₃N₄O₃S [M + H]⁺, 375. Found 375. |

TABLE 1-continued

Compounds

| Cmpd # | Structure | Route | Characterization |
|---|---|---|---|
| 8 | 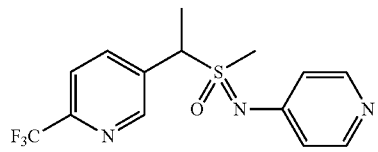 [SMILES: CC(c1ccc(C(F)(F)F)nc1)S(C)(=O)=Nc1ccncc1] | A | 3:2 mixture of diastereomers <br> $^1$H NMR (300 MHz, CDCl$_3$) δ 8.81 (d, 1H), 8.79 (d, 1H), 8.3 (m, 4H0, 8.1 (m, 2H), 7.8 (s, 1H), 7.7 (s, 1H), 6.8 (m, 2H), 4.6 (m, 2H), 3.0 (s, 3H), 2.9 (s, 3H), 2.9 (m, 3H); <br> M + H = 330.24. |
| 9 | 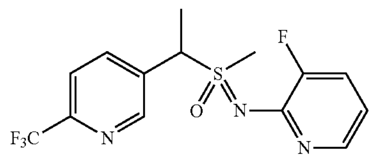 [SMILES: CC(c1ccc(C(F)(F)F)nc1)S(C)(=O)=Nc1ncccc1F] | C | 3:2 mixture of diastereomers <br> $^1$H NMR (300 MHz, CDCl$_3$) δ 8.8 (m, 2H), 8.1 (m, 4H), 7.7 (m, 2H), 6.5 (m, 4H), 5.2 (m, 2H), 3.2 (s, 3H), 3.1 (s, 3H), 2.0 (m, 6H); M + H = 347.9 |
| 10 | 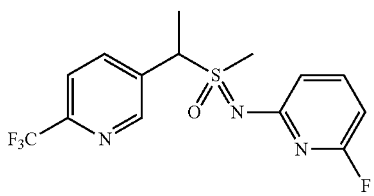 [SMILES: CC(c1ccc(C(F)(F)F)nc1)S(C)(=O)=Nc1cccc(F)n1] | C | 1:1 mixture of diastereomers <br> $^1$H NMR (300 MHz, CDCl$_3$) δ 8.8 (d, 1H), 8.7 (d, 1H) 8.1 (m, 2H), 7.5 (m, 2H), 6.6 (m, 2H), 6.4 (m, 2H), 5.1 (m, 2H), 3.1 (m, 6H), 1.8 (m, 6H); <br> M + H = 348.2. |
| 11 | 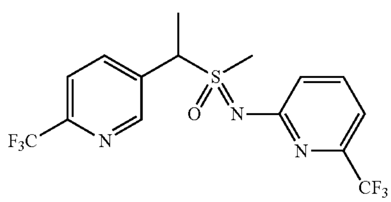 [SMILES: CC(c1ccc(C(F)(F)F)nc1)S(C)(=O)=Nc1cccc(C(F)(F)F)n1] | C | 3:2 mixture of diastereomers <br> $^1$H NMR (300 MHz, CDCl$_3$) δ 8.8 (d, 1H), 8.6 (d, 1H) 8.1 (m, 2H), 7.7 (m, 4H), 7.2 (m, 2H), 7.0 (d, 1H), 6.9 (d, 1H), 5.4 (m, 2H), 3.3 (s, 3H); 3.1 (s, 1H), 2.0 (d, 3H), 1.9 (s, 3H); <br> M + H = 398.2. |
| 12 | 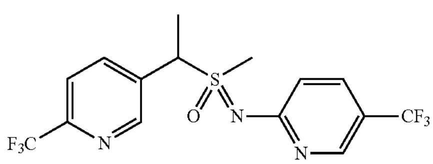 [SMILES: CC(c1ccc(C(F)(F)F)nc1)S(C)(=O)=Nc1ccc(C(F)(F)F)cn1] | B | 1:1 mixture of two diastereomers $^1$H NMR (400 MHz, CDCl$_3$) δ 8.81 (dd, 2H), 8.46 (dd, 2H), 8.11 (m, 2H), 7.68-7.79 (m, 4H), 7.18-7.27 (m, 2H), 6.90 (d, 1H), 6.82 (d, 1H), 5.19 (q, 1H), 5.12 (q, 1H), 3.24 (s, 3H), 3.16 (s, 3H), 1.97 (d, 3H), 1.93 (d, 3H); LC-MS (ESI): Mass calcd for C$_{15}$H$_{14}$F$_6$N$_3$OS [M + H]$^+$, 398. Found 398. |
| 13 | 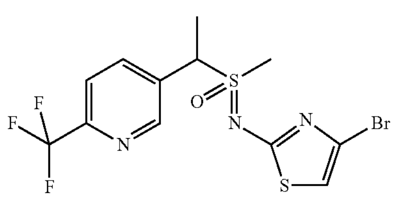 [SMILES: CC(c1ccc(C(F)(F)F)nc1)S(C)(=O)=Nc1nc(Br)cs1] | B | 1:1 mixture of two diastereomers $^1$H NMR (300 MHz, CDCl$_3$) δ 8.85 (d, 1H), 8.75 (d, 1H), 8.2 (m, 2H), 7.8 (m, 2H), 6.65 (s, 1H), 6.6 (s, 1H), 5.4 (m, 2H), 3.3 (s, 3H), 3.1 (s, 3H), 1.95 (d, 3H), 1.9 (d, 3H); LC-MS (ESI): Mass calcd for C$_{12}$H$_{11}$BrF$_3$N$_3$OS$_2$ [M + 2H]$^+$, 416. Found 416. |
| 14 | 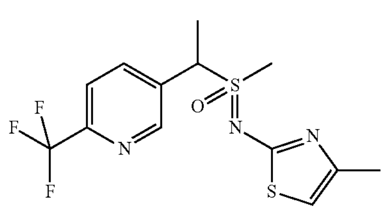 [SMILES: Cc1csc(N=S(C)(=O)C(C)c2ccc(C(F)(F)F)nc2)n1] | B | 1:1 mixture of two diastereomers $^1$H NMR (300 MHz, CDCl$_3$) δ 8.81 (d, 1H), 8.78 (d, 1H), 8.1 (m, 62H), 7.78 (m, 1H), 3.2 (s, 1H), 3.1 (s, 1H), 2.3 (d, 3H), 2.29 (d, 3H), 1.96 (d, 3H), 1.95 (d, 3H); LC-MS (ESI): Mass calcd for C$_{13}$H$_{14}$F$_3$N$_3$OS$_2$ [M + 2H]$^+$, 351. Found 351. |

TABLE 1-continued

| Cmpd # | Structure | Route | Characterization |
|---|---|---|---|
| 15 | 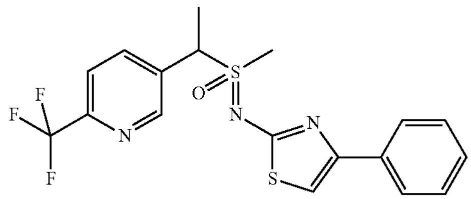 [SMILES: CC(c1ccc(C(F)(F)F)nc1)S(C)(=O)=Nc1nc(-c2ccccc2)cs1] | B | 1:1 mixture of two diastereomers $^1$H NMR (300 MHz, CDCl$_3$) δ 8.81 (d, 1H), 8.74 (d, 1H), 8.1 (m, 2H), 7.78 (m, 6H), 7.36 (m, 6H), 6.9 (d, 2H), 5.4 (m, 1H), 5.2 (m, 1H), 3.2 (s, 3H), 3.1 (s, 3H), 2.0 (d, 3H), 1.9 (d, 3H); LC-MS (ESI): Mass calcd for C$_{18}$H$_{16}$F$_3$N$_3$OS$_2$ [M]$^+$, 411. Found 411. Mp = 88-93° C. |
| 16 | 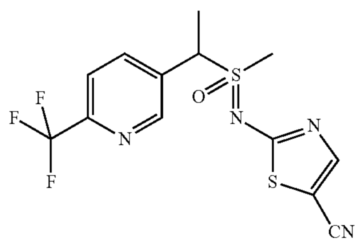 [SMILES: CC(c1ccc(C(F)(F)F)nc1)S(C)(=O)=Nc1ncc(C#N)s1] | B | 1:1 mixture of two diastereomers $^1$H NMR (400 MHz, CDCl$_3$) δ 8.81 (d, 1H), 8.71 (d, 1H), 8.06 (d, 1H), 7.78 (m, 2H), 7.73 (s, 1H), 7.70 (s, 1H), 5.04 (m, 2H), 3.25 (s, 3H), 3.17 (s, 3H), 1.97 (d, 3H), 1.93 (d, 3H); LC-MS (ESI): Mass calcd for C$_{13}$H$_{12}$F$_3$N$_4$OS$_2$ [M + H]$^+$, 361.1. Found 361.1. |
| 17 | 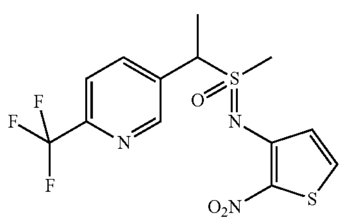 [SMILES: CC(c1ccc(C(F)(F)F)nc1)S(C)(=O)=Nc1ccsc1[N+](=O)[O-]] | B | 1:1 mixture of two diastereomers $^1$H NMR (400 MHz, CDCl$_3$) δ 8.0 (d, 1H), 8.76 (d, 1H), 8.46 (dd, 1H), 8.12 (dd, 1H), 7.76 (d, 1H), 7.69 (d, 1H), 7.20 (m, 2H), 6.88 (d, 1H), 6.80 (d, 1H), 4.64 (m, 1H), 4.66 (m, 1H), 3.13 (s, 3H), 3.05 (s, 3H), 2.03 (d, 3H), 1.97 (d, 3H); LC-MS (ESI): Mass calcd for C$_{13}$H$_{15}$F$_3$N$_3$O$_3$S$_2$ [M + H]$^+$, 380.1. Found 380.1. |
| 18 | 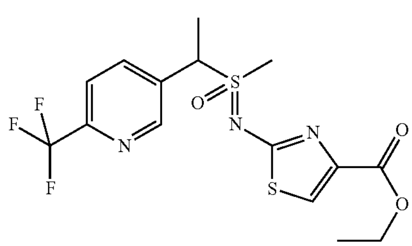 [SMILES: CCOC(=O)c1csc(N=S(C)(=O)C(C)c2ccc(C(F)(F)F)nc2)n1] | B | 1:1 mixture of two diastereomers $^1$H NMR (400 MHz, CDCl$_3$) δ 8.8 (d, 1H), 8.7 (d, 1H), 8.15 (dd, 1H), 8.1 (dd, 1H), 7.75 (m, 2H), 7.62 (s, 1H), 7.59 (s, 1H), 5.39 (m, 1H), 5.31 (m, 1H), 4.35 (m, 4H), 3.3 (s, 3H), 3.13 (s, 3H), 1.96 (d, 3H), 1.88 (d, 3H), 1.39 (m, 6H); LC-MS (ESI): Mass calcd for C$_{15}$H$_{17}$F$_3$N$_3$O$_3$S$_2$ [M + H]$^+$, 408.1. Found 408.1. |

A = route used in example I;
B = route used in example II;
C = route used in example III.

Example IV

Preparation of 5-{1-[methyl(4-(4-methylphenyl)-1,3-thiazol-2-yl)sulfonimidoyl]ethyl}-2-(trifluoromethyl)pyridine (19)

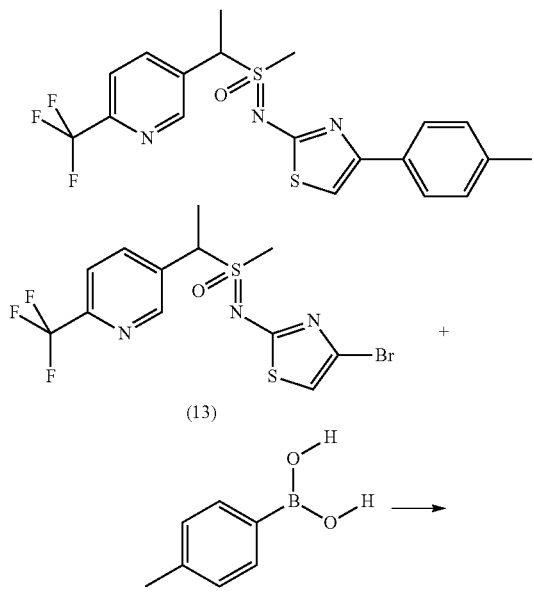

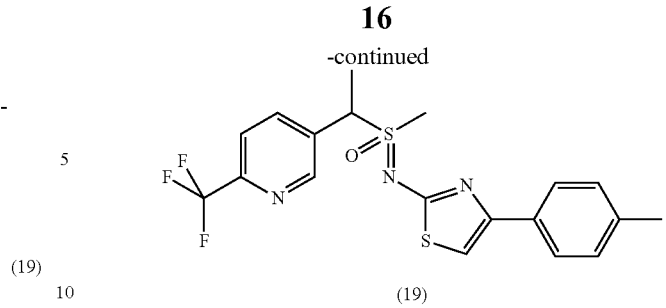

A suspension of 5-{1-[methyl(4-bromo-1,3-thiazol-2-yl)sulfonimidoyl]ethyl}-2-(trifluoromethyl)pyridine (13) (0.055 g, 0.133 mmol), 4-methylphenyl boronic acid (0.027 g, 0.199 mmol) and tetrakis(triphenylphosphine)palladium (0) (0.006 g, 0.005 mmol) in dioxane (0.9 ml) and 2M $Na_2CO_3$ (0.070 g, in 0.33 ml of water) was heated at reflux for 2 hours. The reaction mixture was cooled and filtered. The filtrate was evaporated in vacuo and the residue was dissolved in EtOAc, and subsequently washed with water and brine. The combined organic layers were dried ($MgSO_4$), filtered and concentrated to dryness. The crude product was purified by column chromatography ($SiO_2$, with a gradient of 50% EtOAc/hexanes) to give 5-{1-[methyl(4-(4-methylphenyl)-1,3-thiazol-2-yl)sulfonimidoyl]ethyl}-2-(trifluoromethyl)pyridine (19) as a dark yellow semi-solid (0.039 g, 70%). 1:1 mixture of two diastereomers $^1$H NMR (300 MHz, $CDCl_3$) δ 8.85 (d, 1H), 8.75 (d, 1H), 8.1 (m, 2H), 7.7 (m, 6H), 7.2 (m, 4H), 6.9 (d, 2H), 5.4 (m, 1H), 5.2 (m, 1H), 3.3 (s, 3H), 3.1 (s, 3H), 2.4 (d, 6H), 2.0 (d, 3H), 1.9 (d, 3H); LC-MS (ESI): Mass calcd for $C_{19}H_{18}F_3N_3OS_2$ $[M+H]^+$, 426. Found 426.

TABLE 2

Compounds

| Cmpd # | Structure | Route | Characterization |
|---|---|---|---|
| 20 | 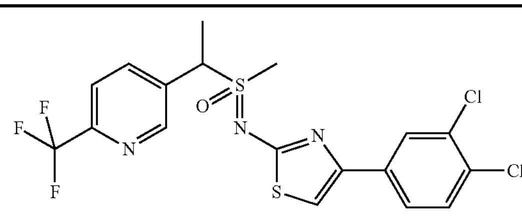 | D | 1:1 mixture of two diastereomers $^1$H NMR (300 MHz, $CDCl_3$) δ 8.85 (d, 1H), 8.8 (d, 1H), 8.1 (m, 2H), 7.9 (m, 2H), 7.75 (m, 2H), 7.6 (m, 2H), 7.4 (m, 2H), 6.95 (s, 2H), 5.1 (m, 2H), 3.3 (s, 3H), 3.2 (s, 3H), 2.0 (m, 6H); LC-MS (ESI): Mass calcd for $C_{18}H_{14}Cl_2F_3N_3OS_2$ $[M]^+$, 480. Found 480. |
| 21 | 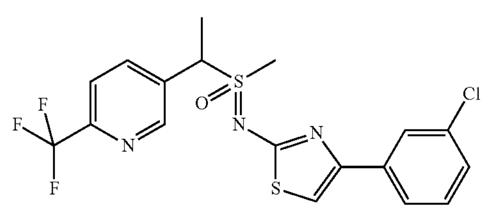 [SMILES: CC(c1ccc(C(F)(F)F)nc1)S(C)(=O)=Nc1nc(-c2cccc(Cl)c2)cs1] | D | 1:1 mixture of two diastereomers $^1$H NMR (300 MHz, $CDCl_3$) δ 8.81 (s, 1H), 8.79 (s, 1H), 8.1 (m, 2H), 7.7 (m, 6H), 7.3 (m, 4H), 7.9 (s, 2H), 5.2 (m, 2H), 3.3 (s, 3H), 3.2 (s, 3H), 2.0 (d, 3H), 1.9 (d, 3H); Mass calcd for $C_{18}H_{15}ClF_3N_3OS_2$ $[M + H]^+$, 445, Found 446. |
| 22 | 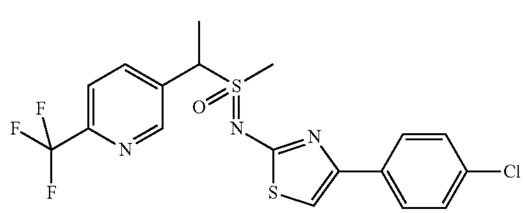 [SMILES: CC(c1ccc(C(F)(F)F)nc1)S(C)(=O)=Nc1nc(-c2ccc(Cl)cc2)cs1] | D | 1:1 mixture of two diastereomers $^1$H NMR (300 MHz, $CDCl_3$) δ 8.81 (s, 1H), 8.79 (s, 1H), 8.1 (m, 2H), 7.75 (m, 6H), 7.4 (m, 4H), 6.95 (s, 1H), 6.94 (s, 1H), 5.2 (m, 2H), 3.3 (s, 3H), 3.1 (s, 3H), 2.0 (d, 3H), 1.9 (d, 3H); Mass calcd for $C_{18}H_{15}ClF_3N_3OS_2$ $[M + H]^+$, 445, Found 446. |

TABLE 2-continued

Compounds

| Cmpd # | Structure | Route | Characterization |
|---|---|---|---|
| 23 | 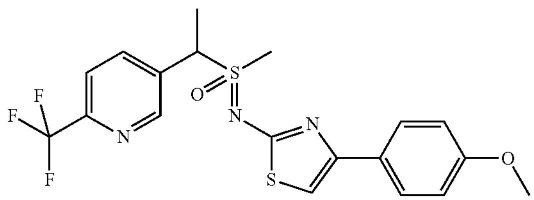 [SMILES: COc1ccc(-c2csc(N=S(C)(=O)C(C)c3ccc(C(F)(F)F)nc3)n2)cc1] | D | 2:1 mixture of two diastereomers $^1$H NMR (300 MHz, CDCl$_3$) δ 8.81 (s, 1H), 8.79 (s, 1H), 8.1 (m, 2H), 7.7 (m, 6H), 6.9 (m, 4H), 6.8 (s, 1H), 6.79 (s, 1H), 5.4 (m, 2H), 3.8 (s, 3Hx2), 3.3 (s, 3H), 3.2 (s, 3H), 2.0 (d, 3H), 1.9 (d, 3H); Mass calcd for C$_{19}$H$_{18}$F$_3$N$_3$O$_2$S$_2$ [M + H]$^+$, 442, Found 442. |

D = route used in example IV

Example V

Preparation of 3-[1-ethyl(N-(1-oxy-pyridin-2-e)-sulfoximinyl)(methyl)]-6-trifluoromethylpyridine (24)

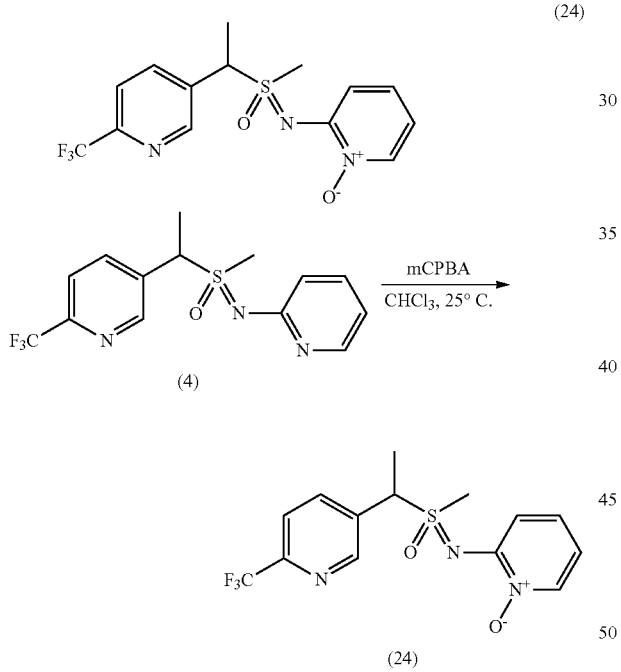

To a solution of 3-[1-ethyl(N-(2-pyridine)-sulfoximinyl)(methyl)]-6-trifluoromethylpyridine (4) (100 mg, 0.3 mmol) in CHCl$_3$ (2 mL) was added m-chloroperoxy benzoic acid (mCPBA) (70% purity, 105 mg, 0.6 mmol). The solution immediately turned from orange to yellow upon addition. After 1 h, the crude reaction mixture was washed with aqueous sodium bisulfite and aqueous NaHCO$_3$, dried and concentrated to furnish 3-[1-ethyl(N-(1-oxy-pyridin-2-e)-sulfoximinyl)(methyl)]-6-trifluoro-methylpyridine (24) as a yellow solid in 23% yield as a 1:1 mixture of diastereomers. Mp=43-47° C.; $^1$H NMR (400 MHz, CDCl$_3$) δ (mixture of diastereomers) 8.86 (dd, 2H), 8.20 (dd, 1H), 8.06-8.12 (m, 3H), 7.73 (d, 2H), 7.09-7.15 (m, 2H), 6.98 (dd, 1H), 6.89 (dd, 1H), 6.79-6.85 (m, 2H), 5.21 (q, 1H), 5.11 (q, 1H), 3.36 (s, 3H), 3.33 (s, 3H), 1.99 (d, 3H), 1.95 (d, 3H); LC-MS (ESI): Mass calcd for C$_{14}$H$_{15}$F$_3$N$_3$O$_2$S [M+H]$^+$, 346. Found 346.

Example VI

Preparation of 3-[1-ethyl(N-(2-benzothiazole)-sulfoximinyl)(methyl)]-6-trifluoromethylpyridine (25)

To a solution of 5-(1-methylsulfanyl-ethyl)-2-trifluoromethylpyridine (0.5 g, 2.25 mmol) and 2-benzothiazole (0.37 g, 2.48 mmol) in dichloromethane (8 ml) cooled to −25° C. was slowly added N-chlorosuccinamide (0.33 g, 2.48 mmol) while maintaining the internal temperature of the reaction between −22° C. and −28° C. The reaction was slowly warmed to room temperature and stirred an additional hour. The reaction mixture was washed with water and the dichloromethane layer was dried (MgSO$_4$), filtered and concentrated to dryness. The crude product was purified by chromatography on silica gel (eluent: 50% EtOAc/hexanes, 100% EtOAc) to give 3-[1-ethyl(N-(2-benzothiazole)-sulfinyl)(methyl)]-6-trifluoromethylpyridine (F) as a yellow solid (0.37 g, 45%); M+H=371.1.

(25)

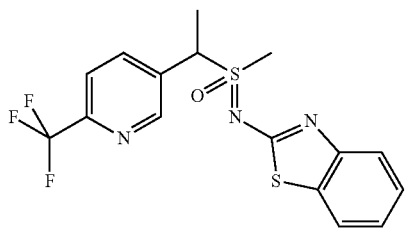

To a solution of 77% mCPBA (0.34 g, 1.5 mmol) in EtOH (5 ml) at 0° C. was added a solution of potassium carbonate (0.42 g, 3.0 mmol) in water (5 ml) and stirred for 20 minutes. To this was added 3-[1-ethyl(N-(2-benzothiazole)-sulfinyl) (methyl)]-6-trifluoromethylpyridine (F) (0.37 g, 1.0 mmol) in EtOH (5 ml) and stirred for 1 hour at 0° C. The reaction mixture was concentrated to dryness and the white solid was suspended in dichloromethane (100 ml) and filtered to remove solids. The filtrate was collected and concentrated to dryness. The crude product was purified by chromatography on silica gel (eluent: 30-50% EtOAc/hexanes) to give a 3:2 mixture of diastereomers of 3-[1-ethyl(N-(2-benzothiazole)-sulfoximinyl)(methyl)]-6-trifluoromethylpyridine (25) as a yellow semi-solid (0.073 g, 18%). $^1$H NMR (δ, CDCl$_3$): 8.81 (d, 1H), 8.79 (d, 1H), 8.1 (m, 2H), 7.7 (m, 6H), 7.3 (m, 4H), 5.3 (m, 2H), 3.3 (s, 3H), 3.2 (s, 3H), 2.0 (m, 6H).

Example VII

Preparation of 3-[1-ethyl(N-(2-(4-trifluoromethyl) thiazole)-sulfoximinyl)(methyl)]-6-trifluoromethylpyridine (26)

(26)

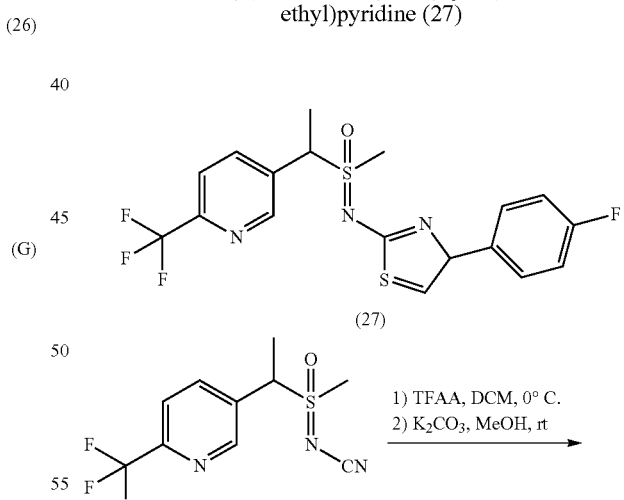

To a solution of 5-(1-methylsulfanyl-ethyl)-2-trifluoromethylpyridine (0.5 g, 2.25 mmol) and 2-amino-4-trifluoromethyl thiazole (0.42 g, 2.48 mmol) in dichloromethane (8 ml) cooled to −25° C. was slowly added N-chlorosuccinamide (0.33 g, 2.48 mmol) while maintaining the internal temperature of the reaction between −22° C. and −28° C. The reaction was slowly warmed to room temperature and stirred an additional hour. The reaction mixture was washed with water and the dichloromethane layer was dried (MgSO$_4$), filtered and concentrated to dryness. The crude product was purified by chromatography on silica gel (eluent: 50% EtOAc/hexanes, 100% EtOAc) to give 3-[1-ethyl(N-(2-(4-trifluoromethyl) thiazole)-sulfinyl)(methyl)]-6-trifluoromethylpyridine (G) as a yellow solid (0.81 g, 93%); M+H=288.1.

(26)

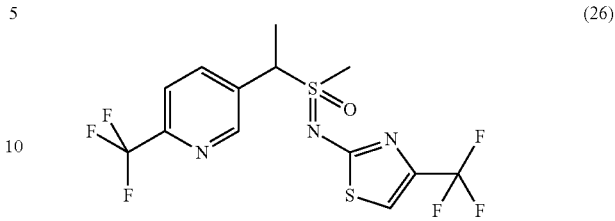

To a solution of 77% mCPBA (0.69 g, 3.14 mmol) in EtOH (5 ml) at 0° C. was added a solution of K$_2$CO$_3$ (0.87 g, 6.3 mmol) in water (5 ml) and stirred for 20 minutes. To this was added 3-[1-ethyl(N-(2-(4-trifluoromethyl)thiazole)-sulfinyl) (methyl)]-6-trifluoromethylpyridine (G) (0.81 g, 2.1 mmol) in EtOH (5 ml) and stirred for 1 hour at 0° C. The reaction mixture was concentrated to dryness and the white solid was suspended in dichloromethane (100 ml) and filtered to remove solids. The filtrate was collected and concentrated to dryness. The crude product was purified by chromatography on silica gel (eluent: 30-50% EtOAc/hexanes) to give a 3:2 mixture of diastereomers of 3-[1-ethyl(N-(2-(4-trifluoromethyl)thiazole)-sulfoximinyl)(methyl)]-6-trifluoromethylpyridine (26) as a yellow semi-solid (0.073 g, 18%). $^1$H NMR (δ, CDCl$_3$): 8.6 (d, 1H), 8.6 (d, 1H), 8.1 (m, 2H), 7.7 (m, 2H), 7.1 (m, 2H), 5.1 (m, 2H), 3.3 (s, 3H), 3.2 (s, 3H), 1.9 (m, 6H); M+H=404.1.

Example VIII

Preparation of 5-{1-[methyl(4-(4-fluorophenyl)-1,3-thiazol-2-yl)sulfonimidoyl]ethyl}-2-(trifluoromethyl)pyridine (27)

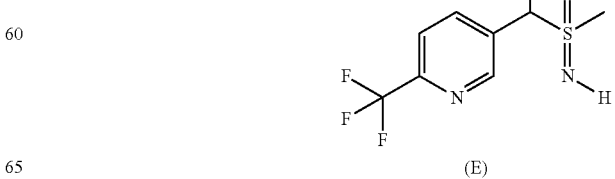

[1-(6-Trifluoromethylpyridin-3-yl)ethyl](methyl)-oxido-λ⁴-sulfanylidenecyan-amide (H) was prepared as described in patent WO 2007095229 (Example II). To a stirring solution of sulfoximine (H) (5.0 g, 18 mmol) in $CH_2Cl_2$ (300 mL) at 0° C. was added trifluoroacetic anhydride (7.5 mL, 54 mmol). The mixture was allowed to react at room temperature until the starting material was fully consumed (2 h as monitored by TLC). The reaction mixture was concentrated in vacuo, dissolved in methanol (125 mL) and treated with $K_2CO_3$ (12.5 g, 90 mmol). The mixture was allowed to stir at room temperature until the starting material was consumed (2 h as monitored by TLC). The crude reaction mixture was filtered, concentrated and purified by chromatography (acetone:hexanes) to furnish 5-[1-(methylsulfonimidoyl)ethyl]-2-trifluoromethylpyridine (E) as a white solid (3.5 g, 77%). ¹H NMR (400 MHz, acetone-$D_6$) δ (mixture of diastereomers) 8.9 (s, 1H), 8.2 (m, 1H), 7.9 (d, 1H), 4.6 (q, 1H), 2.8 (s, 3H), 1.8 (d, 3H); LC-MS (ESI): Found [M]⁺ 252. Calcd for $C_9H_{11}F_3N_2OS$=252.

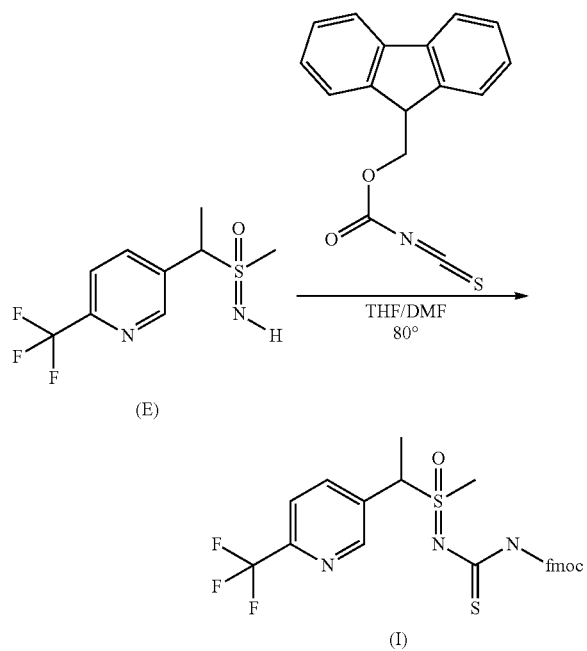

(E)

(I)

In a 50 mL RBF charged with a magnetic stirbar, 5-[1-(methylsulfonimidoyl)ethyl]-2-trifluoromethylpyridine (E) (0.236 g, 0.937 mmol) was dissolved in 5:1 THF:DMF (21 mL) at room temperature Next, the isothiocyanate (0.368 g, 1.3 μmol) was added to the reaction flask and the reaction was warmed to 80° C. for 12 h. Upon completion of reaction, the mixture was poured into a separatory funnel, diluted with EtOAc, and then with brine. The aqueous layer was extracted with EtOAc. The organics were combined, washed with brine, dried over anhydrous $Na_2SO_4$, filtered, and then concentrated in vacuo. The crude material was purified by chromatography to furnish sulfoximine (I) as a yellow solid (0.297 g, 59%). ¹H NMR (400 MHz, CDCl₃) δ (mixture of diastereomers) 8.84 (s, 1H), 8.36 (q, 1H), 8.22 (d, 1H), 7.69 (q, 4H), 7.75 (t, 1H), 7.43 (t, 2H), 7.34 (t, 2H), 5.04 & 4.80 (m, 1H), 4.49 & 4.26 (m, 3H), 3.50 & 3.43 (s, 3H), 1.97 (m, 3H); LC-MS (ESI): Found [M+H]⁺ 534. Calcd for $C_{25}H_{22}F_3N_3O_3S_2$=533.

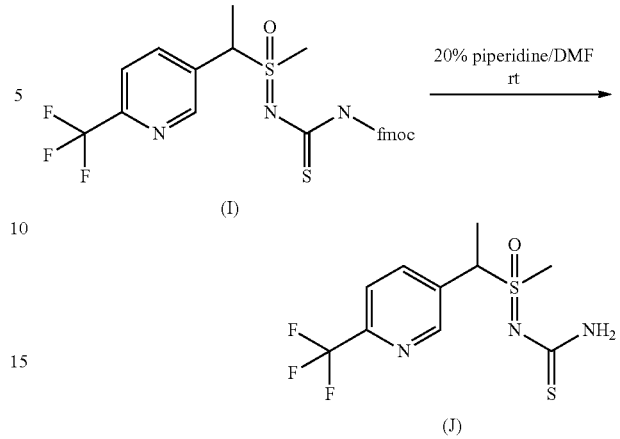

In a 5 mL RBF charged with a magnetic stirbar, sulfoximine (I) (0.100 g, 0.187 mmol) was dissolved in 2 mL piperidine/DMF at rt with stirring. Upon completion of reaction, the mixture was concentrated in vacuo. The crude material was purified by chromatography to furnish thiourea (J) as an off-white solid (0.043 g, 74%). ¹H NMR (400 MHz, CDCl₃) δ (mixture of diastereomers) 8.86 (s, 1H), 8.10 (m, 1H), 7.76 (m, 1H), 6.09 & 5.94 (m, 1H), 3.52 & 3.24 (s, 3H), 1.88 (d, 3H); LC-MS (ESI): Found [M+H]⁺ 312.1. Calcd for $C_{10}H_{12}F_3N_3OS_2$=311.

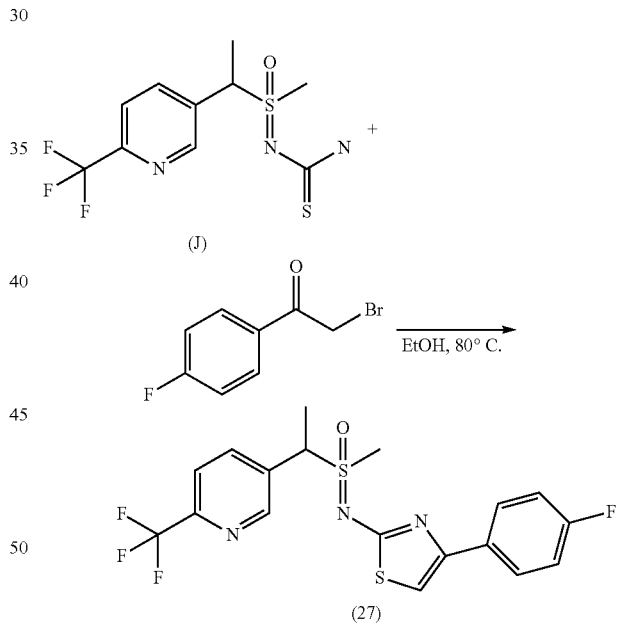

To a suspension of sulfoximine (J) (50 mg, 0.2 mmol) in ethanol (1 mL) was added bromo-4-fluoroacetophenone (40 μL, 0.2 mmol) and the reaction was stirred at 70° C. for 4 hours. The reaction was then concentrated and purified by chromatography to furnish 5-{1-[methyl(4-(4-fluorophenyl)-1,3-thiazol-2-yl)sulfonimidoyl]ethyl}-2-(trifluoromethyl)pyridine (27) as a white solid=29 mg (42%). mp=89-94° C. ¹H NMR (400 MHz, CDCl₃) δ (1:1 mixture of two diastereomers) 8.83 (s, 1H), 8.77 (s, 1H), 8.11 (m, 2H), 7.73-7.80 (m, 6H), 7.05-7.11 (m, 4H), 6.86 (d, 2H), 5.28 (q, 1H), 5.17 (q, 1H), 3.28 (s, 3H), 3.17 (s, 3H), 2.00 (d, 3H), 1.94 (d, 3H); LC-MS (ESI): Mass calcd for $C_{18}H_{16}F_4N_3OS_2$ [M+1]⁺, 430. Found 430.

TABLE 3

| Cmpd # | Structure | Route | Characterization |
|---|---|---|---|
| 28 | 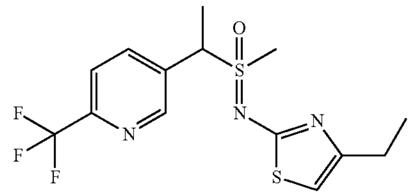 [SMILES: CCc1csc(N=S(C)(=O)C(C)c2ccc(C(F)(F)F)nc2)n1] | E | Brown oil. 1:1 mixture of two diastereomers; $^1$H NMR (400 MHz, CDCl$_3$) δ 8.79 (s, 1H), 8.73 (s, 1H), 8.09 (d, 2H), 7.74 (m, 2H), 6.28 (d, 2H), 5.25 (q, 1H), 5.14 (q, 1H), 3.20 (s, 3H), 3.08 (s, 3H), 2.63 (m, 4H), 1.96 (d, 3H), 1.90 (d, 3H), 1.26 (m, 6H); LC-MS (ESI): Mass calcd for C$_{14}$H$_{17}$F$_3$N$_3$OS$_2$ [M + 1]$^+$, 364. Found 364. |
| 29 | 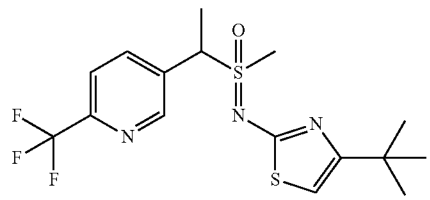 [SMILES: CC(c1ccc(C(F)(F)F)nc1)S(C)(=O)=Nc1nc(C(C)(C)C)cs1] | E | Tan solid, mp = 144-148° C. 1:1 mixture of two diastereomers; $^1$H NMR (400 MHz, CDCl$_3$) δ 8.80 (s, 1H), 8.68 (s, 1H), 8.11 (dd, 1H), 8.05 (dd, 1H), 7.77 (d, 1H), 7.71 (d, 1H), 6.29 (d, 2H), 5.37 (q, 1H), 5.24 (q, 1H), 3.24 (s, 3H), 3.07 (s, 3H), 1.96 (d, 3H), 1.87 (d, 3H), 1.32 (s, 9H), 1.30 (s, 9H); LC-MS (ESI): Mass calcd for C$_{16}$H$_{21}$F$_3$N$_3$OS$_2$ [M + 1]$^+$, 392. Found 392. |
| 30 | 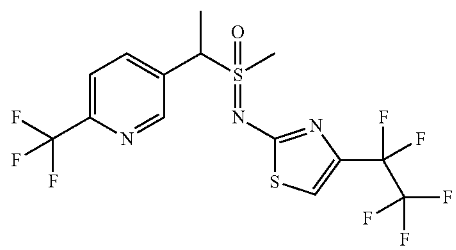 [SMILES: CC(c1ccc(C(F)(F)F)nc1)S(C)(=O)=Nc1nc(C(F)(F)C(F)(F)F)cs1] | E | White solid, mp = 95-100° C. 1:1 mixture of two diastereomers; $^1$H NMR (400 MHz, CDCl$_3$) δ 8.79 (s, 1H), 8.67 (s, 1H), 8.08 (dd, 1H), 8.02 (dd, 1H), 7.78 (d, 1H), 7.73 (d, 1H), 7.20 (d, 2H), 5.29 (q, 1H), 5.19 (q, 1H), 3.28 (s, 3H), 3.10 (s, 3H), 1.97 (d, 3H), 1.87 (d, 3H); LC-MS (ESI): Mass calcd for C$_{14}$H$_{12}$F$_8$N$_3$OS$_2$ [M + 1]$^+$, 454. Found 454. |
| 31 | 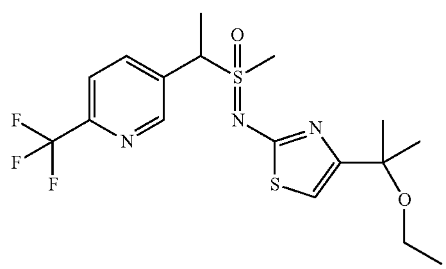 [SMILES: CCOC(C)(C)c1csc(N=S(C)(=O)C(C)c2ccc(C(F)(F)F)nc2)n1] | E | Yellow oil. 1:1 mixture of two diastereomers; $^1$H NMR (400 MHz, CDCl$_3$) δ 8.80 (s, 1H), 8.68 (s, 1H), 8.11 (dd, 1H), 8.05 (dd, 1H), 7.76 (d, 1H), 7.72 (d, 1H), 6.54 (d, 2H), 5.33 (q, 1H), 5.25 (q, 1H), 3.30-3.36 (m, 4H), 3.17 (s, 3H), 3.08 (s, 3H), 1.96 (d, 3H), 1.87 (d, 3H), 1.55 (s, 12H), 1.17 (m, 6H); LC-MS (ESI): Mass calcd for C$_{17}$H$_{22}$F$_3$N$_3$O$_2$S$_2$ [M]$^+$, 421. Found 421. |
| 32 | 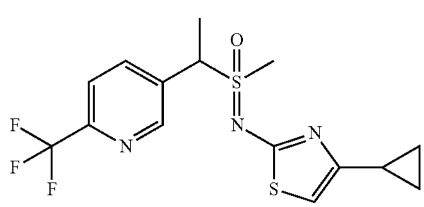 [SMILES: CC(c1ccc(C(F)(F)F)nc1)S(C)(=O)=Nc1nc(C2CC2)cs1] | E | White solid, mp = 102-106° C. 1:1 mixture of two diastereomers; $^1$H NMR (400 MHz, CDCl$_3$) δ 8.78 (s, 1H), 8.72 (s, 1H), 8.05 (m, 2H), 7.76 (d, 1H), 7.72 (d, 1H), 6.28 (s, 1H), 6.25 (s, 1H), 5.20 (q, 1H), 5.09 (q, 1H), 3.17 (s, 3H), 3.04 (s, 3H), 1.94 (d, 6H), 1.84-1.90 (m, 2H), 0.81-0.90 (m, 8H); LC-MS (ESI): Mass calcd for C$_{15}$H$_{16}$F$_3$N$_3$OS$_2$ [M]$^+$, 375. Found 375. |

TABLE 3-continued

Compounds

| Cmpd # | Structure | Route | Characterization |
|---|---|---|---|
| 33 | 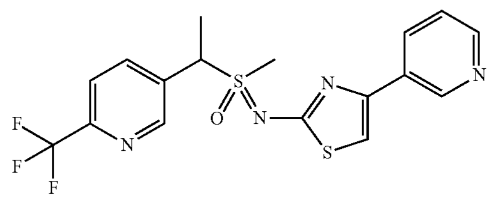 [SMILES: CC(c1ccc(C(F)(F)F)nc1)S(C)(=O)=Nc1nc(-c2cccnc2)cs1] | E | Off-white solid, mp = 178-182° C. 1:1 mixture of two diastereomers; $^1$H NMR (400 MHz, CDCl$_3$) δ 9.09 (s, 2H), 8.84 (s, 1H), 8.76 (s, 1H), 8.54 (s, 2H), 8.07-8.12 (m, 4H), 7.76 (dd, 2H), 7.35 (s, 2H), 7.04 (s, 1H), 7.02 (s, 1H), 5.23 (q, 1H), 5.17 (q, 1H), 3.30 (s, 3H), 3.19 (s, 3H), 2.01 (d, 3H), 1.96 (d, 3H); LC-MS (ESI): Mass calcd for C$_{17}$H$_{16}$F$_3$N$_4$OS$_2$ [M + H]$^+$, 413. Found 413. |
| 34 | 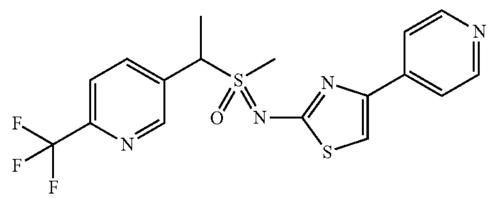 [SMILES: CC(c1ccc(C(F)(F)F)nc1)S(C)(=O)=Nc1nc(-c2ccncc2)cs1] | E | Brown oil. 1:1 mixture of two diastereomers; $^1$H NMR (400 MHz, CDCl$_3$) δ 8.84 (s, 1H), 8.79 (s, 1H), 8.62 (s, 4H), 8.11 (m, 2H), 7.74-7.79 (m, 6H), 7.24 (s, 1H), 7.22 (s, 1H), 5.18 (q, 1H), 5.09 (q, 1H), 3.31 (s, 3H), 3.20 (s, 3H), 2.00 (d, 3H), 1.97 (d, 3H); LC-MS (ESI): Mass calcd for C$_{17}$H$_{15}$F$_3$N$_4$OS$_2$ [M]$^+$, 412. Found 412. |
| 35 | 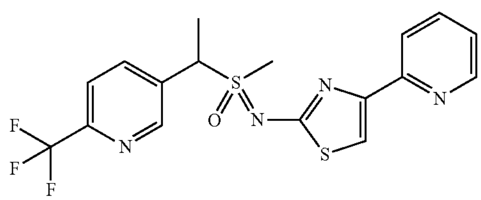 [SMILES: CC(c1ccc(C(F)(F)F)nc1)S(C)(=O)=Nc1nc(-c2ccccn2)cs1] | E | Tan solid, mp = 134-141° C. 1:1 mixture of two diastereomers; $^1$H NMR (400 MHz, CDCl$_3$) δ 8.85 (s, 1H), 8.79 (s, 1H), 8.60 (s, 2H), 8.12 (dd, 2H), 7.95 (dd, 2H), 7.73-7.79 (m, 4H), 7.57 (d, 2H), 7.20 (m, 2H), 5.27 (q, 1H), 5.20 (m, 1H), 3.29 (s, 3H), 3.19 (s, 3H), 2.00 (d, 3H), 1.94 (d, 3H); LC-MS (ESI): Mass calcd for C$_{17}$H$_{16}$F$_3$N$_4$OS$_2$ [M + H]$^+$, 413. Found 413. |
| 36 | 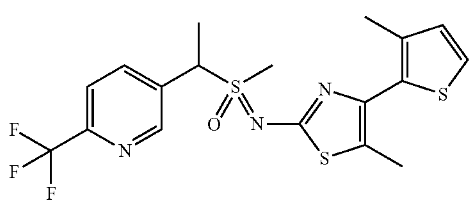 [SMILES: Cc1ccsc1-c1nc(N=S(C)(=O)C(C)c2ccc(C(F)(F)F)nc2)sc1C] | E | Yellow oil. 1:1 mixture of two diastereomers; $^1$H NMR (400 MHz, CDCl$_3$) δ 8.80 (s, 1H), 8.72 (s, 1H), 8.11 (d, 1H), 8.06 (d, 1H), 7.73 (dd, 2H), 7.23 (m, 2H), 6.90 (m, 2H), 5.42 (q, 1H), 5.31 (q, 1H), 3.24 (s, 3H), 3.07 (s, 3H), 2.31 (s, 3H), 2.278 (s, 3H), 2.275 (s, 3H), 2.26 (s, 3H), 1.94 (d, 3H), 1.87 (d, 3H); LC-MS (ESI): Mass calcd for C$_{18}$H$_{19}$F$_3$N$_3$OS$_3$ [M + H]$^+$, 446. Found 446. |
| 37 | 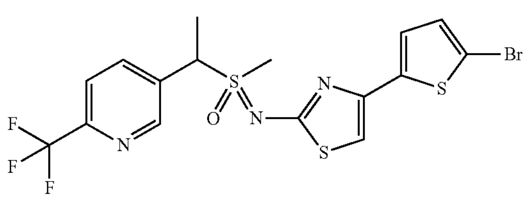 [SMILES: CC(c1ccc(C(F)(F)F)nc1)S(C)(=O)=Nc1nc(-c2ccc(Br)s2)cs1] | E | White solid, mp = 160-165° C. 1:1 mixture of two diastereomers; $^1$H NMR (400 MHz, CDCl$_3$) δ 8.86 (s, 1H), 8.74 (s, 1H), 8.13 (d, 1H), 8.07 (d, 1H), 7.79 (d, 1H), 7.74 (d, 1H), 7.07 (m, 2H), 6.97-7.00 (m, 2H), 6.77 (s, 1H), 6.74 (s, 1H), 5.40 (q, 1H), 5.25 (q, 1H), 3.31 (s, 3H), 3.13 (s, 3H), 1.99 (d, 3H), 1.80 (d, 3H); LC-MS (ESI): Mass calcd for C$_{16}$H$_{13}$BrF$_3$N$_3$OS$_3$ [M]$^+$, 496. Found 496. |

TABLE 3-continued

Compounds

| Cmpd # | Structure | Route | Characterization |
|---|---|---|---|
| 38 | 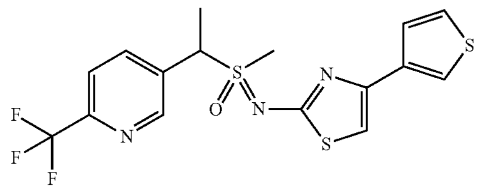 [SMILES: CC(c1ccc(C(F)(F)F)nc1)S(C)(=O)=Nc1nc(-c2ccsc2)cs1] | E | White solid, mp = 168-173° C. 1:1 mixture of two diastereomers; $^1$H NMR (400 MHz, CDCl$_3$) δ 8.83 (s, 1H), 8.76 (s, 1H), 8.12 (d, 1H), 8.09 (d, 1H), 7.78 (d, 1H), 7.73 (d, 1H), 7.62 (m, 2H), 7.39 (m, 2H), 7.31-7.35 (m, 2H), 6.79 (s, 1H), 6.77 (s, 1H), 5.33 (q, 1H), 5.20 (q, 1H), 3.27 (s, 3H), 3.15 (s, 3H), 1.99 (d, 3H), 1.92 (d, 3H); LC-MS (ESI): Mass calcd for C$_{16}$H$_{14}$F$_3$N$_3$OS$_3$ [M]$^+$, 417. Found 417. |
| 39 | 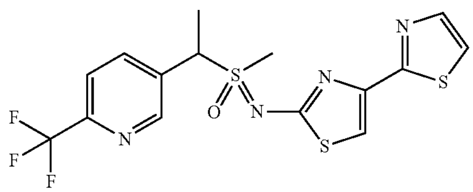 [SMILES: CC(c1ccc(C(F)(F)F)nc1)S(C)(=O)=Nc1nc(-c2nccs2)cs1] | E | Tan solid, mp = 163-167° C. 1:1 mixture of two diastereomers; $^1$H NMR (400 MHz, CDCl$_3$) δ 8.88 (s, 1H), 8.79 (s, 1H), 8.15 (d, 1H), 8.09 (d, 1H), 7.81 (m, 2H), 7.75 (d, 2H), 7.43 (s, 1H), 7.41 (s, 1H), 7.32 (d, 1H), 7.29 (d, 1H), 5.41 (q, 1H), 5.23 (q, 1H), 3.28 (s, 3H), 3.16 (s, 3H), 2.00 (d, 3H), 1.91 (d, 3H); LC-MS (ESI): Mass calcd for C$_{15}$H$_{14}$F$_3$N$_4$OS$_3$ [M + H]$^+$, 419. Found 419. |
| 40 | 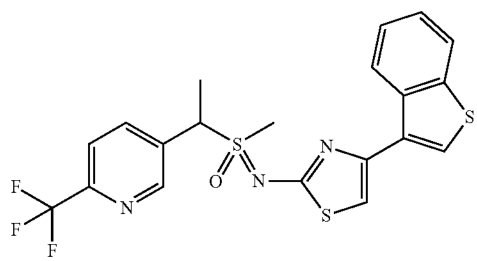 [SMILES: CC(c1ccc(C(F)(F)F)nc1)S(C)(=O)=Nc1nc(-c2csc3ccccc23)cs1] | E | Yellow oil. 1:1 mixture of two diastereomers; $^1$H NMR (400 MHz, CDCl$_3$) δ 8.82 (d, 1H), 8.79 (s, 1H), 8.30 (dd, 2H), 8.11 (dd, 2H), 7.90 (dd, 2H), 7.73-7.78 (m, 4H), 7.37-7.46 (m, 4H), 6.99 (s, 1H), 6.97 (s, 1H), 5.32 (q, 1H), 5.24 (q, 1H), 3.27 (s, 3H), 3.18 (s, 3H), 1.99 (d, 3H), 1.95 (d, 3H); LC-MS (ESI): Mass calcd for C$_{20}$H$_{17}$F$_3$N$_3$OS$_3$ [M + H]$^+$, 468. Found 468. |
| 41 | 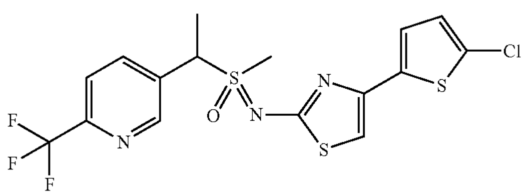 [SMILES: CC(c1ccc(C(F)(F)F)nc1)S(C)(=O)=Nc1nc(-c2ccc(Cl)s2)cs1] | E | Tan solid, mp = 124-128° C. 1:1 mixture of two diastereomers; $^1$H NMR (400 MHz, CDCl$_3$) δ 8.88 (s, 1H), 8.77 (s, 1H), 8.15 (dd, 1H), 8.09 (dd, 1H), 7.81 (d, 1H), 7.75 (d, 1H), 7.10 (dd, 2H), 6.87 (d, 1H), 6.85 (d, 1H), 6.78 (s, 1H), 6.75 (s, 1H), 5.42 (q, 1H), 5.27 (s, 1H), 3.29 (s, 3H), 3.15 (s, 3H), 2.01 (d, 3H), 1.91 (d, 3H); LC-MS (ESI): Mass calcd for C$_{16}$H$_{14}$ClF$_3$N$_3$OS$_3$ [M + H]$^+$, 452. Found 452. |
| 42 | 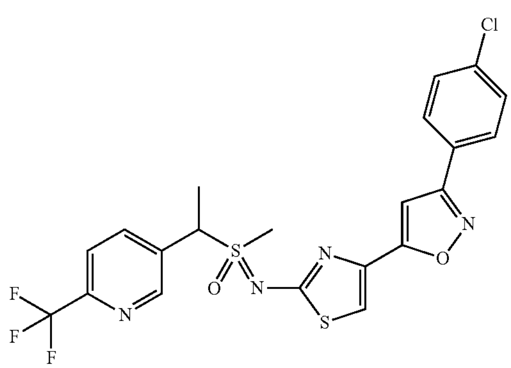 [SMILES: CC(c1ccc(C(F)(F)F)nc1)S(C)(=O)=Nc1nc(-c2cc(-c3ccc(Cl)cc3)no2)cs1] | E | Yellow oil. 1:1 mixture of two diastereomers; $^1$H NMR (400 MHz, CDCl$_3$) δ 8.84 (s, 1H), 8.80 (s, 1H), 8.12 (s, 1H), 8.10 (s, 1H), 7.75-7.81 (m, 6H), 7.44-7.46 (m, 4H), 7.31 (d, 2H), 6.80 (s, 2H), 5.13 (q, 1H), 5.05 (q, 1H), 3.29 (s, 3H), 3.19 (s, 3H), 2.00 (d, 3H), 1.97 (d, 3H); LC-MS (ESI): Mass calcd for C$_{21}$H$_{17}$ClF$_3$N$_4$O$_2$S$_2$ [M + H]$^+$, 513. Found 513. |

TABLE 3-continued

Compounds

| Cmpd # | Structure | Route | Characterization |
|---|---|---|---|
| 43 | 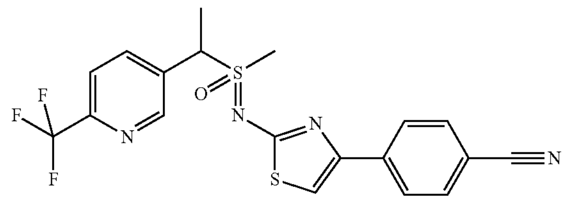 [SMILES: CC(c1ccc(C(F)(F)F)nc1)S(C)(=O)=Nc1nc(-c2ccc(C#N)cc2)cs1] | E | 1:1 mixture of two diastereomers $^1$H NMR (400 MHz, CDCl$_3$) δ 8.84 (d, 1H), 8.79 (d, 1H), 8.11 (m, 2H), 7.90 (m, 4H), 7.77 (m, 2H), 7.65 (m, 4H), 7.10 (s, 1H), 7.08 (s, 1H), 5.15 (m, 1H), 5.07 (m, 1H), 3.29 (s, 3H), 3.19 (s, 3H), 2.0 (d, 3H), 1.96 (d, 3H); Mass calcd for C$_{19}$H$_{15}$F$_3$N$_4$OS$_2$ [M + H]$^+$, 437, Found 437. Mp = 78-80° C. |
| 44 | 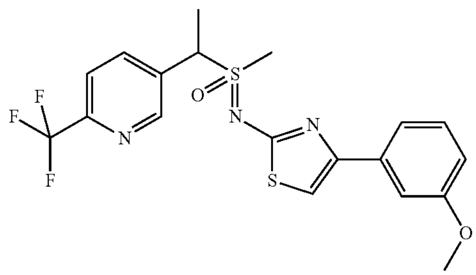 [SMILES: COc1cccc(-c2csc(N=S(C)(=O)C(C)c3ccc(C(F)(F)F)nc3)n2)c1] | E | 3:2 mixture of two diastereomers $^1$H NMR (400 MHz, CDCl$_3$) δ 8.84 (d, 1H), 8.76 (d, 1H), 8.10 (m, 2H), 7.77 (d, 1H), 7.73 (d, 1H), 7.84 (m, 6H), 6.95 (s, 1H), 6.92 (s, 1H), 6.86 (m, 2H), 5.85 (m, 1H), 5.23 (m, 1H), 3.86 (s, 3H), 3.86 (s, 3H), 3.28 (s, 3H), 3.15 (s, 3H), 1.98 (d, 3H), 1.90 (d, 3H); Mass calcd for C$_{19}$H$_{18}$F$_3$N$_3$O$_2$S$_2$ [M + H]$^+$, 442, Found 442. Mp = 107-110° C. |
| 45 | 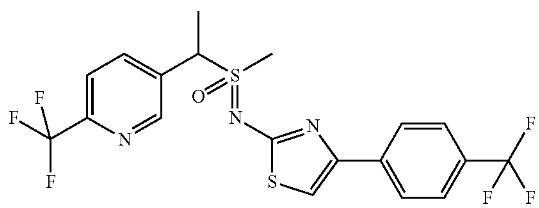 [SMILES: CC(c1ccc(C(F)(F)F)nc1)S(C)(=O)=Nc1nc(-c2ccc(C(F)(F)F)cc2)cs1] | E | 1:1 mixture of two diastereomers $^1$H NMR (400 MHz, CDCl$_3$) δ 8.83 (d, 1H), 8.78 (d, 1H), 8.11 (m, 2H), 7.91 (m, 4H), 7.75 (m, 2H), 7.63 (m, 4H), 7.06 (s, 1H), 7.03 (s, 1H), 5.22 (m, 1H), 5.12 (m, 1H), 3.29 (s, 3H), 3.18 (m, 3H), 1.99 (d, 3H), 1.95 (d, 3H); Mass calcd for C$_{19}$H$_{15}$F$_6$N$_3$OS$_2$ [M + H]$^+$, 480, Found 480. Mp = 124-127° C. |
| 46 | 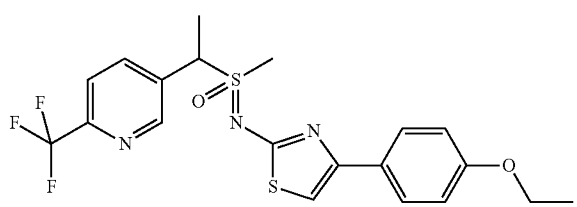 [SMILES: CCOc1ccc(-c2csc(N=S(C)(=O)C(C)c3ccc(C(F)(F)F)nc3)n2)cc1] | E | 1:1 mixture of two diastereomers $^1$H NMR (400 MHz, CDCl$_3$) δ 8.83 (d, 1H), 8.77 (d, 1H), 8.13 (dd, 1H), 8.09 (dd, 1H), 7.75 (m, 6H), 6.91 (m, 4H), 6.80 (s, 1H), 6.77 (s, 1H), 5.87 (m, 1H), 5.24 (m, 1H), 4.07 (m, 4H), 3.27 (s, 3H), 3.15 (s, 3H), 1.98 (d, 3H), 1.90 (d, 3H), 1.41 (m, 6H); Mass calcd for C$_{20}$H$_{20}$F$_3$N$_3$O$_2$S$_2$ [M + H]$^+$, 456, Found 456. Mp = 105-110° C. |
| 47 | 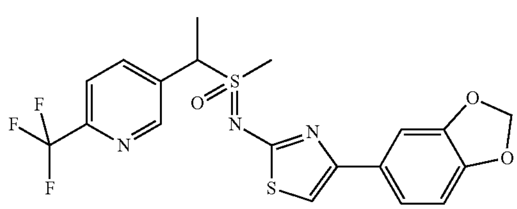 [SMILES: CC(c1ccc(C(F)(F)F)nc1)S(C)(=O)=Nc1nc(-c2ccc3c(c2)OCO3)cs1] | E | 1:1 mixture of two diastereomers $^1$H NMR (400 MHz, CDCl$_3$) δ 8.83 (d, 1H), 8.76 (d, 1H), 8.10 (m, 2H), 7.75 (m, 2H), 7.61 (m, 4H), 6.83 (m, 2H), 6.78 (s, 1H), 6.76 (s, 1H), 5.99 (s, 2H), 5.98 (s, 2H), 5.81 (m, 1H), 5.20 (m, 1H), 3.27 (s, 3H), 3.15 (s, 3H), 1.98 (d, 3H), 1.91 (d, 3H); Mass calcd for C$_{19}$H$_{16}$F$_3$N$_3$O$_3$S$_2$ [M + H]$^+$, 456, Found 456. |

TABLE 3-continued

Compounds

| Cmpd # | Structure | Route | Characterization |
|---|---|---|---|
| 48 | 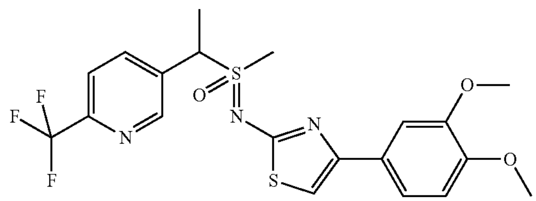 [SMILES: COc1ccc(-c2csc(N=S(C)(=O)C(C)c3ccc(C(F)(F)F)nc3)n2)cc1OC] | E | 1:1 mixture of two diastereomers $^1$H NMR (400 MHz, CDCl$_3$) δ 8.83 (d, 1H), 8.78 (d, 1H), 8.12 (m, 2H), 7.75 (m, 2H), 7.40 (m, 2H), 7.84 (s, 2H), 6.90 (m, 2H), 6.82 (s, 1H), 6.79 (s, 1H), 5.29 (m, 1H), 5.18 (m, 1H), 3.95 (s, 3H), 3.94 (s, 3H), 3.92 (s, 3H), 3.91 (s, 3H), 3.26 (s, 3H), 3.16 (s, 3H), 1.98 (d, 3H), 1.92 (d, 3H); Mass calcd for C$_{20}$H$_{20}$F$_3$N$_3$O$_3$S$_2$ [M + H]$^+$, 472, Found 472. Mp = 153-160. |
| 49 | 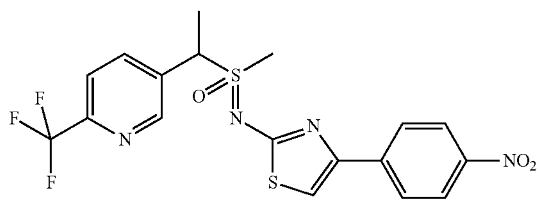 [SMILES: CC(c1ccc(C(F)(F)F)nc1)S(C)(=O)=Nc1nc(-c2ccc([N+](=O)[O-])cc2)cs1] | E | 1:1 mixture of two diastereomers $^1$H NMR (400 MHz, CDCl$_3$) δ 8.84 (d, 1H), 8.80 (d, 1H), 8.24 (m, 4H), 8.12 (m, 2H), 7.95 (m, 4H), 7.77 (m, 2H), 7.17 (s, 1H), 7.14 (s, 1H), 5.14 (m, 1H), 5.06 (m, 1H), 3.30 (s, 3H), 3.20 (s, 3H), 2.01 (d, 3H), 1.98 (d, 3H); Mass calcd for C$_{18}$H$_{15}$F$_3$N$_4$O$_3$S$_2$ [M + H]$^+$, 457, Found 457. |
| 50 | 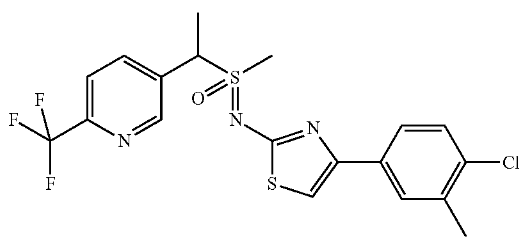 [SMILES: Cc1cc(-c2csc(N=S(C)(=O)C(C)c3ccc(C(F)(F)F)nc3)n2)ccc1Cl] | E | 1:1 mixture of two diastereomers $^1$H NMR (400 MHz, CDCl$_3$) δ 8.83 (d, 1H), 8.78 (d, 1H), 8.10 (m, 2H), 7.75 (m, 2H), 7.67 (m, 2H), 7.66 (m, 2H), 7.83 (m, 2H), 6.91 (s, 1H), 6.89 (s, 1H), 5.24 (m, 1H), 5.13 (m, 1H), 3.27 (s, 3H), 3.16 (s, 3H), 2.11 (m, 6H), 1.98 (d, 3H), 1.93 (d, 3H); Mass calcd for C$_{19}$H$_{17}$ClF$_3$N$_3$OS$_2$ [M + H]$^+$, 460, Found 460. |
| 51 | 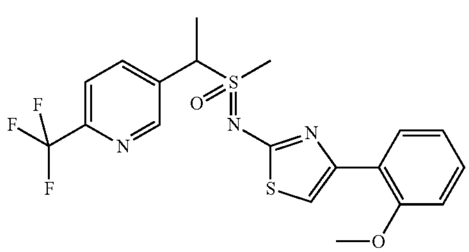 [SMILES: COc1ccccc1-c1csc(N=S(C)(=O)C(C)c2ccc(C(F)(F)F)nc2)n1] | E | 1:1 mixture of two diastereomers $^1$H NMR (400 MHz, CDCl$_3$) δ 8.83 (d, 1H), 8.76 (d, 1H), 8.10 (m, 4H), 7.75 (m, 2H), 7.42 (s, 1H), 7.40 (s, 1H), 7.30 (m, 2H), 7.00 (m, 4H), 5.13 (m, 1H), 5.29 (m, 1H), 3.95 (s, 3H), 3.94 (s, 3H), 3.27 (s, 3H), 3.14 (s, 3H), 1.97 (d, 3H), 1.89 (d, 3H); Mass calcd for C$_{19}$H$_{18}$F$_3$N$_3$O$_2$S$_2$ [M + H]$^+$, 442, Found 442. Mp = 72-77° C. |
| 52 | 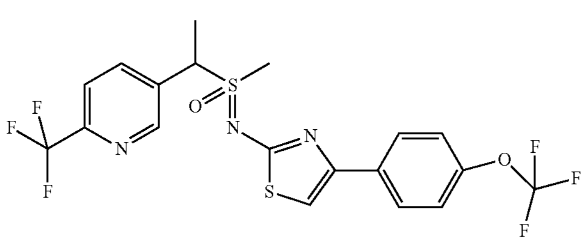 [SMILES: CC(c1ccc(C(F)(F)F)nc1)S(C)(=O)=Nc1nc(-c2ccc(OC(F)(F)F)cc2)cs1] | E | 1:1 mixture of two diastereomers $^1$H NMR (400 MHz, CDCl$_3$) δ 8.83 (d, 1H), 8.78 (d, 1H), 8.11 (m 2H), 7.79 (m, 6H), 7.23 (m, 4H), 6.94 (s, 1H), 6.91 (s, 1H), 5.25 (m, 1H), 5.14 (m, 1H), 3.28 (s, 3H), 3.16 (s, 3H), 1.99 (d, 3H), 1.94 (d, 3H); Mass calcd for C$_{19}$H$_{15}$F$_6$N$_3$O$_2$S$_2$ [M + H]$^+$, 496, Found 496. Mp = 90-95° C. |

| Cmpd # | Structure | Route | Characterization |
|---|---|---|---|
| 53 | 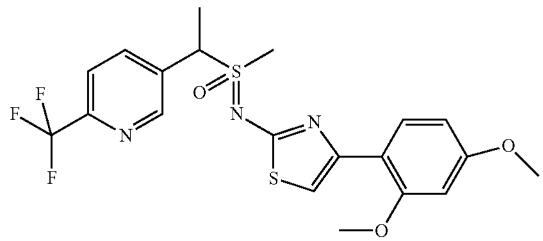 [SMILES: COc1ccc(-c2csc(N=S(C)(=O)C(C)c3ccc(C(F)(F)F)nc3)n2)c(OC)c1] | E | 1:1 mixture of two diastereomers $^1$H NMR (400 MHz, CDCl$_3$) δ 8.83 (d, 1H), 8.77 (d, 1H), 8.11 (m, 2H), 8.01 (m, 2H), 7.77 (d, 1H), 7.72 (d, 1H), 7.24 (m, 2H), 6.55 (m, 4H), 5.42 (m, 1H), 5.27 (m, 1H), 3.92 (s, 3H), 3.91 (s, 3H), 3.86 (s, 3H), 3.84 (s, 3H), 3.26 (s, 3H), 3.13 (s, 3H), 1.96 (d, 3H), 1.89 (d, 3H); Mass calcd for C$_{20}$H$_{20}$F$_3$N$_3$O$_3$S$_2$ [M + H]$^+$, 472, Found 472. |

E = route used in example VIII.

Example IX

Preparation of 5-{[methyl[4-(4-methoxyphenyl)-1,3-thiazol-2-yl]sulfonimidoyl]methyl}-2-(trifluoromethyl)pyridine (54)

(54)

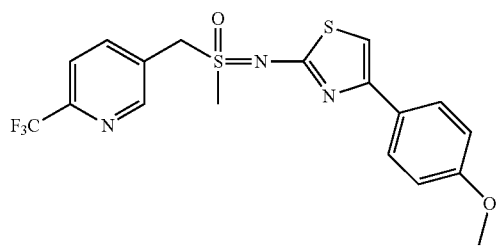

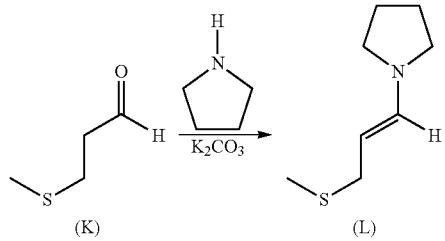

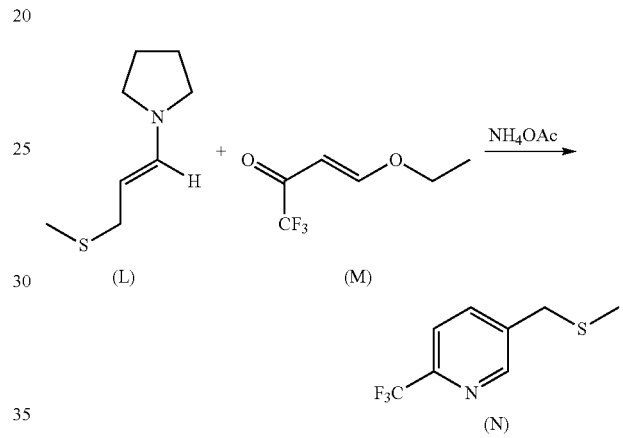

To a dry 1 L round bottom flask equipped with a magnetic stir bar, liquid addition funnel, thermometer, and nitrogen inlet were added potassium carbonate (33.2 g, 240 mmol) and pyrrolidine (136.5 g, 160 mL, 1.92 mol), and the resulting suspension was cooled to 0° C. in an ice bath. 3-(Methylthio) propionaldehyde (K) (50 g, 480 mmol) was added dropwise via the addition funnel at a rate which maintained the reaction temperature at 0-7° C. The resulting light yellow mixture was warmed to room temperature and stirred for 16 hours. The residual potassium carbonate was removed by filtration, the filter cake washed with Et$_2$O, and the filtrate concentrated on the rotary evaporator to give the crude enamine as a viscous, light yellow oil. Fractional distillation (108-110° C. at 4 mm Hg) afforded 63.3 g (83.8%) of 1-[3-(methylthio)prop-1-enyl]pyrrolidine (L) as a colorless liquid. $^1$H NMR (CDCl$_3$) δ 6.29 (d, 1H), 4.06 (dt, 1H), 3.16 (d, 2H), 3.03 (m, 4H), 2.04 (s, 3H), 1.85 (m, 4H). GC-MS (EI) m/z 157 (M$^+$).

To a dry 1 L round bottom flask equipped with a magnetic stir bar, liquid addition funnel, thermometer, and nitrogen inlet were added 4-ethoxy-1,1,1-trifluorobut-3-en-2-one (M) (67.4 g, 401 mmol) and 133 mL of anhydrous acetonitrile, and the resulting solution was cooled to 0° C. in an ice bath. To this solution was added 1-[3-(methylthio)prop-1-enyl] pyrrolidine (L) (63.0 g, 401 mmol, dissolved in 50 mL of anhydrous acetonitrile) dropwise via the addition funnel at a rate which maintained the reaction temperature at 0-7° C. The ice bath was removed and the resulting burgundy solution was warmed to room temperature and stirred for 2 hours. Ammonium acetate (46.3 g, 601 mmol) was added and the reaction was heated to reflux and stirred for 5 hours, and then stirred at room temperature for 16 hours. The acetonitrile was evaporated on the rotary evaporator and the residue was dissolved in 1 L of Et$_2$O, washed with water (3×200 mL), dried (Na$_2$SO$_4$), filtered, and the Et$_2$O removed on the rotary evaporator to give 83.4 g of the crude pyridine as a dark-red oil. Flash chromatography (SiO$_2$, 25→70% EtOAc/Hexanes) afforded 70.8 g (85%) of 5-[(methylthio)methyl]-2-(trifluoromethyl) pyridine (N) as an orange oil. $^1$H NMR (CDCl$_3$) δ 8.64 (d, 1H), 7.86 (dd, 1H), 7.66 (d, 1H), 3.73 (s, 2H), 2.02 (s, 3H). GC-MS (EI) m/z 207 (M$^+$).

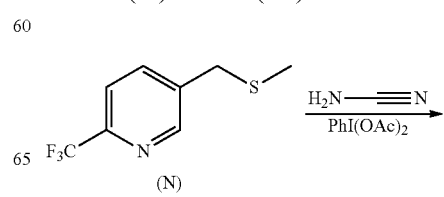

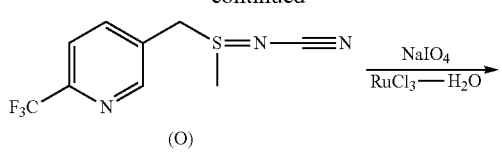

(O)

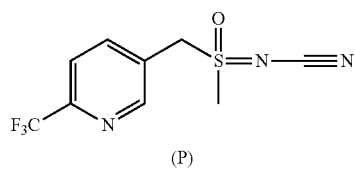

(P)

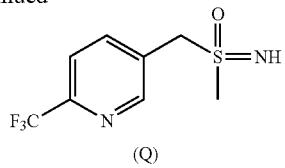

(Q)

Compound (Q) was synthesized according to the procedure described in Example VIII. Isolated as a white solid. Mp=108-110° C. ¹H NMR (DMSO-d₆) δ 8.76 (d, 1H), 8.13 (dd, 1H), 7.96 (d, 1H), 4.58 (q, 2H), 3.92 (s, 1H), 2.85 (s, 3H). LC-MS (ESI) m/z 239 [M+H]⁺, m/z 237 [M−H]⁻.

To a dry 1 L round bottom flask equipped with a magnetic stir bar and nitrogen inlet were added 5-[(methylthio)methyl]-2-(trifluoromethyl)pyridine (N) (50.0 g, 241 mmol), cyanamide (10.1 g, 241 mmol), and 500 mL of anhydrous acetonitrile, and the resulting solution was cooled to 0° C. in an ice bath. Iodobenzene diacetate (77.7 g, 241 mmol) was added in one portion, and the resulting yellow-orange mixture was warmed to room temperature and stirred for 16 hours. The reaction was washed with hexanes (4×200 mL) and then concentrated on the rotary evaporator to give 78.3 g of the crude sulfilimine as an orange oil. The oil was washed with warm hexanes (55° C.), and then dissolved in CH₂Cl₂ (650 mL). The resulting orange precipitate was removed by vacuum filtration, and the filtrate was concentrated on the rotary evaporator to give sulfilimine (O) as an orange oil, which was used without further purification.

The sulfilimine intermediate (O) (59.6 g, 241 mmol) was dissolved in 250 mL of CH₂Cl₂ and added dropwise to a 2 L round bottom flask equipped with a magnetic stir bar, liquid addition funnel, thermometer, and nitrogen inlet that had been previously charged with sodium periodate (77.3 g, 362 mmol), water (500 mL), CH₂Cl₂ (500 mL), and ruthenium chloride-H₂O (1.36 g, 6.0 mmol). The two phase system was stirred vigorously for 16 hours at room temperature, and then the resulting light brown mixture was filtered through a Buchner funnel. The filtrate was transferred to a separatory funnel and the phases separated. The aqueous was extracted with CH₂Cl₂ (2×200 mL), and the combined organic extracts were washed with water (2×250 mL), dried (Na₂SO₄), and filtered. The dark solution was treated with neutral alumina (150 g) and stirred at room temperature for 15 minutes. The alumina was removed by filtration and the resulting colorless solution was concentrated on the rotary evaporator to give the crude product as a sticky, light-yellow solid. Triturating with Et₂O afforded 13.1 g (21%) of methyl(oxido){[6-(trifluoromethyl)pyridin-3-yl]methyl}-λ⁴-sulfanylidenecyanamide (P) as a granular white solid. Mp=137-140° C. ¹H NMR (DMSO-d₆) δ 8.83 (s, 1H), 8.20 (dd, 1H), 8.05 (d, 1H), 5.27 (s, 2H), 3.49 (s, 3H). LC-MS (ESI) m/z 264 [M+H]⁺, m/z 262 [M−H]⁻.

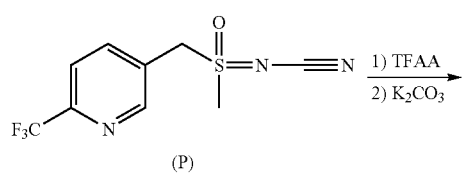

(P)

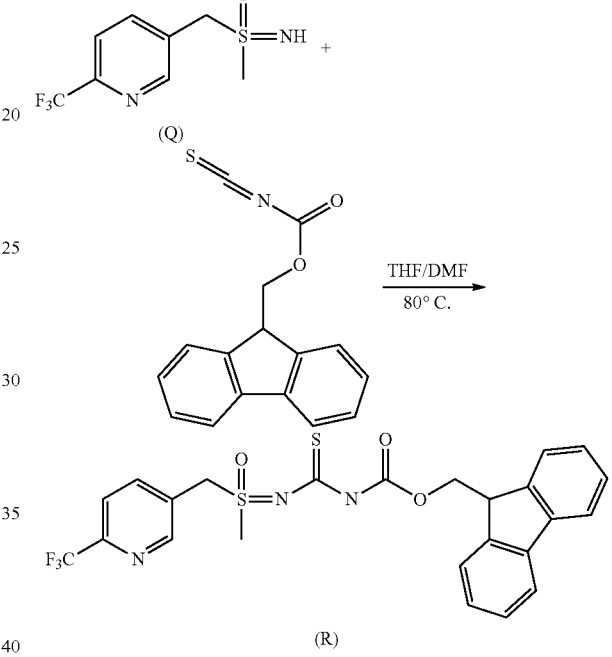

(R)

Compound (R) was synthesized according to the procedure described in Example VIII. Isolated as light yellow foam. Mp=92-97° C. ¹H NMR (DMSO-d₆) δ 11.18 (s, 1H), 8.93 (s, 1H), 8.29 (d, 1H), 7.98 (d, 1H), 7.91 (d, 2H), 7.83 (d, 2H), 7.43 (t, 2H), 7.34 (dt, 2H), 5.21 (d, 2H), 4.33-4.24 (m, 3H), 3.66 (s, 3H). LC-MS (ESI) m/z 520 [M+H]⁺, m/z 518 [M−H]⁻.

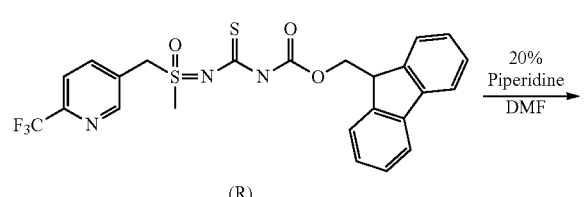

(R)

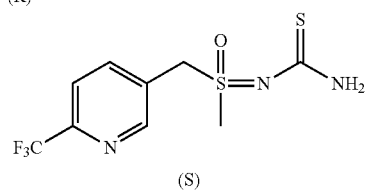

(S)

Compound (S) was synthesized according to the procedure described in Example VIII. Isolated as a white solid.

Mp=107-109° C. ¹H NMR (CDCl₃) δ 8.82 (s, 1H), 8.11 (d, 1H), 7.76 (d, 1H), 6.36 (bs, 1H), 6.19 (bs, 1H), 5.52 (d, 1H), 5.06 (d, 1H), 3.39 (s, 3H). LC-MS (ESI) m/z 298 [M+H]⁺, m/z 296 [M−H]⁻.

5-{[Methyl[4-(4-methoxyphenyl)-1,3-thiazol-2-yl]sulfonimidoyl]methyl}-2-(trifluoromethyl)pyridine (54) was synthesized according to the procedure described in Example VIII. Isolated as a foamy white solid. Mp=158-161° C. ¹H NMR (CDCl₃) δ 8.73 (d, 1H), 7.99 (dd, 1H), 7.76 (d, 2H), 7.74 (d, 1H), 6.92 (dd, 2H), 6.83 (s, 1H), 5.09 (d, 1H), 5.01 (d, 1H), 3.84 (s, 3H), 3.24 (s, 3H). LC-MS (ESI) m/z 428 [M+H]⁺, m/z 426 [M−H]⁻.

Example X

Preparation of 5-{[methyl[4-(4-methoxyphenyl)-1,3-thiazol-2-yl]sulfonimidoyl]methyl}-2-chloropyridine (57)

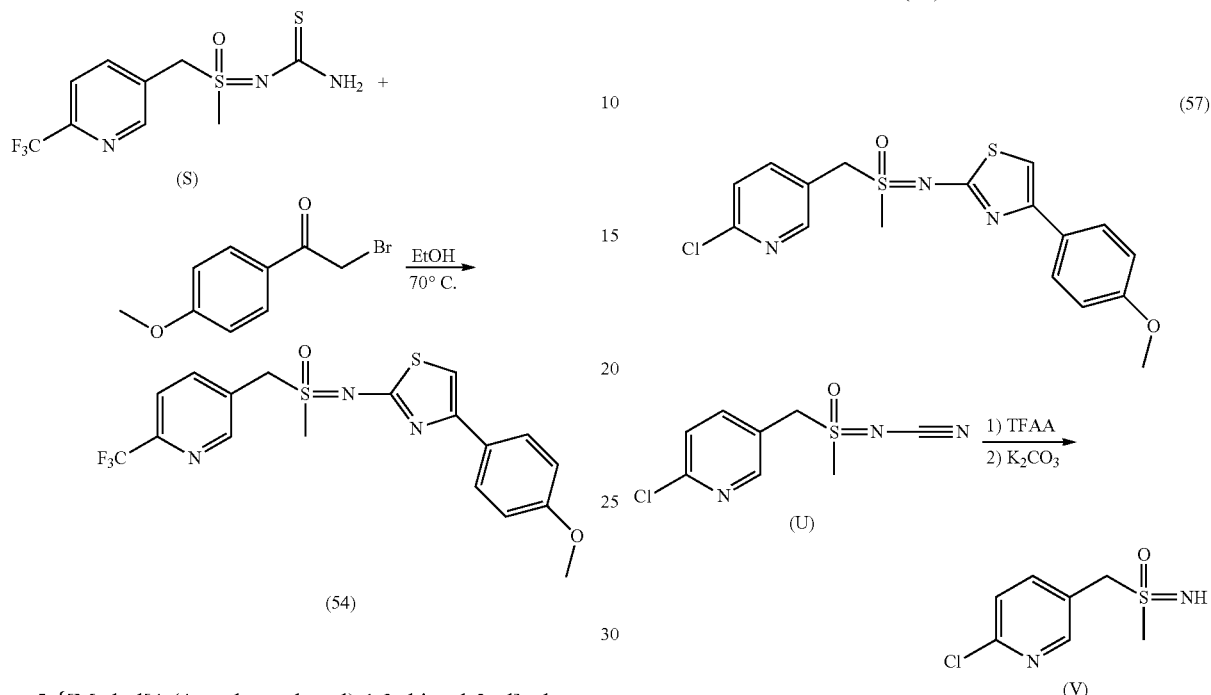

Compound (V) was synthesized according to the procedure described in Example VIII. Isolated as a white solid. Mp=132-135° C. ¹H NMR (DMSO-d₆) δ 8.43 (d, 1H), 7.90 (dd, 1H), 7.56 (d, 1H), 4.48 (d, 1H), 4.41 (d, 1H), 3.83 (s, 1H), 2.81 (s, 3H). LC-MS (ESI) m/z 203 [M−H]⁻.

TABLE 4

| Cmpd # | Structure | Route | Characterization |
|---|---|---|---|
| 55 | 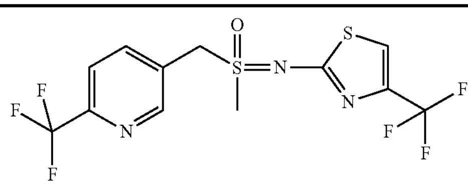 | F | White Foam. MP 126-128° C. ¹H NMR (CDCl₃) δ 8.70 (d, 1H), 7.98 (dd, 1H), 7.75 (d, 1H), 7.19 (d, 1H), 5.06 (d, 1H), 4.88 (d, 1H), 3.26 (s, 3H). LC-MS (ESI) m/z 390 [M + H]⁺, m/z 388 [M − H]⁻. |
| 56 | 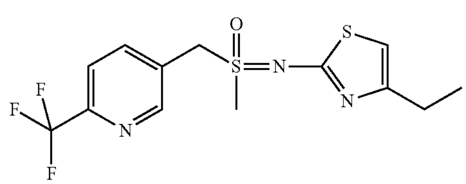 [SMILES: CCc1csc(N=S(C)(=O)Cc2ccc(C(F)(F)F)nc2)n1] | F | White solid. MP 114-116° C. ¹H NMR (CDCl₃) δ 8.82 (s, 1H), 8.20 (dd, 1H), 8.02 (d, 1H), 6.75 (s, 1H), 5.44 (s, 2H), 3.68 (s, 3H), 2.56 (q, 2H), 1.16 (s, 3H). LC-MS (ESI) m/z 350 [M + H]⁺, m/z 348 [M − H]⁻. |

F = route used in example IX.

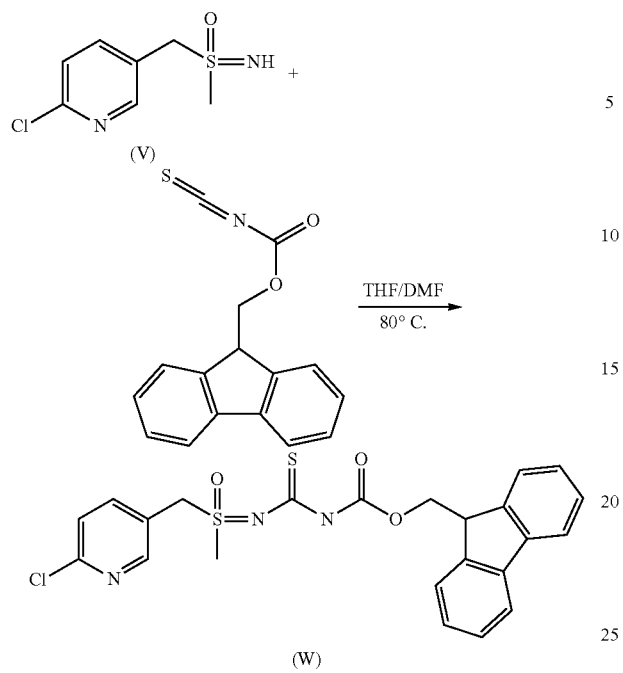

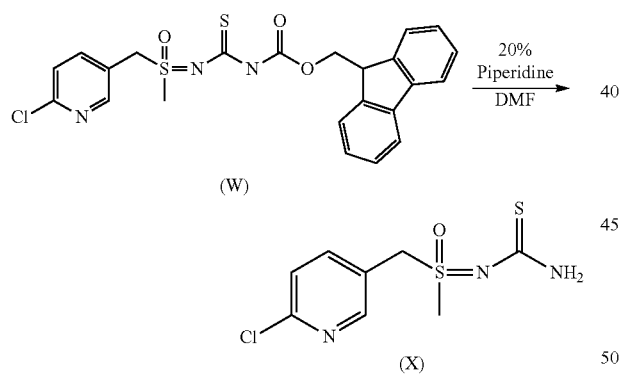

Compound (W) was synthesized according to the procedure described in Example VIII. Isolated as a light yellow foam. Mp=98-101° C. ¹H NMR (DMSO-d₆) δ 11.15 (s, 1H), 8.56 (d, 1H), 8.05 (dd, 1H), 7.90 (d, 2H), 7.84 (d, 2H), 7.59 (d, 1H), 7.44 (t, 2H), 7.34 (dt, 2H), 5.09 (s, 2H), 4.32-4.26 (m, 3H), 3.61 (s, 3H). LC-MS (ESI) m/z 486 [M+H]⁺, m/z 484 [M–H]⁻.

Compound (X) was synthesized according to the procedure described in Example VIII. Isolated as a light orange solid. Mp=155-158° C. ¹H NMR (DMSO-d₆) δ 8.51 (d, 1H), 8.12 (bs, 1H), 7.99 (d, 1H), 7.96 (d, 1H), 7.61 (d, 1H), 5.21 (s, 2H), 3.36 (s, 3H). LC-MS (ESI) m/z 264 [M+H]⁺, m/z 262 [M–H]⁻.

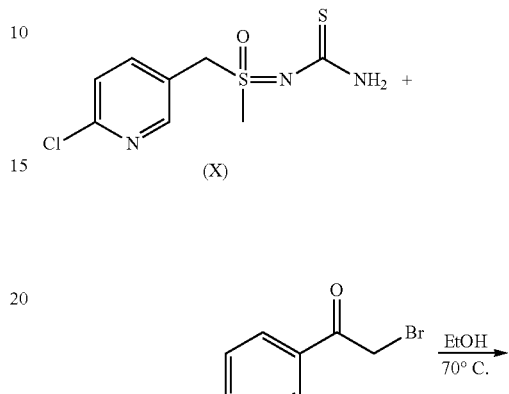

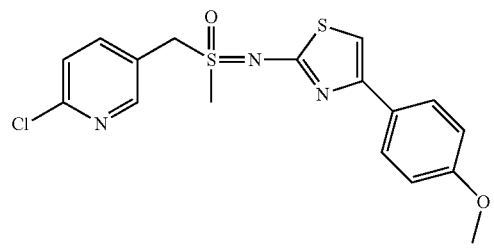

(57)

5-{[Methyl[4-(4-methoxyphenyl)-1,3-thiazol-2-yl]sulfonimidoyl]methyl}-2chloropyridine (57) was synthesized according to the procedure described in Example VIII. Isolated as a pale yellow solid. Mp=160-163° C. ¹H NMR (CDCl₃) δ 8.39 (d, 1H), 7.78-74 (m, 3H), 7.38 (d, 1H), 6.92 (d, 2H), 6.82 (s, 1H), 4.94 (s, 2H), 3.84 (s, 3H), 3.21 (s, 3H). LC-MS (ESI) m/z 394 [M+H]⁺, m/z 392 [M–H]⁻.

TABLE 5

Compounds

| Cmpd # | Structure | Route | Characterization |
|---|---|---|---|
| 58 | 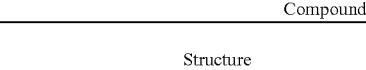 | G | Pale yellow solid. MP 122-125° C. ¹H NMR (CDCl₃) δ 8.36 (d, 1H), 7.74 (dd, 1H), 7.39 (d, 1H), 7.17 (d, 1H), 4.92 (d, 1H), 4.80 (d, 1H), 3.22 (s, 3H). LC-MS (ESI) m/z 356 [M + H]⁺, m/z 354 [M – H]⁻. |

TABLE 5-continued

Compounds

| Cmpd # | Structure | Route | Characterization |
|---|---|---|---|
| 59 | 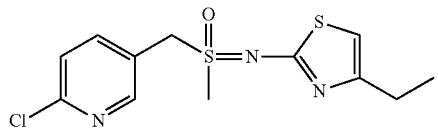 [SMILES: CCc1csc(N=S(C)(=O)Cc2ccc(Cl)nc2)n1] | G | White foam. MP 114-116° C. $^1$H NMR (CDCl$_3$) δ 8.36 (d, 1H), 7.74 (dd, 1H), 7.38 (d, 1H), 6.31 (d, 1H), 4.88 (s, 2H), 3.14 (s, 3H), 2.63 (dq, 2H), 1.25 (s, 3H). LC-MS (ESI) m/z 316 [M + H]$^+$, m/z 314 [M − H]$^−$. |

G = route used in example X.

Example XI

Preparation of 5-{1-[methyl(4-(4-methoxyphenyl)-1,3-thiazol-2-yl)sulfonimidoyl]pentyl}-2-(trifluoromethyl)pyridine (60)

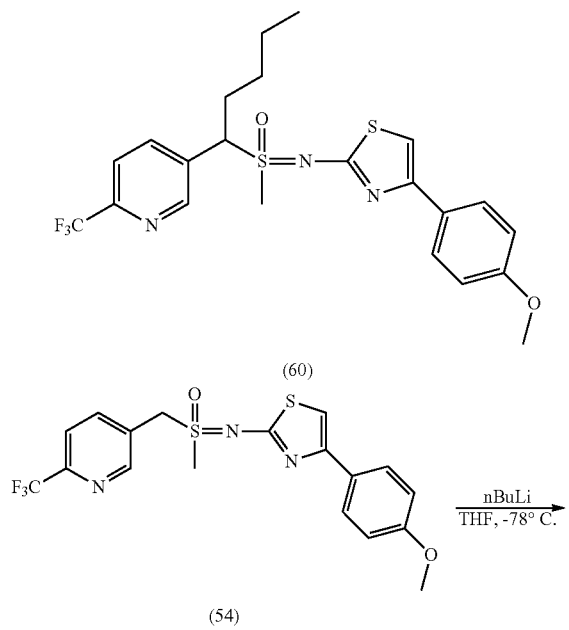

To a magnetically stirred solution of 5-{[methyl[4-(4-methoxyphenyl)-1,3-thiazol-2-yl]sulfonimidoyl]methyl}-2-(trifluoromethyl)pyridine (54) (0.125 g, 0.29 mmol) in anhydrous THF (2 mL) was added n-BuLi (0.13 mL of 2.5 M in hexanes, 0.32 mmol) at −78° C., and the resulting orange solution was stirred at −78° C. for 20 minutes. Iodomethane (0.046 g, 0.32 mmol) was added and the reaction was warmed to room temperature. LC-MS analysis indicated only 13% of the desired mono-methyl intermediate had formed. The reaction was cooled to −78° C., and a second portion of n-BuLi (0.13 mL of 2.5 M in hexanes, 0.32 mmol) was added, and the reaction was stirred for 20 minutes. A second portion of iodomethane (0.046 g, 0.32 mmol) was added and the reaction was warmed to room temperature. LC-MS indicated 65% of the desired mono-methyl had formed along with 35% of the mono-butyl, which arose from the generation of butyl iodide via the reaction of n-BuLi with iodomethane. The reaction was quenched with aqueous ammonium chloride, extracted with EtOAc (2×10 mL), and the organic extracts were dried (Na$_2$SO$_4$), filtered, and concentrated to an orange oil. Flash chromatography (SiO$_2$, 0 to 100% EtOAc/hexanes) afforded 24 mg of a 55:45 mixture of two diastereomers of 5-{1-[methyl(4-(4-methoxyphenyl)-1,3-thiazol-2-yl)sulfonimidoyl]pentyl}-2-(trifluoromethyl)pyridine (60) as an orange oil. $^1$H NMR (CDCl$_3$) δ 8.80 (s, 0.45H), 8.73 (s, 0.55H), 8.11 (t, 1H), 7.78-7.72 (m, 3H), 6.96-6.87 (m, 2H), 6.81 (s, 0.45H), 6.78 (s, 0.55H), 5.26-5.21 (m, 0.45H), 4.96-4.91 (m, 0.55H), 3.85 (s, 1.4H), 3.84 (s, 1.6H), 3.27 (s, 1.5H), 3.10 (s, 1.4H), 2.51-2.04 (m, 2H), 1.43-1.14 (m, 4H), 0.92-0.79 (m, 3H). LC-MS (ESI) m/z 484 [M+H]$^+$, m/z 482 [M−H]$^−$.

Example XII

Preparation of 5-{1-[(5-benzyl-1,3-thiazol-2-yl)(methyl)sulfonimidoyl]ethyl}-2-(trifluoromethyl)pyridine (61)

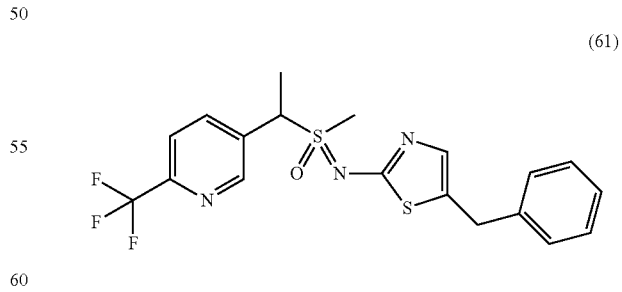

(1) Preparation of 2-bromo-3-phenylpropanal: dibromobarbituric acid (1.43 g, 5 mmol) was dissolved in diethylether (40 mL) and phenylpropionaldehyde (1.34 g, 1.33 mL, 10 mmol) was added. After stirring at room temperature for 5 days, precipitation of barbituric acid was observed. The reaction mixture was filtered and washed with sat. aq. NaHCO$_3$ (1×40 mL), and brine (2×40 mL). The mixture was dried over Na$_2$SO$_4$, filtered, and the solvent was removed under reduced pressure. GC-MS analysis of the concentrate showed 2-bromo-3-phenylpropanal as the sole product. (2) Preparation of (61): N-(methyl(oxo){1-[6-(trifluoromethyl)-3-pyridinyl]ethyl}-λ$^6$-sulfanylidene)thiourea (J) (100 mg, 0.321 mmol) was suspended in EtOH (1 mL) and 2-bromo-3-phenylpropanal (82 mg, 0.385 mmol, 1.2 eq) in EtOH (0.6 mL) was added. The reaction was stirred at r.t. for 1 h, and then heated to reflux for 30 min. The solvent was removed under reduced pressure and the residue purified by preparative reverse-phase column chromatography (water/acetonitrile). 5-{1-[(5-benzyl-1,3-thiazol-2-yl)(methyl)sulfonimidoyl]ethyl}-2-(trifluoromethyl)pyridine (61) was obtained in form of a yellowish oil (26 mg, 0.061 mmol, 19%) as a racemate and 1:1 mixture of diastereomers. $^1$H-NMR (CDCl$_3$, 400 MHz): δ=1.89 (d, J=7.2 Hz, 1.5H, CHCH$_3$, diastereomer 1); 1.92 (d, J=7.2 Hz, 1.5H, CHCH$_3$, diastereomer 2); 3.09 (s, 1.5H, S—CH$_3$, diastereomer 1); 3.20 (s, 1.5H, S—CH$_3$, diastereomer 2); 3.94 (s, 1H, CH$_2$Ph, diastereomer 1), 3.97 (s, 1H, CH$_2$Ph, diastereomer 2); 5.14 (q, J=7.2 Hz, 0.5H, CHCH$_3$, diastereomer 1); 5.21 (q, J=7.2 Hz, 0.5H, CHCH$_3$, diastereomer 2); 6.90 (s, 0.5H, thiazole, diastereomer 1); 6.92 (s, 0.5H, thiazole, diastereomer 2); 7.15-7.37 (m, 5H, Ph); 7.71 (d, J=8.2 Hz, 0.5H, pyr-C3-H, diastereomer 1), 7.72 (d, J=8.2 Hz, 0.5H, pyr-C3-H, diastereomer 2); 8.09 (dd, $^3$J=8.2 Hz, $^4$J=1.8 Hz, 0.5H, pyr-C4-H, diastereomer 1); 8.12 (dd, $^3$J=8.2 Hz, $^4$J=1.7 Hz, 0.5H, pyr-C4-H, diastereomer 2); 8.75 (d, $^4$J=1.8 Hz, 0.5H, pyr-C6-H, diastereomer 1); 8.79 (d, $^4$J=1.8 Hz, 0.5H, pyr-C6-H, diastereomer 2); $^{13}$C-NMR (CDCl$_3$, 100 MHz): δ=13.8, 14.2 (CHCH$_3$, two diastereomers); 33.2. 33.3 (CH$_2$Ph, two diastereomers); 36.5, 36.8 (S—CH$_3$, two diastereomers); 60.8, 61.6 (CHCH$_3$, two diastereomers); 119.5, 119.6 (pyr-C, 2 diastereomers); 125.6, 125.7 (Ph, two diastereomers), 127.2, 127.3 (Ph, two diastereomers, 127.5 (Ph, two diastereomers), 130.1, 130.2 (pyr-C, two diastereomers), 131.1, 131.5, (pyr-C, two diastereomers), 132.7, 133.2 (thiazole, two diastereomers); 137.3, 137.6 (pyr-C, 2-diastereomers); 137.9, 138.0 (thiazole, two diastaereomers); 149.2, 149.4 (pyr-C, 2-diastereomers); 165.6, 165.8 (thiazole, two diastereomers); CF$_3$, not detected. UPLC-MS (ESI$^+$): mass calc'd for C$_{19}$H$_{19}$F$_3$N$_3$OS$_2$ (M+H$^+$): 426.1, found 426.1, UPLC-MS (EST) mass calc'd for C$_{19}$H$_{17}$F$_3$N$_3$OS$_2$ (M−H$^+$): 424.1, found 424.1.

Example XIII

Preparation of 5-{1-[methyl(5-phenyl-1,3-thiazol-2-yl)sulfonimidoyl]ethyl}-2-(trifluoromethyl)pyridine (62)

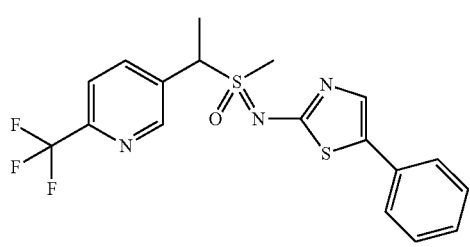

(62)

(1) Preparation of 2-bromo-2-phenylacetaldehyde: dibromobarbituric acid (1.43 g, 5 mmol) was dissolved in diethylether (40 mL) and phenylacetaldehyde (1.20 g, 10 mmol) was added. After stirring at r.t. over night, precipitation of barbituric acid was observed. The reaction mixture was filtered and washed with sat. aq. NaHCO$_3$ (1×40 mL), and brine (2×40 mL). The mixture was dried over Na$_2$SO$_4$, filtered, and the solvent was removed under reduced pressure. GC-MS analysis of the concentrate showed 2-bromo-2-phenylacetaldehyde as the sole product. (2) Preparation of (62): N-(methyl(oxo){1-[6-(trifluoromethyl)-3-pyridinyl]ethyl}-λ$^6$-sulfanylidene)thiourea (J) (100 mg, 0.321 mmol) was suspended in EtOH (1 mL) and 2-bromo-2-phenylacetaldehyde (64 mg, 0.321 mmol, 1.0 eq) in EtOH (0.6 mL) was added. The reaction was stirred at r.t. for 2 h, and then heated to reflux for 30 min. The solvent was removed under reduced pressure. UPLC-ESI/MS analysis of the crude residue showed that (62) had formed almost quantitatively. In order to remove traces of the starting material, the residue was purified by preparative reverse-phase column chromatography (water/acetonitrile). 5-{1-[methyl(5-phenyl-1,3-thiazol-2-yl)sulfonimidoyl]ethyl}-2-(trifluoromethyl)pyridine (62) was obtained in form of a yellow oil (66 mg, 0.161 mmol, 50%) as a racemate and 1:1 mixture of diastereomers. $^1$H-NMR (CDCl$_3$, 400 MHz): δ=1.92 (d, J=7.2 Hz, 1.5H, CHCH$_3$, diastereomer 1); 1.96 (d, J=7.2 Hz, 1.5H, CHCH$_3$, diastereomer 2); 3.11 (s, 1.5H, S—CH$_3$, diastereomer 1); 3.21 (s, 1.5H, S—CH$_3$, diastereomer 2); 5.14 (q, J=7.2 Hz, 0.5H, CHCH$_3$, diastereomer 1); 5.24 (q, J=7.2 Hz, 0.5H, CHCH$_3$, diastereomer 2); 7.29-7.48 (m, 5H, Ph); 7.73 (d, J=7.7 Hz, 0.5H, pyr-C3-H, diastereomer 1), 7.75 (d, J=7.8 Hz, 0.5H, pyr-C3-H, diastereomer 2); 8.05-8.12 (m, 1H pyr-C4-H, diastereomers 1, 2); 8.78 (d, $^4$J=1.6 Hz, 0.5H pyr-C6-H, diastereomer 1); 8.81 (d, $^4$J=1.6 Hz, 0.5H, pyr-C6-H, diastereomer 2); thiazole-H hidden underneath CHCl$_3$-peak. $^{13}$C-NMR (CDCl$_3$, 100 MHz): δ=13.8, 14.3 (CHCH$_3$, two diastereomers); 36.3, 36.4 (S—CH$_3$, two diastereomers); 60.6, 61.3 (CHCH$_3$, two diastereomers); 119.4, 119.6 (pyr-C, 2 diastereomers); 124.8 (Ph), 126.20, 126.21 (Ph, two diastereomers); 127.7, 127.8 (Ph, two diastereomers); 130.9 (pyr-C); 131.2, 131.3; (pyr-C, two diastereomers); 133.0 (thiazole); 137.2, 137.3 (pyr-C, 2-diastereomers); 149.2, 149.3 (pyr-C, 2-diastereomers); 161.0 (thiazole); 165.6, 165.8 (thiazole, two diastereomers); CF$_3$, not detected. UPLC-MS (ESI$^+$): mass calc'd for C$_{18}$H$_{17}$F$_3$N$_3$OS$_2$ (M+H$^+$): 412.1, found 411.8, UPLC-MS (ESI$^+$) mass calc'd for C$_{19}$H$_{15}$F$_3$N$_3$OS$_2$ (M−H$^+$): 410.1, found 410.1.

Example XIV

5-{1-[methyl(5-methyl-1,3-thiazol-2-yl)sulfonimidoyl]ethyl}-2-(trifluoromethyl)pyridine (63)

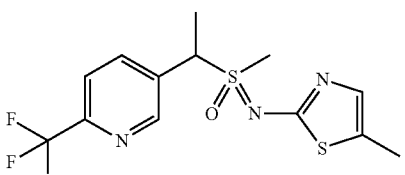

(63)

(1) Preparation of 2-bromo-propanal: dibromobarbituric acid (1.43 g, 5 mmol) was dissolved in diethylether (40 mL) and propionaldehyde (581 mg, 0.72 mL, 10 mmol) was added. After stirring at r.t. for 48 h, precipitation of barbituric acid was observed. The reaction mixture was filtered and washed with sat. aq. NaHCO$_3$ (1×40 mL), and brine (2×40 mL). After drying over Na$_2$SO$_4$, GC-MS analysis of the concentrate confirmed presence of 2-bromo-propanal as main product in the solution. (2) Preparation of (63): In a 25 mL roundbottom flask equipped with Vigreux column with attached Liebig condenser, N-(methyl(oxo){1-[6-(trifluoromethyl)-3-pyridinyl]ethyl}-λ$^6$-sulfanylidene)thiourea (J) (100 mg, 0.321 mmol) was suspended in EtOH (1 mL) and an excess of 2-bromo-propanal in diethylether (5 mL, as obtained in the 1$^{st}$ step) was added. The diethylether was completely removed by fractioned distillation within 3 h. After cooling, the distillation bridge was traded for a reflux condenser, and the remaining mixture was heated to reflux for 30 min. The solvent and remaining 2-bromo-propanal was finally removed under reduced pressure. UPLC-ELSD/MS analysis of the crude residue showed that (63) had formed almost quantitatively. In order to remove traces of the starting material, the residue was purified by preparative reverse-phase column chromatography (water/acetonitrile). 5-{1-[methyl(5-methyl-1,3-thiazol-2-yl)sulfonimidoyl]ethyl}-2-(trifluoromethyl)pyridine (63) was obtained in form of a yellow oil (65 mg, 0.186 mmol, 58%) as a racemate and 3:5 mixture of diastereomers. $^1$H-NMR (CDCl$_3$, 400 MHz): δ=1.88 (d, J=7.2 Hz, 1.12H, CHCH$_3$, diastereomer 1); 1.92 (d, J=7.2 Hz, 1.88H, CHCH$_3$, diastereomer 2); 2.29 (d, $^4$J=1.2 Hz, 1.88H, thiazole-CH$_3$, diastereomer 2); 2.31 (d, $^4$J=1.2 Hz, 1.12H, thiazole-CH$_3$, diastereomer 1); 3.03 (s, 1.12H, S—CH$_3$, diastereomer 1); 3.15 (s, 1.88H, S—CH$_3$, diastereomer 2); 5.13 (q, J=7.2 Hz, 0.63H, CHCH$_3$, diastereomer 2); 5.24 (q, J=7.2 Hz, 0.37H, CHCH$_3$, diastereomer 1); 6.83 (q, $^4$J=1.2 Hz, 0.63H, thiazole-H, diastereomer 2); 6.86 (q, $^4$J=1.2 Hz, 0.37H, thiazole-H, diastereomer 1); 7.71 (d, J=8.0 Hz, 0.63H, pyr-C3-H, diastereomer 2), 7.73 (d, J=8.0 Hz, 0.37H, pyr-C3-H, diastereomer 1); 8.04-8.09 (m, 1H pyr-C4-H, diastereomers 1, 2); 8.73 (d, $^4$J=1.8 Hz, 0.63H, pyr-C6-H, diastereomer 2); 8.78 (d, $^4$J=1.8 Hz, 0.37H, pyr-C6-H, diastereomer 1). $^{13}$C-NMR (CDCl$_3$, 100 MHz): δ=12.0 (thiazole-CH$_3$); 13.8, 14.3 (CHCH$_3$, two diastereomers); 36.1, 36.3 (S—CH$_3$, two diastereomers); 60.4, 61.0 (CHCH$_3$, two diastereomers); 119.4, 119.5 (pyr-C, 2 diastereomers); 131.5 (ar), 132.1 (ar), 134.5 (ar), 134.6 (ar), 137.1, 137.3 (pyr-C, 2-diastereomers); 149.2, 149.3 (pyr-C, 2-diastereomers); 164.7, 165.0 (thiazole, two diastereomers); CF$_3$, not detected. UPLC-MS (ESI$^+$): mass calc'd for C$_{13}$H$_{15}$F$_3$N$_3$OS$_2$ (M+H$^+$): 350.1, found 350.4, UPLC-MS (ESI$^-$) mass calc'd for C$_{13}$H$_{13}$F$_3$N$_3$OS$_2$ (M-H$^+$): 348.1, found 348.0.

Example XV

5-[1-(methyl{5-[(methylsulfanyl)methyl]-1,3-thiazol-2-yl}sulfonimidoyl)ethyl]-2-(trifluoromethyl)pyridine (64)

(64)

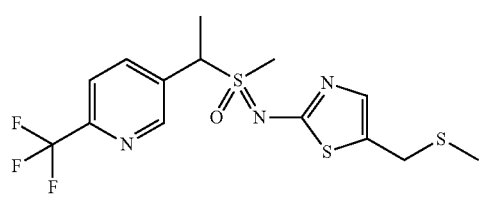

(1) Preparation of 2-bromo-3-(methylthio)propanal: dibromobarbituric acid (715 mg, 2.5 mmol) was dissolved in diethylether (20 mL) and 3-(methylthio)propionaldehyde (521 mg, 5.0 mmol) was added. After stirring at r.t. over night, precipitation of barbituric acid was observed. The reaction mixture was filtered and washed with sat. aq. NaHCO$_3$ (1×20 mL), and brine (2×20 mL). The mixture was dried over Na$_2$SO$_4$, and filtered. GC-MS analysis of the concentrate showed 2-bromo-3-(methylthio)propanal as the sole product. The solvent was removed under reduced pressure. The isolated 2-bromo-3-(methylthio)propanal polymerizes within 5-10 min; it was immediately used in the following reaction. (2) Preparation of (64): N-(methyl(oxo){1-[6-(trifluoromethyl)-3-pyridinyl]ethyl}-λ$^6$-sulfanylidene)thiourea (J) (100 mg, 0.321 mmol) was suspended in EtOH (1 mL) and 2-bromo-3-(methylthio)propanal (~65 mg, 0.35 mmol, 1.1 eq) in EtOH (0.6 mL) was added. The reaction was heated to reflux for 1 h. The solvent was removed under reduced pressure and the remaining residue was purified by preparative reverse-phase column chromatography (water/acetonitrile). 5-[1-(methyl{5-[(methyl sulfanyl)methyl]-1,3-thiazol-2-yl}sulfonimidoyl)ethyl]-2-(trifluoromethyl)pyridine (64) was obtained in form of a colorless oil (7 mg, 0.018 mmol, 5.5%) as a racemate and 1:1 mixture of diastereomers. $^1$H-NMR (CDCl$_3$, 400 MHz): δ=1.90 (d, J=7.2 Hz, 1.5H, CHCH$_3$, diastereomer 1); 1.93 (d, J=7.2 Hz, 1.5H, CHCH$_3$, diastereomer 2); 2.05 (s, 1.5H, S—CH$_3$, diastereomer 1); 2.07 (s, 1.5H, S—CH$_3$, diastereomer 2); 3.08 (s, 1.5H, SO—CH$_3$, diastereomer 1); 3.17 (s, 1.5H, SO—CH$_3$, diastereomer 2); 3.70, 3.72 (2H, S—CH$_2$); 5.08 (q, J=7.2 Hz, 0.5H, CHCH$_3$, diastereomer 1); 5.17 (q, J=7.2 Hz, 0.5H, CHCH$_3$, diastereomer 2); 6.97 (s, 0.5H, thiazole, diastereomer 1); 7.00 (s, 0.5H, thiazole, diastereomer 2); 7.71 (d, J=8.2 Hz, 0.5H, pyr-C3-H, diastereomer 1), 7.74 (d, J=8.2 Hz, 0.5H, pyr-C3-H, diastereomer 2); 8.04-8.10 (m, 1H, pyr-C4-H, diastereomers 1,2); 8.75 (d, $^4$J=1.8 Hz, 0.5H, pyr-C6-H, diastereomer 1); 8.79 (d, $^4$J=1.8 Hz, 0.5H, pyr-C6-H, diastereomer 2); UPLC-MS (ESI$^+$): mass calc'd for C$_{14}$H$_{17}$F$_3$N$_3$OS$_3$ (M+H$^+$): 396.1, found 396.1, UPLC-MS (ESI$^-$) mass calc'd for C$_{14}$H$_{15}$F$_3$N$_3$OS$_2$ (M-H$^+$): 394.0, found 394.1.

Example XVI

7-[(methyl(oxo){1-[6-(trifluoromethyl)-3-pyridinyl] ethyl}-λ$^6$-sulfanylidene)amino]-4,5-dihydro[1,3] thiazolo[4,5-e][2,1,3]-benzoxadiazole (65)

(65)

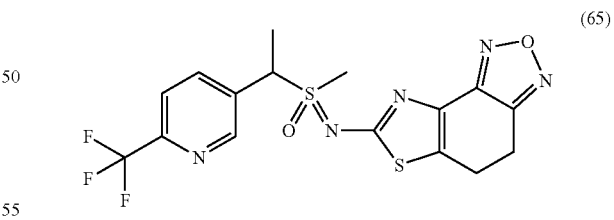

N-(methyl(oxo){1-[6-(trifluoromethyl)-3-pyridinyl] ethyl}-λ$^6$-sulfanylidene)thiourea (J) (100 mg, 0.321 mmol) and 5-bromo-6,7-dihydrobenzo[c][1,2,5]oxadiazol-4(5H)-one (76.6 mg, 0.353 mmol, 1.1 eq) were suspended in EtOH (1.6 mL). The reaction was stirred at room temperature for 2 h, and then heated to reflux for 1 h. The hot solution was filtered via a 0.45 μm nylon syringe filter and the filtrate was stored at −20° C. over night. 7-[(methyl(oxo){1-[6-(trifluoromethyl)-3-pyridinyl]ethyl}-λ$^6$-sulfanylidene)amino]-4,5-dihydro[1,3]thiazolo[4,5-e][2,1,3]benzoxadiazole (65) was obtained in form of slightly yellow crystals (70 mg, 0.163 mmol, 51%) as a 1:1 mixture of diastereomers (racemate) that were isolated by filtration, washed with a small amount of cold ethanol, and dried in the high vacuum. $^1$H-NMR (DMSO-$d_6$, 400 MHz): δ=1.87 (d, J=6.9 Hz, 1.5H, CHCH$_3$, diastereomer 1); 1.89 (d, J=6.9 Hz, 1.5H, CHCH$_3$, diastereomer 2); 3.06-3.27 (m, 4H, CH$_2$—CH$_2$, diastereomers 1, 2); 3.42 (s, 1.5H, S—CH$_3$, diastereomer 1); 3.43 (s, 1.5H, S—CH$_3$, diastereomer 2); 5.34 (q, J=6.9 Hz, 1H, CHCH$_3$, diastereomers 1, 2); 7.96 (d, J=7.7 Hz, 0.5H, pyr-C3-H, diastereomer 1), 7.98 (d, J=7.8 Hz, 0.5H, pyr-C3-H, diastereomer 2); 8.21-8.26 (m, 1H, pyr-C4-H, diastereomers 1, 2); 8.85 (d, 0.5H $^4$J=1.6 Hz, pyr-C6-H, diastereomer 1); 8.86 (d, 0.5H, $^4$J=1.6 Hz, pyr-C6-H, diastereomer 2). $^{13}$C-NMR (DMSO-$d_6$, 100 MHz): δ=13.3, 13.6 (CHCH$_3$, two diastereomers); 17.9 (double peak, CH$_2$, two diastereomers); 20.4 (double peak, CH$_2$, two diastereomers); 36.4, 36.5 (S—CH$_3$, two diastereomers); 60.8, 60.9 (CHCH$_3$, two diastereomers); 119.4, 119.5 (pyr-C, two diastereomers); 120.3 (q, $^2$J (C—F)=271.5 Hz, CF$_3$, two diastereomers), 131.6, 131.9; (pyr-C, two diastereomers); 132.0, 132.1 (Ar, two diastereomers), 132.4, 132.5 (Ar, two diastereomers); 138.0, 138.1 (pyr-C, two diastereomers); 145.0 (double peak, Ar, two diastereomers); 145.0, 145.1 (Ar, two diastereomers); 149.9 (double peak, pyr-C, two diastereomers); 151.2 (double peak, Ar, two diastereomers); 166.3, 166.6 (thiazole, two diastereomers). UPLC-MS (ESI$^+$): mass calc'd for $C_{16}H_{15}F_3N_5O_2S_2$ (M+H$^+$): 430.1, found 430.1, UPLC-MS (ESI$^+$) mass calc'd for $C_{16}H_{13}F_3N_5O_2S_2$ (M−H$^+$): 428.1, found 428.1.

Example XVII

Preparation of 5-{1-[methyl(5-methyl-4-phenyl-1,3-thiazol-2-yl)sulfonimidoyl]ethyl}-2-(trifluoromethyl)pyridine (66)

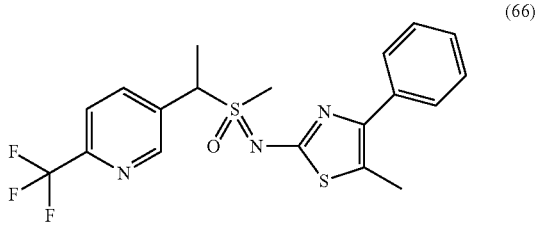 [SMILES: Cc1sc(N=S(C)(=O)C(C)c2ccc(C(F)(F)F)nc2)nc1-c1ccccc1]

(66)

In a microwave crimp tube, N-(methyl(oxo){1-[6-(trifluoromethyl)-3-pyridinyl]ethyl}-λ$^6$-sulfanylidene)thiourea (J) (200 mg, 0.642 mmol) was suspended in EtOH (3 mL) and 2-bromo-1-phenylpropan-1-one (137 mg, 87 μL, 0.642 mmol) was added via syringe, while stirring. The reaction was sealed and heated to 85° C. for 15 min in the microwave. The solvent was subsequently removed on the rotary evaporator and the remaining residue purified by preparative reverse phase chromatography (water/acetonitrile). Two fractions were isolated that contained mixtures of diastereomers at different ratios. Fraction 1 contained 5-{1-[methyl(5-methyl-4-phenyl-1,3-thiazol-2-yl)sulfonimidoyl]ethyl}-2-(trifluoromethyl)pyridine (66) (45 mg, 0.106 mmol, 16%) in form of a yellowish foam (2:1-mixture of diastereomers 1 and 2, racemate). Fraction 2 contained (66) (88 mg, 0.207 mmol, 32%) in form of a colorless oil (1:3-mixture of diastereomers 1 and 2 (racemate)). $^1$H-NMR (CDCl$_3$, 400 MHz): δ=1.88 (d, J=7.2 Hz, 0.75H, CHCH$_3$, diastereomer 1); 1.95 (d, J=7.2 Hz, 2.25H, CHCH$_3$, diastereomer 2); 2.41 (s, 2.25H, thiazole-CH$_3$, diastereomer 2); 2.44 (s, 0.75H, thiazole-CH$_3$, diastereomer 1); 3.09 (s, 0.75H, S—CH$_3$, diastereomer 1); 3.24 (s, 2.25H, S—CH$_3$, diastereomer 2); 5.25 (q, J=7.2 Hz, 0.75H, CHCH$_3$, diastereomer 2); 5.37 (q, J=7.2 Hz, 0.25H, CHCH$_3$, diastereomer 1); 7.26-7.34 (m, 1H, p-H, Ph, two diastereomers); 7.35-7.44 (m, 2H, Ph, two diastereomers); 7.54-7.62 (m, 2H, Ph, two diastereomers); 7.70 (d, J=8.2 Hz, 0.75H, pyr-C3-H, diastereomer 2), 7.74 (d, J=8.2 Hz, 0.25H, pyr-C3-H, diastereomer 1); 8.07 (dd, $^3$J=8.2 Hz, $^4$J=2.0 Hz, 0.75H, pyr-C4-H, diastereomer 2), 8.10 (dd, $^3$J=8.2 Hz, $^4$J=2.0 Hz, pyr-C4-H, 0.25H, diastereomer 1); 8.72 (d, $^4$J=2.0 Hz, 0.75H, pyr-C6-H, diastereomer 2); 8.78 (d, $^4$J=2.0 Hz, 0.25H, pyr-C6-H, diastereomer 1). $^{13}$C-NMR (CDCl$_3$, 100 MHz): δ=12.28 (thiazole-CH$_3$, diastereomer 2); 12.43 (thiazole-CH$_3$, diastereomer 1); 13.6 (CHCH$_3$, diastereomer 1); 14.4 (CHCH$_3$, diastereomer 2); 36.4 (S—CH$_3$, diastereomer 1); 36.6 (S—CH$_3$, diastereomer 2); 60.2 (CHCH$_3$, diastereomer 1); 60.9 (CHCH$_3$, diastereomer 2); 119.4 (pyr-C, diastereomer 2); 119.6 (pyr-C, diastereomer 1); 120.5 (Ar, diastereomer 2); 121.5 (Ar, diastereomer 1); 126.0 (double peak, Ph, two diastereomers); 127.07 (Ar, diastereomer 2); 127.13 (Ar, diastereomer 1); 127.18 (Ar, diastereomer 1); 127.28 (Ar, diastereomer 2); 131.3; (pyr-C, diastereomer 2; corresponding diastereomer 1 not detected); 134.0 (Ar, diastereomer 2; corresponding diastereomer 1 not detected); 137.1 (pyr-C, diastereomer 1); 137.3 (pyr-C, diastereomer 2); 149.3 (pyr-C, diastereomer 2); 149.4 (pyr-C, diastereomer 1); 161.9 (thiazole, diastereomer 2); 162.2 (thiazole, diastereomer 1); 164.4 (thiazole, diastereomer 2, corresponding diastereomer 1 not detected); 1 quat. Ar—C; CF$_3$, not detected. UPLC-MS (ESI$^+$): mass calc'd for $C_{19}H_{19}F_3N_3OS_2$ (M+H$^+$): 426.1, found 425.9, UPLC-MS (ESI$^-$) mass calc'd for $C_{19}H_{17}F_3N_3OS_2$ (M−H$^+$): 424.1, found 424.

Example XVIII

5-{1-[(4,5-dimethyl-1,3-thiazol-2-yl)(methyl)sulfonimidoyl]ethyl}-2-(trifluoromethyl)pyridine (67)

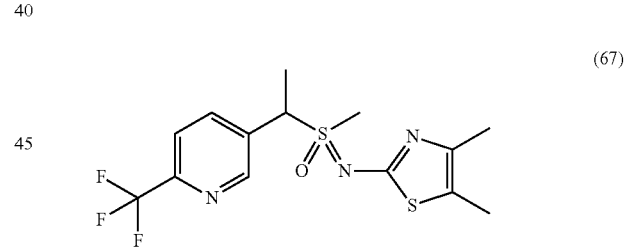

(67)

In a microwave crimp tube, N-(methyl(oxo){1-[6-(trifluoromethyl)-3-pyridinyl]ethyl}-λ$^6$-sulfanylidene)thiourea (J) (200 mg, 0.642 mmol) was suspended in EtOH (3 mL) and 3-bromobutan-2-one (151 mg, 69 μL, 0.642 mmol) was added via syringe, while stirring. The reaction was sealed and heated to 85° C. for 15 min in the microwave. The solvent was subsequently removed on the rotary evaporator and the remaining residue purified by preparative reverse phase chromatography (water/acetonitrile). 5-{1-[(4,5-dimethyl-1,3-thiazol-2-yl)(methyl)sulfonimidoyl]ethyl}-2-(trifluoromethyl)pyridine (67) was obtained in form of a slightly yellow oil as a 1:1 mixture of diastereomers (67 mg, 0.185 mmol, 29%). $^1$H-NMR (CDCl$_3$, 400 MHz): δ=1.89 (d, J=7.2 Hz, 1.5H, CHCH$_3$, diastereomer 1); 1.93 (d, J=7.2 Hz, 1.5H, CHCH$_3$, diastereomer 2); 2.15 (s, 1.5H, thiazole-CH$_3$, one diastereomer); 2.17 (s, 1.5H, thiazole-CH$_3$, one diastereomer); 2.18 (s, 1.5H, thiazole-CH$_3$, one diastereomer); 2.20

(s, 1.5H, thiazole-CH₃, one diastereomer); 3.04 (s, 1.5H, S—CH₃, diastereomer 1); 3.15 (s, 1.5H, S—CH₃, diastereomer 2); 5.11 (q, J=7.2 Hz, 0.5H, CHCH₃, diastereomer 1); 5.22 (q, J=7.2 Hz, 0.5H, CHCH₃, diastereomer 2); 7.71 (d, J=8.1 Hz, 0.5H, pyr-C3-H, diastereomer 1), 7.73 (d, J=8.1 Hz, 0.5H, pyr-C3-H, diastereomer 2); 8.08 (dd, ³J=8.1 Hz, ⁴J=2.0 Hz, 0.5H, pyr-C4-H, diastereomer 1); 8.10 (dd, ³J=8.1 Hz, ⁴J=2.0 Hz, 0.5H, pyr-C4-H, diastereomer 2); 8.72 (d, ⁴J=2.0 Hz, 0.5H, pyr-C6-H, diastereomer 1); 8.78 (d, ⁴J=2.0 Hz, 0.5H, pyr-C6-H, diastereomer 2). ¹³C-NMR (CDCl₃, 100 MHz): δ=10.9, 11.0 (thiazole-CH₃, two diastereomers); 13.8, 14.4 (CHCH₃, two diastereomers); 14.4 (double peak, thiazole-CH₃, two diastereomers); 36.3, 36.5 (S—CH₃, two diastereomers); 60.5, 61.2 (CHCH₃, two diastereomers); 117.9, 118.0 (Ar, two diastereomers); 119.4, 119.5 (pyr-C, 2 diastereomers); 131.4, 132.1 (Ar, two diastereomers), 137.1, 137.4 (pyr-C, 2-diastereomers); 141.7, 141.9 (Ar, two diastereomers) 149.3, 149.4 (pyr-C, 2-diastereomers); 161.4, 161.7 (thiazole, two diastereomers); CF₃, not detected. HPLC-MS (ESI⁺): mass calc'd for C₁₄H₁₇F₃N₃OS₂ (M+H⁺): 364.1, found 364.5, HPLC-MS (ESI⁺) mass calc'd for C₁₄H₁₅F₃N₃OS₂ (M–H⁺): 362.1, found 361.8.

Example XIX

5-{1-[[4-(4-bromophenyl)-5-methyl-1,3-thiazol-2-yl](methyl)sulfonimidoyl]ethyl}-2-(trifluoromethyl)pyridine (68)

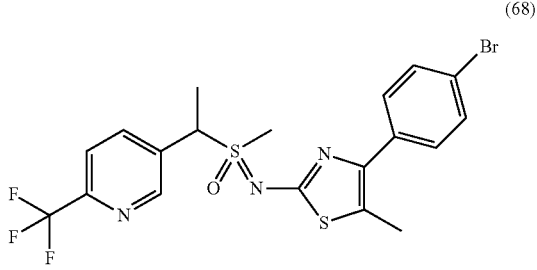 [SMILES: Cc1sc(N=S(C)(=O)C(C)c2ccc(C(F)(F)F)nc2)nc1-c1ccc(Br)cc1]

(68)

In a microwave crimp tube, N-(methyl(oxo){1-[6-(trifluoromethyl)-3-pyridinyl]ethyl}-λ⁶-sulfanylidene)thiourea (J) (200 mg, 0.642 mmol) was suspended in EtOH (3 mL) and 2-bromo-1-(4-bromophenyl)propan-1-one (187 mg, 0.642 mmol) was added, while stirring. The reaction was sealed and heated to 85° C. for 15 min in the microwave. The solvent was subsequently removed on the rotary evaporator and the remaining residue purified by preparative reverse phase chromatography (water/acetonitrile). Two fractions were isolated that contained mixtures of diastereomers at different ratios. Fraction 1 contained 5-{1-[[4-(4-bromophenyl)-5-methyl-1,3-thiazol-2-yl](methyl)sulfonimidoyl]ethyl}-2-(trifluoromethyl)pyridine (68) (43 mg, 0.085 mmol, 13%) in form of a white foam (1:3-mixture of diastereomers 1 and 2, racemate). Fraction 2 contained (68) (77 mg, 0.153 mmol, 24%) in form of off-white crystals (2:1-mixture of diastereomers 1 and 2 (racemate)): ¹H-NMR (CDCl₃, 400 MHz): δ=1.90 (d, J=7.2 Hz, 2H, CHCH₃, diastereomer 1); 1.95 (d, J=7.2 Hz, 1H, CHCH₃, diastereomer 2); 2.39 (s, 1H, thiazole-CH₃, diastereomer 2); 2.42 (s, 2H, thiazole-CH₃, diastereomer 1); 3.07 (s, 2H, S—CH₃, diastereomer 1); 3.22 (s, 1H, S—CH₃, diastereomer 2); 5.14 (q, J=7.2 Hz, 0.33H, CHCH₃, diastereomer 2); 5.25 (q, J=7.2 Hz, 0.67H, CHCH₃, diastereomer 1); 7.42-7.54 (m, 4H, Ph, two diastereomers); 7.71 (d, J=8.0 Hz, 0.33H, pyr-C3-H, diastereomer 2), 7.74 (d, J=8.0 Hz, 0.67H, pyr-C3-H, diastereomer 1); 8.06 (dd, ³J=8.0 Hz, ⁴J=2.0 Hz, (1-x) H, pyr-C4-H, one diastereomer), 8.08 (dd, ³J=8.2 Hz, ⁴J=2.0 Hz, x H, pyr-C4-H, one diastereomer); 8.72 (d, ⁴J=2.0 Hz, 0.33H, pyr-C6-H, diastereomer 2); 8.78 (d, ⁴J=2.0 Hz, 0.67H, pyr-C6-H, diastereomer 1). ¹³C-NMR (CDCl₃, 100 MHz): δ=12.41 (thiazole-CH₃, diastereomer 2); 12.43 (thiazole-CH₃, diastereomer 1); 13.7 (CHCH₃, diastereomer 1); 14.4 (CHCH₃, diastereomer 2); 36.4 (S—CH₃, diastereomer 1); 36.6 (S—CH₃, diastereomer 2); 60.5 (CHCH₃, diastereomer 1); 61.1 (CHCH₃, diastereomer 2); 119.4 (pyr-C, diastereomer 2); 119.6 (pyr-C, diastereomer 1); 120.0 (Ar, diastereomer 1); 120.9 (Ar, diastereomer 1); 121.1 (Ar, diastereomer 2); 128.7 (Ph, diastereomer 1); 128.8 (Ph, diastereomer 2); 130.16 (Ph, diastereomer 2); 130.22 (Ph, diastereomer 1); 131.3; (pyr-C, diastereomer 2); 132.0 (pyr-C, diastereomer 1); 133.1 (Ar, two diastereomers); 137.0 (pyr-C, diastereomer 1); 137.2 (pyr-C, diastereomer 2); 143.9 (Ar, two diastereomers); 149.3 (pyr-C, diastereomer 2); 149.4 (pyr-C, diastereomer 1); 162.0 (thiazole, diastereomer 2); 162.3 (thiazole, diastereomer 1); 1 quat. Ar—C; CF₃, not detected. UPLC-MS (ESI⁺): mass calc'd for C₁₉H₁₈BrF₃N₃OS₂ (M+H⁺): 504.0, 506.0, found 404.1, 506.1 UPLC-MS (ESI⁻) mass calc'd for C₁₉H₁₆BrF₃N₃OS₂ (M–H⁺): 502.0, 504.0, found 502.1, 504.1.

Example XX

Preparation of 5-{1-[[5-(difluoromethyl)-1,3,4-thiadiazol-2-yl](methyl)sulfonimidoyl]ethyl}-2-(trifluoromethyl)pyridine (69)

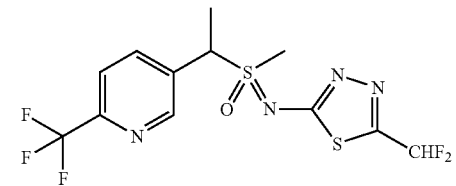

(69)

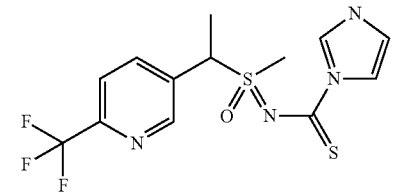

(Y)

To a solution of 5-[1-(methylsulfonimidoyl)ethyl]-2-(trifluoromethyl)pyridine (E) (400 mg, 1.59 mmol) in acetonitrile (5 mL), 1,1'-thiocarbonyldiimidazole (353 mg, 1.59 mmol, 1 eq) was added and stirred over night. A second aliquot of 1,1'-thiocarbonyldiimidazole (71 mg, 0.317 mmol, 0.2 eq) was added and the mixture heated to 60° C. for two hours. The solvent was removed under reduced pressure, the residue dissolved in CHCl₃ and washed five times with water. The organic phase was dried (Na₂SO₄) and chloroform was removed under reduced pressure. N-(Methyl(oxo){1-[6-(trifluoromethyl)-3-pyridinyl]ethyl}-λ⁶-sulfanylidene)-1H-imidazole-1-carbothioamide (Y) was obtained as an orange-brown residue, which was dried in the high vacuum over night (371 mg, 1.02 mmol, 64%). A 1:1 mixture of diastereomes with a purity of 94% was observed by UPLC-UV/ELSD and NMR, which was sufficient for subsequent conversions. Higher purities were obtained by filtration of the residue through a plug of silica (7.5% MeOH in CHCl$_3$). $^1$H NMR (CDCl$_3$, 400 MHz): δ=1.83 (d, J=7.1 Hz, 1.5H, CHCH$_3$, diastereomer 1); 1.86 (d, J=7.1 Hz, 1.5H, CHCH$_3$, diastereomer 2); 2.86 (s, 1.5H, S—CH$_3$, diastereomer 1); 2.89 (s, 1.5H, S—CH$_3$, diastereomer 2); 4.32 (q, J=7.1 Hz, 0.5H, CHCH$_3$, diastereomer 1); 4.37 (q, J=7.1 Hz, 0.5H, CHCH$_3$, diastereomer 2); 7.68-7.85 (m, 2H, Ar), 7.97-8.14 (m, 2H, Ar), 8.67-8.82 (m, 2H, Ar), UPLC-MS (ESI$^+$): mass calc'd for C$_{13}$H$_{12}$F$_3$N$_4$OS$_2$ (M+H$^+$): 363.0, found 363.1, UPLC-MS (ESI$^+$) mass calc'd for C$_{13}$H$_{14}$F$_3$N$_4$OS$_2$ (M–H$^+$): 361.0, found 361.1.

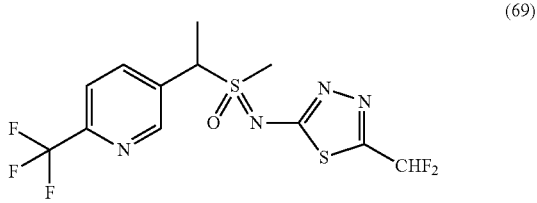 [SMILES: CC(c1ccc(C(F)(F)F)nc1)S(C)(=O)=Nc1nnc(C(F)F)s1]

(69)

N-(Methyl(oxo){1-[6-(trifluoromethyl)-3-pyridinyl]ethyl}-λ$^6$-sulfanylidene)-1H-imidazole-1-carbothioamide (Y) (300 mg, 0.83 mmol) was dissolved in acetonitrile (10 mL) and cooled to 0° C. While stirring, hydrazine (64-65% soln. in water, 30.8 μL, 31.9 mg, 0.64 mmol) was added via syringe. After 10 min, the mixture was poured into a saturated aqueous solution of NH$_4$Cl (100 mL), which was extracted once with CHCl$_3$ (100 mL). The organic phase was washed with several aliquots of sat. aq. NH$_4$Cl until the aqueous phase was slightly acidic, and dried over Na$_2$SO$_4$. After filtration, difluoroacetic anhydride (154 μL, 216 mg, 1.24 mmol) was added dropwise to organic phase, which was then stirred at r.t. for 20 min. The solvent was removed under reduced pressure. The crude concentrate contained the expected difluoroacetylsemicarbazide (41%, not stable) and the difluoroacetimide (54%) as the main products. The concentrate was dissolved in 1,2-dichloroethane (10 mL) and POCl$_3$ (2 mL) was added dropwise, while stirring. The mixture was heated in the microwave to 75° C. for 5 min and added slowly to 150 mL of sat. aq. NaHCO$_3$. After decomposition of the phosphorylchloride, the mixture was extracted with CHCl$_3$ (3×50 mL). The pooled organic phases were washed with sat. aq. NH$_4$OH (4×50 mL), sat. aq. NH$_4$Cl (50 mL aliquots, until neutral), dried over NaSO$_4$ and the solvent was removed under reduced pressure. 5-{1-[[5-(Difluoromethyl)-1,3,4-thiadiazol-2-yl](methyl)sulfonimidoyl]ethyl}-2-(trifluoromethyl)pyridine (69) was isolated by preparative reverse-phase chromatography. Pure (69) (1:1 mixture of diastereomers, racemate) was obtained as colorless oil (12 mg, 0.031 mmol, 3.7%). $^1$H-NMR (CDCl$_3$, 400 MHz): δ=1.89 (d, J=7.2 Hz, 1.5H, CHCH$_3$, diastereomer 1); 1.97 (d, J=7.2 Hz, 1.5H, CHCH$_3$, diastereomer 2); 3.18 (s, 1.5H, S—CH$_3$, diastereomer 1); 3.31 (s, 1.5H, S—CH$_3$, diastereomer 2); 5.21 (q, J=7.2 Hz, 0.5H, CHCH$_3$, diastereomer 1); 5.27 (q, J=7.2 Hz, 0.5H, CHCH$_3$, diastereomer 2); 6.79 (t, J=53.8 Hz, 0.5H, CHF$_2$, diastereomer 1); 6.80 (t, J=53.8 Hz, 0.5H, CHF$_2$, diastereomer 2); 7.74 (d, J=8.2 Hz, 0.5H, pyr-C3-H, diastereomer 1), 7.78 (d, J=8.2 Hz, 0.5H, pyr-C3-H, diastereomer 2); 8.04 (dd, $^3$J=8.2 Hz, $^4$J=2.0 Hz, 0.5H, pyr-C4-H, diastereomer 1); 8.09 (dd, $^3$J=8.2 Hz, $^4$J=2.0 Hz, 0.5H, pyr-C4-H, diastereomer 2); 8.73 (d, $^4$J=2.0 Hz, 0.5H, pyr-C6-H, diastereomer 1); 8.82 (d, $^4$J=2.0 Hz, 0.5H, pyr-C6-H, diastereomer 2). $^{13}$C-NMR (CDCl$_3$, 100 MHz): δ=13.5, 14.3 (CHCH$_3$, two diastereomers); 36.4, 36.5 (S—CH$_3$, two diastereomers); 60.8, 61.4 (CHCH$_3$, two diastereomers); 109.5 (t, $^2$J=236.2 Hz, CHF$_2$); 119.6, 119.8 (pyr-C, 2 diastereomers); 130.3 (pyr-C); 131.1 (pyr-C); 137.2, 137.3 (pyr-C, 2-diastereomers); 148.2 (dd, $^3$J=20.1 Hz, $^2$J=35.2 Hz, CCF$_2$H); 149.2, 149.4 (pyr-C, 2-diastereomers); 169.4, 169.5 (thiadiazole-2'C); CF$_3$, not detected. UPLC-MS (ESI$^+$): mass calc'd for C$_{12}$H$_{12}$F$_5$N$_4$OS$_2$ (M+H$^+$): 387.0, found 387.1, UPLC-MS (ESI$^-$) mass calc'd for C$_{12}$H$_{10}$F$_5$N$_4$OS$_2$ (M–H$^+$): 385.0, found 385.1.

Example XXI

Preparation of 5-{1-[methyl(4-ethyl-1,3-oxazol-2-yl)sulfonimidoyl]ethyl}-2-(trifluoromethyl)pyridine (70)

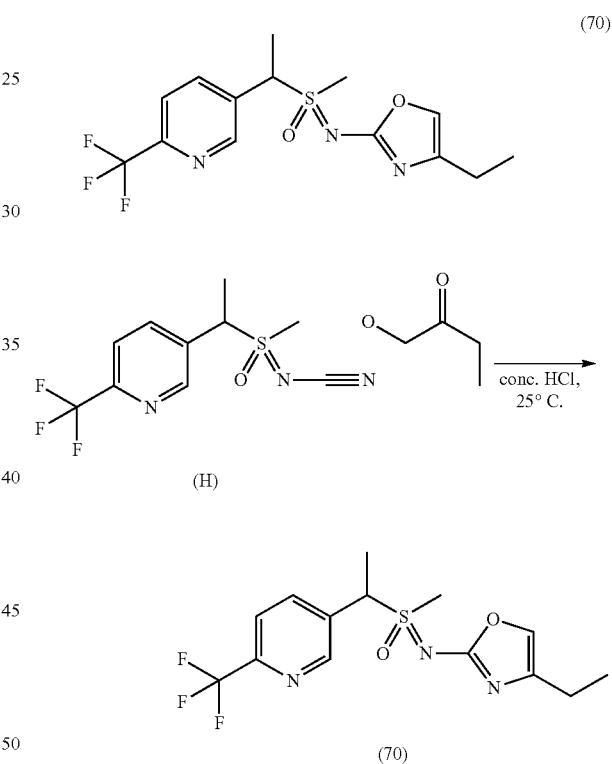

To a solution of sulfoximine (H) (200 mg, 0.7 mmol) in 1-hydroxy-2-butanone (0.6 mL, 7 mmol) was added concentrated HCl (3 drops). Let stir overnight, then the reaction was quenched with 1 M NaOH until neutral. Extraction with ethyl acetate, drying over sodium sulfate, concentration and purification by reverse phase chromatography furnished 5-{1-[methyl(4-ethyl-1,3-oxazol-2-yl)sulfonimidoyl]ethyl}-2-(trifluoromethyl)pyridine (70) as brown oil=75 mg (30%). 1:1 mixture of two diastereomers $^1$H NMR (400 MHz, CDCl$_3$) δ 8.81 (s, 1H), 8.78 (s, 1H), 8.15 (dd, 1H), 8.11 (dd, 1H), 7.77 (dd, 2H), 7.02 (s, 1H), 6.98 (s, 1H), 5.15 (q, 1H), 5.04 (q, 1H), 3.22 (s, 3H), 3.13 (s, 3H), 2.46 (m, 4H), 1.97 (m, 6H), 1.21 (m, 6H); LC-MS (ESI): Mass calcd for C$_{14}$H$_{15}$F$_3$N$_3$O$_2$S [M–H]$^+$, 346. Found 346.

TABLE 6

| Cmpd # | Structure | Route | Characterization |
|---|---|---|---|
| 71 | 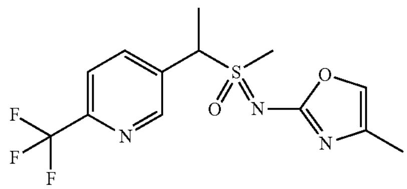 [SMILES: Cc1coc(N=S(C)(=O)C(C)c2ccc(C(F)(F)F)nc2)n1] | H | Brown oil. 1:1 mixture of two diastereomers; ¹H NMR (400 MHz, CDCl₃) δ 8.78 (m, 2H), 8.14 (dd, 1H), 8.08 (dd, 1H), 7.75 (m, 2H), 7.01 (s, 1H), 6.98 (s, 1H), 5.12 (q, 1H), 5.02 (q, 1H), 3.19 (s, 3H), 3.11 (s, 3H), 2.06-2.08 (m, 6H), 1.93-1.97 (m, 6H); LC-MS (ESI): Mass calcd for $C_{13}H_{13}F_3N_3O_2S$ [M − H]⁺, 332. Found 332. |
| 72 | 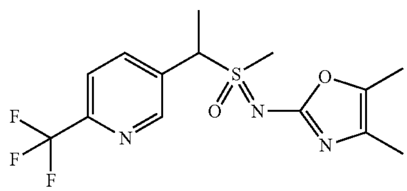 [SMILES: Cc1nc(N=S(C)(=O)C(C)c2ccc(C(F)(F)F)nc2)oc1C] | H | Brown oil. 1:1 mixture of two diastereomers; ¹H NMR (400 MHz, CDCl₃) δ 8.79 (s, 1H), 8.77 (s, 1H), 8.12 (dd, 1H), 8.07 (dd, 1H), 7.74 (m, 2H), 5.13 (q, 1H), 5.01 (q, 1H), 3.17 (s, 3H), 3.09 (s, 3H), 2.12-2.14 (m, 6H), 1.93-2.01 (m, 12H); LC-MS (ESI): Mass calcd for $C_{14}H_{17}F_3N_3O_2S$ [M + H]⁺, 348. Found 348. |
| 73 | 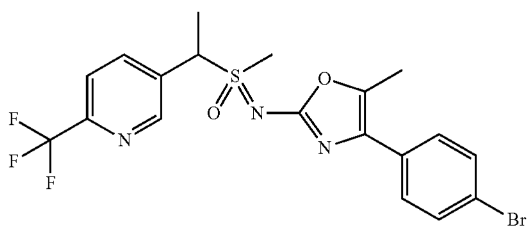 [SMILES: Cc1oc(N=S(C)(=O)C(C)c2ccc(C(F)(F)F)nc2)nc1-c1ccc(Br)cc1] | H | Yellow oil. 1:1 mixture of two diastereomers; ¹H NMR (400 MHz, CDCl₃) δ 8.83 (s, 1H), 8.81 (s, 1H), 8.15 (dd, 1H), 8.11 (dd, 1H), 7.77 (m, 2H), 7.48-7.52 (m, 4H), 7.37 (m, 4H), 5.16 (q, 1H), 5.08 (q, 1H), 2.33 (s, 3H), 2.31 (s, 3H), 1.96-2.00 (m, 6H); LC-MS (ESI): Mass calcd for $C_{19}H_{17}BrF_3N_3O_2S$ [M + H]⁺, 489. Found 489. |
| 74 | 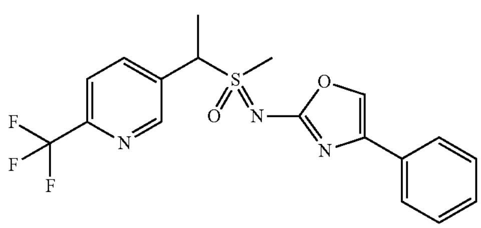 [SMILES: CC(c1ccc(C(F)(F)F)nc1)S(C)(=O)=Nc1nc(-c2ccccc2)co1] | H | Yellow oil. 1:1 mixture of two diastereomers; ¹H NMR (400 MHz, CDCl₃) δ 8.85 (s, 1H), 8.80 (s, 1H), 8.12-8.15 (m, 2H), 7.79 (d, 1H), 7.76 (d, 1H), 7.68 (m, 4H), 7.59 (s, 1H), 7.55 (s, 1H), 7.35-7.40 (m, 4H), 7.29 (m, 2H), 5.26 (q, 1H), 5.15 (q, 1H), 3.29 (s, 3H), 3.19 (s, 3H), 2.00 (d, 3H), 1.96 (d, 3H); LC-MS (ESI): Mass calcd for $C_{18}H_{17}F_3N_3O_2S$ [M + H]⁺, 396. Found 396. |
| 75 | 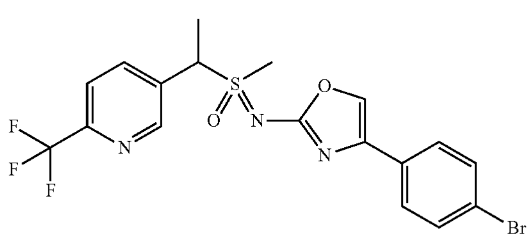 [SMILES: CC(c1ccc(C(F)(F)F)nc1)S(C)(=O)=Nc1nc(-c2ccc(Br)cc2)co1] | H | White solid, mp = 134-137° C. 2:1 mixture of two diastereomers.; ¹H NMR (400 MHz, CDCl₃) δ 8.83 (s, 1H), 8.80 (s, 1H), 8.11-8.14 (m, 2H), 7.78 (d, 1H), 7.76 (d, 1H), 7.47-7.58 (m, 10H), 5.16 (q, 1H), 5.07 (q, 1H), 3.28 (s, 3H), 3.20 (s, 3H), 2.01 (d, 3H), 1.98 (d, 3H); LC-MS (ESI): Mass calcd for $C_{18}H_{15}BrF_3N_3O_2S$ [M]⁺, 474. Found 474. |

H = route used in example XXI.

Example XXII

Preparation of 2-[2-(6-chloropyridin-3-yl)-1-oxido-tetrahydro-1H-1λ⁴-thiophen-1-ylidene]-4-tert-butyl-1,3-thiazole (76)

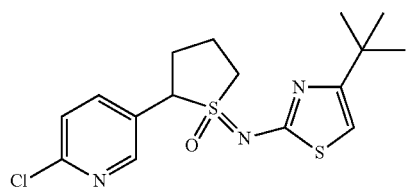
(76)

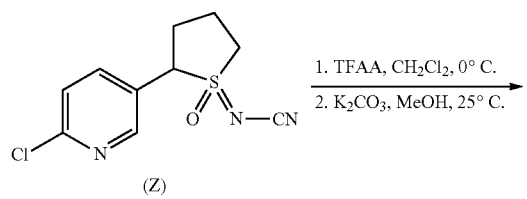

2-(6-chloropyridin-3-yl)-1-oxido-tetrahydro-1H-1λ⁴-thiophen-1-ylidenecyanamide (Z) was prepared as described in patent WO 2007149134 (Example VI). 2-(6-Chloropyridin-3-yl)-1-oxido-tetrahydro-1H-1λ⁴-thiophen-1-imine-1-oxide (AA) was synthesized from (Z) according to the procedure described in Example VIII. Isolated as a brown solid. $^1$H NMR (400 MHz, CDCl$_3$) δ (mixture of diastereomers) 8.39 (dd, 2H), 7.68-7.77 (m, 2H), 7.40 (m, 2H), 4.26-4.32 (m, 1H), 4.10-4.17 (m, 1H), 3.24-3.48 (m, 4H), 2.24-2.60 (m, 8H); LC-MS (ESI): Found [M+H]$^+$ 231. Calcd for C$_9$H$_{12}$ClN$_2$OS=231.

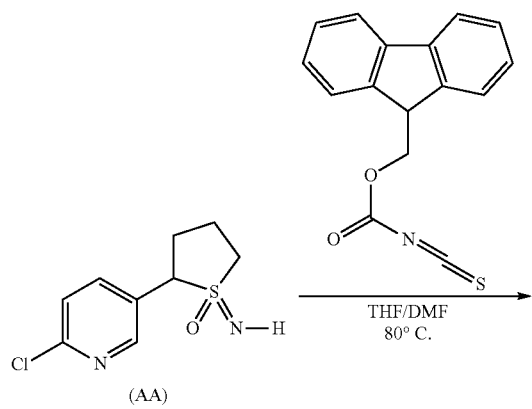

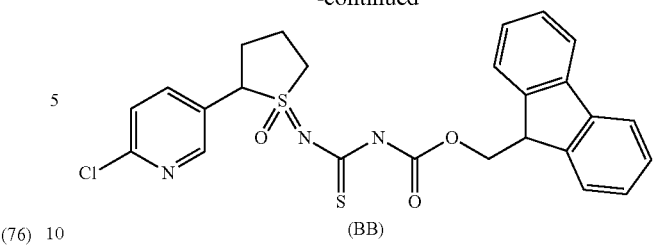
(BB)

Compound (BB) was synthesized from compound (AA) according to the procedure described in Example VIII. Isolated as an off-white solid. $^1$H NMR (400 MHz, CDCl$_3$) δ (mixture of diastereomers) 8.47 (dd, 2H), 8.21 (s, 1H), 8.07-8.12 (m, 2H), 7.84 (dd, 1H), 7.78 (d, 4H), 7.58 (d, 4H), 7.30-7.45 (m, 8H), 4.91-4.97 (m, 1H), 4.54-4.65 (m, 1H), 4.43-4.50 (m, 5H), 4.25 (m, 3H), 3.49-3.72 (m, 2H), 2.23-2.71 (m, 8H); LC-MS (ESI): Found [M]$^+$ 512. Calcd for C$_{25}$H$_{22}$ClN$_3$O$_3$S$_2$=512.

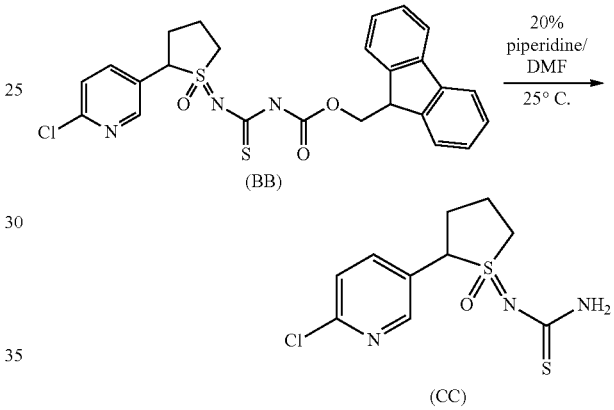

Thiourea (CC) was synthesized from (BB) according to the procedure described in Example VIII. Isolated as an off-white solid. $^1$H NMR (400 MHz, DMSO-d$_6$) δ (mixture of diastereomers) 8.94 (d, 1H), 8.88 (d, 1H), 8.48 (d, 1H), 8.41 (dd, 2H), 8.31 (d, 1H), 8.13 (br d, 4H), 5.56-5.62 (m, 1H), 5.00-5.11 (m, 1H), 4.67-4.75 (m, 1H), 3.91-4.26 (m, 3H), 2.65-3.16 (m, 8H); LC-MS (ESI): Found [M+H]$^+$ 290. Calcd for C$_{10}$H$_{13}$ClN$_3$OS$_2$=290.

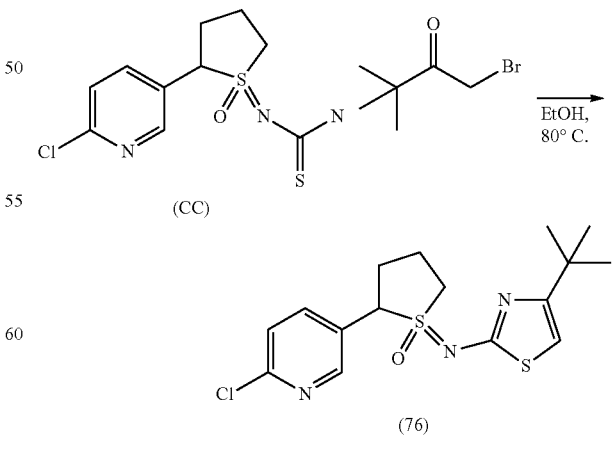

2-[2-(6-chloropyridin-3-yl)-1-oxido-tetrahydro-1H-1λ⁴-thiophen-1-ylidene]-4-tert-butyl-1,3-thiazole (76) was synthesized from (CC) according to the procedure described in Example VIII. Isolated as an off-white solid. Mp=77-81° C.; $^1$H NMR (400 MHz, CDCl$_3$) δ (mixture of diastereomers) 8.70 (dd, 1H), 8.48 (d, 1H), 8.40 (d, 1H), 7.93 (dd, 1H), 7.38 (d, 2H), 6.25 (s, 1H), 6.09 (s, 1H), 5.44-5.51 (m, 1H), 4.62-4.70 (m, 1H), 4.18 (m, 2H), 3.51-3.73 (m, 2H), 2.36-3.12 (m, 8H), 1.44 (s, 9H), 1.42 (s, 9H); LC-MS (ESI): Found [M+H]$^+$ 370. Calcd for $C_{16}H_{21}ClN_3OS_2$=370.

Devilbiss aspirator type sprayer was used to apply the spray solutions until runoff to both sides of the squash cotyledon leaves. Four plants (4 replications) were used for each compound. Reference plants (solvent check) were sprayed with the diluent only. Treated plants were held in a holding room for 3 days at approximately 23° C. and 40% RH before the number of live aphids on each plant was recorded. Insecti-

| Cmpd # | Structure | Route | Characterization |
|---|---|---|---|
| 77 | [structure] | I | Off-white solid, mp = 67-71° C. 1:1 mixture of two diastereomers; $^1$H NMR (CDCl$_3$) δ 8.47 (d, 1H), 8.39 (d, 1H), 7.86 (dd, 2H), 7.55 (d, 1H), 7.40 (d, 1H), 6.26 (s, 1H), 6.15 (s, 1H), 5.22-5.28 (m, 1H), 4.66-4.72 (m, 1H), 4.06-4.14 (m, 1H), 3.89-3.99 (m, 1H), 3.55-3.74 (m, 2H), 2.48-2.88 (m, 12H), 1.31 (t, 6H). LC-MS (ESI): Mass calcd for $C_{14}H_{16}ClN_3OS_2$ [M]$^+$, 341. Found 341. |
| 78 | [structure] | I | White solid, mp = 88-94° C. 1:1 mixture of two diastereomers; $^1$H NMR (CDCl$_3$) δ 8.49 (d, 1H), 8.43 (d, 1H), 7.84-7.99 (m, 6H), 7.39 (d, 2H), 6.94-7.01 (m, 4H), 6.63 (s, 1H), 6.50 (s, 1H), 5.39-5.45 (m, 1H), 4.62-4.70 (m, 1H), 4.15-4.23 (m, 1H), 3.98 (m, 1H), 3.84 (s, 3H), 3.83 (s, 3H), 3.52-3.71 (m, 2H), 2.50-2.88 (m, 8H). LC-MS (ESI): Mass calcd for $C_{19}H_{19}ClN_3O_2S_2$ [M + H]$^+$, 420. Found 420. |
| 79 | [structure] | I | White solid. One diastereomer isolated; $^1$H NMR (CDCl$_3$) δ 8.41 (d, 1H), 7.81 (dd, 1H), 7.39 (d, 1H), 7.15 (s, 1H), 4.93-5.00 (m, 1H), 3.94-4.02 (m, 1H), 3.25-3.36 (m, 1H), 2.70-2.79 (m, 1H), 2.37-2.62 (m, 3H). LC-MS (ESI): Mass calcd for $C_{13}H_{12}ClF_3N_3OS_2$ [M + H]$^+$, 382. Found 382. |

I = route used in example XXII.

Example XXIII

Insecticidal Testing

The compounds identified in the foregoing examples were tested against cotton aphid using procedures described hereinafter.

Insecticidal Test for Cotton Aphid (*Aphis gossypii*) in Foliar Spray Assay

Squash seedlings with fully expanded cotyledon leaves were trimmed to one cotyledon per plant and infested with cotton aphid (wingless adults and nymphs) 1 day prior to chemical application. Each plant was examined before chemical application to ensure uniform infestation (ca. 30-70 aphids per plant). Compounds (2 mg) were dissolved in 2 ml of acetone:methanol (1:1) solvent, forming stock solutions of 1000 ppm. The stock solutions were diluted 5× with 0.025% Tween 20 in H$_2$O to obtain a solution at 200 ppm. A hand-held cidal activity was measured by Corrected % Control using Abbott's correction formula and presented in Table 1-Activity:

Corrected % Control=100*(X−Y)/X where X=No. of live aphids on solvent check plants
Y=No. of live aphids on treated plants
Results are shown in Table 7.
Insecticidal Test for Green Peach Aphid (*Myzus persicae*) in Foliar Spray Assay Cabbage seedlings grown in 3-inch pots, with 2-3 small (3-5 cm) true leaves, were used as test substrate. The seedlings were infested with 20-50 green peach aphids (wingless adult and nymph) 1-2 days prior to chemical application. Four seedlings were used for each treatment. Compounds (2 mg) were dissolved in 2 ml of acetone:methanol (1:1) solvent, forming stock solutions of 1000 ppm. The stock solutions were diluted 5× with 0.025% Tween 20 in H$_2$O to obtain a solution at 200 ppm. A hand-held Devilbiss aspirator sprayer was used for spraying a solution to both sides of cabbage leaves until runoff. Reference plants (solvent check) were sprayed with the diluent only. Treated plants were held in a holding room for three days at approximately 23° C. and 40% RH prior to grading. Evaluation was conducted by counting the number of live aphids per plant under a microscope. Insecticidal activity was measured by using Abbott's correction formula:

Corrected % Control=100*(X−Y)/X where X=No. of live aphids on solvent check plants
Y=No. of live aphids on treated plants

TABLE 7

| | Activity. | |
|---|---|---|
| Comp # | Rating against cotton aphid on squash (foliar spray) 200 ppm | Rating against green peach aphid on cabbage (foliar spray) 200 ppm |
| 1 | A | A |
| 2 | A | A |
| 3 | C | A |
| 4 | A | B |
| 5 | B | C |
| 6 | A | A |
| 7 | A | A |
| 8 | B | B |
| 9 | C | A |
| 10 | C | B |
| 11 | C | B |
| 12 | B | C |
| 13 | A | B |
| 14 | C | B |
| 15 | C | A |
| 16 | C | A |
| 17 | C | B |
| 18 | C | A |
| 19 | C | A |
| 20 | C | A |
| 21 | C | A |
| 22 | C | A |
| 23 | C | A |
| 24 | A | B |
| 25 | C | B |
| 26 | C | A |
| 27 | C | A |
| 28 | C | A |
| 29 | C | A |
| 30 | C | A |
| 31 | C | A |
| 32 | C | B |
| 33 | C | A |
| 34 | C | A |
| 35 | C | A |
| 36 | C | A |
| 37 | C | A |
| 38 | C | A |
| 39 | C | A |
| 40 | C | A |
| 41 | C | A |
| 42 | C | A |
| 43 | C | A |
| 44 | C | A |
| 45 | C | A |
| 46 | C | A |
| 47 | C | A |
| 48 | C | A |
| 49 | C | A |
| 50 | C | A |
| 51 | C | A |
| 52 | C | A |
| 53 | C | A |
| 54 | C | B |
| 55 | C | A |
| 56 | C | A |
| 57 | C | B |

TABLE 7-continued

| | Activity. | |
|---|---|---|
| Comp # | Rating against cotton aphid on squash (foliar spray) 200 ppm | Rating against green peach aphid on cabbage (foliar spray) 200 ppm |
| 58 | C | A |
| 59 | C | A |
| 60 | C | B |
| 61 | C | A |
| 62 | C | A |
| 63 | C | A |
| 64 | C | A |
| 65 | C | A |
| 66 | C | A |
| 67 | C | A |
| 68 | C | A |
| 69 | C | A |
| 70 | C | A |
| 71 | C | A |
| 72 | C | B |
| 73 | C | A |
| 74 | C | B |
| 75 | C | B |
| 76 | C | A |
| 77 | C | A |
| 78 | C | B |
| 79 | C | A |

In each case of Table 7 the rating scale is as follows:

| % Control (or Mortality) | Rating |
|---|---|
| 80-100 | A |
| Less than 80 | B |
| Not tested | C |

Acid & Salt Derivatives, and Solvates

The compounds disclosed in this invention can be in the form of pesticidally acceptable acid addition salts.

By way of non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, and hydroxyethanesulfonic, acids.

Additionally, by way of non-limiting example, an acid function can form salts including those derived from alkali or alkaline earth metals and those derived from ammonia and amines. Examples of preferred cations include sodium, potassium, magnesium, and aminium cations.

The salts are prepared by contacting the free base form with a sufficient amount of the desired acid to produce a salt. The free base forms may be regenerated by treating the salt with a suitable dilute aqueous base solution such as dilute aqueous NaOH, potassium carbonate, ammonia, and sodium bicarbonate.

As an example, in many cases, a pesticide is modified to a more water soluble form e.g. 2,4-dichlorophenoxy acetic acid dimethyl amine salt is a more water soluble form of 2,4-dichlorophenoxy acetic acid a well known herbicide.

The compounds disclosed in this invention can also form stable complexes with solvent molecules that remain intact after the non-complexed solvent molecules are removed from the compounds. These complexes are often referred to as "solvates".

Stereoisomers

Certain compounds disclosed in this invention can exist as one or more stereoisomers. The various stereoisomers include geometric isomers, diastereomers, and enantiomers. Thus, the compounds disclosed in this invention include racemic mixtures, individual stereoisomers, and optically active mixtures.

It will be appreciated by those skilled in the art that one stereoisomer may be more active than the others. Individual stereoisomers and optically active mixtures may be obtained by selective synthetic procedures, by conventional synthetic procedures using resolved starting materials, or by conventional resolution procedures.

Pests

In another embodiment, the invention disclosed in this document can be used to control pests.

In another embodiment, the invention disclosed in this document can be used to control pests of the Phylum Nematoda.

In another embodiment, the invention disclosed in this document can be used to control pests of the Phylum Arthropoda.

In another embodiment, the invention disclosed in this document can be used to control pests of the Subphylum Chelicerata.

In another embodiment, the invention disclosed in this document can be used to control pests of the Class Arachnida.

In another embodiment, the invention disclosed in this document can be used to control pests of the Subphylum Myriapoda.

In another embodiment, the invention disclosed in this document can be used to control pests of the Class Symphyla.

In another embodiment, the invention disclosed in this document can be used to control pests of the Subphylum Hexapoda.

In another embodiment, the invention disclosed in this document can be used to control pests of the Class Insecta.

In another embodiment, the invention disclosed in this document can be used to control Coleoptera (beetles). A non-exhaustive list of these pests includes, but is not limited to, *Acanthoscelides* spp. (weevils), *Acanthoscelides obtectus* (common bean weevil), *Agrilus planipennis* (emerald ash borer), *Agriotes* spp. (wireworms), *Anoplophora glabripennis* (Asian longhorned beetle), *Anthonomus* spp. (weevils), *Anthonomus grandis* (boll weevil), *Aphidius* spp., *Apion* spp. (weevils), *Apogonia* spp. (grubs), *Ataenius spretulus* (Black Turgrass *Ataenius*), *Atomaria linearis* (pygmy mangold beetle), *Aulacophore* spp., *Bothynoderes punctiventris* (beet root weevil), *Bruchus* spp. (weevils), *Bruchus pisorum* (pea weevil), *Cacoesia* spp., *Callosobruchus maculatus* (southern cow pea weevil), *Carpophilus hemipteras* (dried fruit beetle), *Cassida vittata, Cerosterna* spp, *Cerotoma* spp. (chrysomeids), *Cerotoma trifurcata* (bean leaf beetle), *Ceutorhynchus* spp. (weevils), *Ceutorhynchus assimilis* (cabbage seedpod weevil), *Ceutorhynchus napi* (cabbage curculio), *Chaetocnema* spp. (chrysomelids), *Colaspis* spp. (soil beetles), *Conoderus scalaris, Conoderus stigmosus, Conotrachelus nenuphar* (plum curculio), *Cotinus nitidis* (Green June beetle), *Crioceris asparagi* (asparagus beetle), *Cryptolestes ferrugineus* (rusty grain beetle), *Cryptolestes pusillus* (flat grain beetle), *Cryptolestes turcicus* (Turkish grain beetle), *Ctenicera* spp. (wireworms), *Curculio* spp. (weevils), *Cyclocephala* spp. (grubs), *Cylindrocpturus adspersus* (sunflower stem weevil), *Deporaus marginatus* (mango leaf-cutting weevil), *Dermestes lardarius* (larder beetle), *Dermestes maculates* (hide beetle), *Diabrotica* spp. (chrysolemids), *Epilachna varivestis* (Mexican bean beetle), *Faustinus cubae, Hylobius pales* (pales weevil), *Hypera* spp. (weevils), *Hypera postica* (alfalfa weevil), *Hyperdoes* spp. (*Hyperodes weevil*), *Hypothenemus hampei* (coffee berry beetle), *Ips* spp. (engravers), *Lasioderma serricorne* (cigarette beetle), *Leptinotarsa decemlineata* (Colorado potato beetle), *Liogenys fuscus, Liogenys suturalis, Lissorhoptrus oryzophilus* (rice water weevil), *Lyctus* spp. (wood beetles/powder post beetles), *Maecolaspis joliveti, Megascelis* spp., *Melanotus communis, Meligethes* spp., *Meligethes aeneus* (blossom beetle), *Melolontha melolontha* (common European cockchafer), *Oberea brevis, Oberea linearis, Oryctes rhinoceros* (date palm beetle), *Oryzaephilus mercator* (merchant grain beetle), *Oryzaephilus surinamensis* (sawtoothed grain beetle), *Otiorhynchus* spp. (weevils), *Oulema melanopus* (cereal leaf beetle), *Oulema oryzae, Pantomorus* spp. (weevils), *Phyllophaga* spp. (May/June beetle), *Phyllophaga cuyabana, Phyllotreta* spp. (chrysomelids), *Phynchites* spp., *Popillia japonica* (Japanese beetle), *Prostephanus truncates* (larger grain borer), *Rhizopertha dominica* (lesser grain borer), *Rhizotrogus* spp. (Europoean chafer), *Rhynchophorus* spp. (weevils), *Scolytus* spp. (wood beetles), *Shenophorus* spp. (Billbug), *Sitona lineatus* (pea leaf weevil), *Sitophilus* spp. (grain weevils), *Sitophilus granaries* (granary weevil), *Sitophilus oryzae* (rice weevil), *Stegobium paniceum* (drugstore beetle), *Tribolium* spp. (flour beetles), *Tribolium castaneum* (red flour beetle), *Tribolium confusum* (confused flour beetle), *Trogoderma variabile* (warehouse beetle), and *Zabrus tenebioides.*

In another embodiment, the invention disclosed in this document can be used to control Dermaptera (earwigs).

In another embodiment, the invention disclosed in this document can be used to control Dictyoptera (cockroaches). A non-exhaustive list of these pests includes, but is not limited to, *Blattella germanica* (German cockroach), *Blatta orientalis* (oriental cockroach), *Parcoblatta pennylvanica, Periplaneta americana* (American cockroach), *Periplaneta australoasiae* (Australian cockroach), *Periplaneta brunnea* (brown cockroach), *Periplaneta fuliginosa* (smokybrown cockroach), *Pyncoselus suninamensis* (Surinam cockroach), and *Supella longipalpa* (brownbanded cockroach).

In another embodiment, the invention disclosed in this document can be used to control Diptera (true flies). A non-exhaustive list of these pests includes, but is not limited to, *Aedes* spp. (mosquitoes), *Agromyza frontella* (alfalfa blotch leafminer), *Agromyza* spp. (leaf miner flies), *Anastrepha* spp. (fruit flies), *Anastrepha suspensa* (Caribbean fruit fly), *Anopheles* spp. (mosquitoes), *Batrocera* spp. (fruit flies), *Bactrocera cucurbitae* (melon fly), *Bactrocera dorsalis* (oriental fruit fly), *Ceratitis* spp. (fruit flies), *Ceratitis capitata* (Mediterranea fruit fly), *Chrysops* spp. (deer flies), *Cochliomyia* spp. (screwworms), *Contarinia* spp. (Gall midges), *Culex* spp. (mosquitoes), *Dasineura* spp. (gall midges), *Dasineura brassicae* (cabbage gall midge), *Delia* spp., *Delia platura* (seedcorn maggot), *Drosophila* spp. (vinegar flies), *Fannia* spp. (filth flies), *Fannia canicularis* (little house fly), *Fannia scalaris* (latrine fly), *Gasterophilus intestinalis* (horse bot fly), *Gracillia perseae, Haematobia irritans* (horn fly), *Hylemyia* spp. (root maggots), *Hypoderma lineatum* (common cattle grub), *Liriomyza* spp. (leafminer flies), *Liriomyza brassica* (serpentine leafminer), *Melophagus ovi-*

*nus* (sheep ked), *Musca* spp. (muscid flies), *Musca autumnalis* (face fly), *Musca domestica* (house fly), *Oestrus ovis* (sheep bot fly), *Oscinella frit* (frit fly), *Pegomyia betae* (beet leafminer), *Phorbia* spp., *Psila rosae* (carrot rust fly), *Rhagoletis cerasi* (cherry fruit fly), *Rhagoletis pomonella* (apple maggot), *Sitodiplosis mosellana* (orange wheat blossom midge), *Stomoxys calcitrans* (stable fly), *Tabanus* spp. (horse flies), and *Tipula* spp. (crane flies).

In another embodiment, the invention disclosed in this document can be used to control Hemiptera (true bugs). A non-exhaustive list of these pests includes, but is not limited to, *Acrosternum hilare* (green stink bug), *Blissus leucopterus* (chinch bug), *Calocoris norvegicus* (potato mirid), *Cimex hemipterus* (tropical bed bug), *Cimex lectularius* (bed bug), *Dagbertus fasciatus, Dichelops furcatus, Dysdercus suturellus* (cotton stainer), *Edessa meditabunda, Eurygaster maura* (cereal bug), *Euschistus heros, Euschistus servus* (brown stink bug), *Helopeltis antonii, Helopeltis theivora* (tea blight plantbug), *Lagynotomus* spp. (stink bugs), *Leptocorisa oratorius, Leptocorisa varicornis, Lygus* spp. (plant bugs), *Lygus hesperus* (western tarnished plant bug), *Maconellicoccus hirsutus, Neurocolpus longirostris, Nezara viridula* (southern green stink bug), *Phytocoris* spp. (plant bugs), *Phytocoris californicus, Phytocoris relativus, Piezodorus guildingi, Poecilocapsus lineatus* (fourlined plant bug), *Psallus vaccinicola, Pseudacysta perseae, Scaptocoris castanea*, and *Triatoma* spp. (bloodsucking conenose bugs/kissing bugs).

In another embodiment, the invention disclosed in this document can be used to control Homoptera (aphids, scales, whiteflies, leafhoppers). A non-exhaustive list of these pests includes, but is not limited to, *Acrythosiphon pisum* (pea aphid), *Adelges* spp. (adelgids), *Aleurodes proletella* (cabbage whitefly), *Aleurodicus disperses, Aleurothrixus floccosus* (woolly whitefly), *Aluacaspis* spp., *Amrasca bigutella bigutella, Aphrophora* spp. (leafhoppers), *Aonidiella aurantii* (California red scale), *Aphis* spp. (aphids), *Aphis gossypii* (cotton aphid), *Aphis pomi* (apple aphid), *Aulacorthum solani* (foxglove aphid), *Bemisia* spp. (whiteflies), *Bemisia argentifolii, Bemisia tabaci* (sweetpotato whitefly), *Brachycolus noxius* (Russian aphid), *Brachycorynella asparagi* (asparagus aphid), *Brevennia rehi, Brevicoryne brassicae* (cabbage aphid), *Ceroplastes* spp. (scales), *Ceroplastes rubens* (red wax scale), *Chionaspis* spp. (scales), *Chrysomphalus* spp. (scales), *Coccus* spp. (scales), *Dysaphis plantaginea* (rosy apple aphid), *Empoasca* spp. (leafhoppers), *Eriosoma lanigerum* (woolly apple aphid), *Icerya purchasi* (cottony cushion scale), *Idioscopus nitidulus* (mango leafhopper), *Laodelphax striatellus* (smaller brown planthopper), *Lepidosaphes* spp., *Macrosiphum* spp., *Macrosiphum euphorbiae* (potato aphid), *Macrosiphum granarium* (English grain aphid), *Macrosiphum rosae* (rose aphid), *Macrosteles quadrilineatus* (aster leafhopper), *Mahanarva frimbiolata, Metopolophium dirhodum* (rose grain aphid), *Mictis longicornis, Myzus persicae* (green peach aphid), *Nephotettix* spp. (leafhoppers), *Nephotettix cinctipes* (green leafhopper), *Nilaparvata lugens* (brown planthopper), *Parlatoria pergandii* (chaff scale), *Parlatoria ziziphi* (ebony scale), *Peregrinus maidis* (corn delphacid), *Philaenus* spp. (spittlebugs), *Phylloxera vitifoliae* (grape phylloxera), *Physokermes piceae* (spruce bud scale), *Planococcus* spp. (mealybugs), *Pseudococcus* spp. (mealybugs), *Pseudococcus brevipes* (pine apple mealybug), *Quadraspidiotus perniciosus* (San Jose scale), *Rhapalosiphum* spp. (aphids), *Rhapalosiphum maida* (corn leaf aphid), *Rhapalosiphum padi* (oat bird-cherry aphid), *Saissetia* spp. (scales), *Saissetia oleae* (black scale), *Schizaphis graminum* (greenbug), *Sitobion avenae* (English grain aphid), *Sogatella furcifera* (white-backed planthopper), *Therioaphis* spp. (aphids), *Toumeyella* spp. (scales), *Toxoptera* spp. (aphids), *Trialeurodes* spp. (whiteflies), *Trialeurodes vaporariorum* (greenhouse whitefly), *Trialeurodes abutiloneus* (bandedwing whitefly), *Unaspis* spp. (scales), *Unaspis yanonensis* (arrowhead scale), and *Zulia entreriana*.

In another embodiment, the invention disclosed in this document can be used to control Hymenoptera (ants, wasps, and bees). A non-exhaustive list of these pests includes, but is not limited to, *Acromyrrmex* spp., *Athalia rosae, Atta* spp. (leafcutting ants), *Camponotus* spp. (carpenter ants), *Diprion* spp. (sawflies), *Formica* spp. (ants), *Iridomyrmex humilis* (Argentine ant), *Monomorium* ssp., *Monomorium minumum* (little black ant), *Monomorium pharaonis* (Pharaoh ant), *Neodiprion* spp. (sawflies), *Pogonomyrmex* spp. (harvester ants), *Polistes* spp. (paper wasps), *Solenopsis* spp. (fire ants), *Tapoinoma sessile* (odorous house ant), *Tetranomorium* spp. (pavement ants), *Vespula* spp. (yellow jackets), and *Xylocopa* spp. (carpenter bees).

In another embodiment, the invention disclosed in this document can be used to control Isoptera (termites). A non-exhaustive list of these pests includes, but is not limited to, *Coptotermes* spp., *Coptotermes curvignathus, Coptotermes frenchii, Coptotermes formosanus* (Formosan subterranean termite), *Cornitermes* spp. (nasute termites), *Cryptotermes* spp. (drywood termites), *Heterotermes* spp. (desert subterranean termites), *Heterotermes aureus, Kalotermes* spp. (drywood termites), *Incistitermes* spp. (drywood termites), *Macrotermes* spp. (fungus growing termites), *Marginitermes* spp. (drywood termites), *Microcerotermes* spp. (harvester termites), *Microtermes obesi, Procornitermes* spp., *Reticulitermes* spp. (subterranean termites), *Reticulitermes banyulensis, Reticulitermes grassei, Reticulitermes flavipes* (eastern subterranean termite), *Reticulitermes hageni, Reticulitermes hesperus* (western subterranean termite), *Reticulitermes santonensis, Reticulitermes speratus, Reticulitermes tibialis, Reticulitermes virginicus, Schedorhinotermes* spp., and *Zootermopsis* spp. (rotten-wood termites).

In another embodiment, the invention disclosed in this document can be used to control Lepidoptera (moths and butterflies). A non-exhaustive list of these pests includes, but is not limited to, *Achoea janata, Adoxophyes* spp., *Adoxophyes orana, Agrotis* spp. (cutworms), *Agrotis ipsilon* (black cutworm), *Alabama argillacea* (cotton leafworm), *Amorbia cuneana, Amyelosis transitella* (navel orangeworm), *Anacamptodes defectaria, Anarsia lineatella* (peach twig borer), *Anomis sabulifera* (jute looper), *Anticarsia gemmatalis* (velvetbean caterpillar), *Archips argyrospila* (fruittree leafroller), *Archips rosana* (rose leaf roller), *Argyrotaenia* spp. (tortricid moths), *Argyrotaenia citrana* (orange tortrix), *Autographa gamma, Bonagota cranaodes, Borbo cinnara* (rice leaf folder), *Bucculatrix thurberiella* (cotton leafperforator), *Caloptilia* spp. (leaf miners), *Capua reticulana, Carposina niponensis* (peach fruit moth), *Chilo* spp., *Chlumetia transversa* (mango shoot borer), *Choristoneura rosaceana* (obliquebanded leafroller), *Chrysodeixis* spp., *Cnaphalocerus medinalis* (grass leafroller), *Colias* spp., *Conpomorpha cramerella, Cossus cossus* (carpenter moth), *Crambus* spp. (Sod webworms), *Cydia funebrana* (plum fruit moth), *Cydia molesta* (oriental fruit moth), *Cydia nignicana* (pea moth), *Cydia pomonella* (codling moth), *Darna diducta, Diaphania* spp. (stem borers), *Diatraea* spp. (stalk borers), *Diatraea saccharalis* (sugarcane borer), *Diatraea graniosella* (southwester corn borer), *Earias* spp. (bollworms), *Earias insulata* (Egyptian bollworm), *Earias vitella* (rough northern bollworm), *Ecdytopopha aurantianum, Elasmopalpus lignosellus* (lesser cornstalk borer), *Epiphysias postruttana* (light brown apple moth), *Ephestia* spp. (flour moths), *Ephestia*

*cautella* (almond moth), *Ephestia elutella* (tobbaco moth), *Ephestia kuehniella* (Mediterranean flour moth), *Epimeces* spp., *Epinotia aporema, Erionota thrax* (banana skipper), *Eupoecilia ambiguella* (grape berry moth), *Euxoa auxiliaris* (army cutworm), *Feltia* spp. (cutworms), *Gortyna* spp. (stemborers), *Grapholita molesta* (oriental fruit moth), *Hedylepta indica* (bean leaf webber), *Helicoverpa* spp. (noctuid moths), *Helicoverpa armigera* (cotton bollworm), *Helicoverpa zea* (bollworm/corn earworm), *Heliothis* spp. (noctuid moths), *Heliothis virescens* (tobacco budworm), *Hellula undalis* (cabbage webworm), *Indarbela* spp. (root borers), *Keiferia lycopersicella* (tomato pinworm), *Leucinodes orbonalis* (eggplant fruit borer), *Leucoptera malifoliella, Lithocollectis* spp., *Lobesia botrana* (grape fruit moth), *Loxagrotis* spp. (noctuid moths), *Loxagrotis albicosta* (western bean cutworm), *Lymantria dispar* (gypsy moth), *Lyonetia clerkella* (apple leaf miner), *Mahasena corbetti* (oil palm bagworm), *Malacosoma* spp. (tent caterpillars), *Mamestra brassicae* (cabbage armyworm), *Maruca testulalis* (bean pod borer), *Metisa plana* (bagworm), *Mythimna unipuncta* (true armyworm), *Neoleucinodes elegantalis* (small tomato borer), *Nymphula depunctalis* (rice caseworm), *Operophthera brumata* (winter moth), *Ostrinia nubilalis* (European corn borer), *Oxydia vesulia, Pandemis cerasana* (common currant tortrix), *Pandemis heparana* (brown apple tortrix), *Papilio demodocus, Pectinophora gossypiella* (pink bollworm), *Peridroma* spp. (cutworms), *Peridroma saucia* (variegated cutworm), *Perileucoptera coffeella* (white coffee leafminer), *Phthorimaea operculella* (potato tuber moth), *Phyllocnisitis citrella, Phyllonorycter* spp. (leafminers), *Pieris rapae* (imported cabbageworm), *Plathypena scabra, Plodia interpunctella* (Indian meal moth), *Plutella xylostella* (diamondback moth), *Polychrosis viteana* (grape berry moth), *Prays endocarpa, Prays oleae* (olive moth), *Pseudaletia* spp. (noctuid moths), *Pseudaletia unipunctata* (armyworm), *Pseudoplusia includens* (soybean looper), *Rachiplusia nu, Scirpophaga incertulas, Sesamia* spp. (stemborers), *Sesamia inferens* (pink rice stem borer), *Sesamia nonagrioides, Setora nitens, Sitotroga cerealella* (Angoumois grain moth), *Sparganothis pilleriana, Spodoptera* spp. (armyworms), *Spodoptera exigua* (beet armyworm), *Spodoptera fugiperda* (fall armyworm), *Spodoptera oridania* (southern armyworm), *Synanthedon* spp. (root borers), *Thecla basilides, Thermisia gemmatalis, Tineola bisselliella* (webbing clothes moth), *Trichoplusia ni* (cabbage looper), *Tuta absoluta, Yponomeuta* spp., *Zeuzera coffeae* (red branch borer), and *Zeuzera pyrina* (leopard moth).

In another embodiment, the invention disclosed in this document can be used to control Mallophaga (chewing lice). A non-exhaustive list of these pests includes, but is not limited to, *Bovicola ovis* (sheep biting louse), *Menacanthus stramineus* (chicken body louse), and *Menopon gallinea* (common hen house).

In another embodiment, the invention disclosed in this document can be used to control Orthoptera (grasshoppers, locusts, and crickets). A non-exhaustive list of these pests includes, but is not limited to, *Anabrus simplex* (Mormon cricket), Gryllotalpidae (mole crickets), *Locusta migratoria, Melanoplus* spp. (grasshoppers), *Microcentrum retinerve* (angularwinged katydid), *Pterophylla* spp. (kaydids), *chistocerca gregaria, Scudderia furcata* (forktailed bush katydid), and *Valanga nigricorni.*

In another embodiment, the invention disclosed in this document can be used to control Phthiraptera (sucking lice). A non-exhaustive list of these pests includes, but is not limited to, *Haematopinus* spp. (cattle and hog lice), *Linognathus ovillus* (sheep louse), *Pediculus humanus capitis* (human body louse), *Pediculus humanus humanus* (human body lice), and *Pthirus pubis* (crab louse), In another embodiment, the invention disclosed in this document can be used to control Siphonaptera (fleas). A non-exhaustive list of these pests includes, but is not limited to, *Ctenocephalides canis* (dog flea), *Ctenocephalides felis* (cat flea), and *Pulex irritans* (human flea).

In another embodiment, the invention disclosed in this document can be used to control Thysanoptera (*thrips*). A non-exhaustive list of these pests includes, but is not limited to, *Frankliniella fusca* (tobacco *thrips*), *Frankliniella occidentalis* (western flower *thrips*), *Frankliniella shultzei Frankliniella williamsi* (corn *thrips*), *Heliothrips haemorrhaidalis* (greenhouse *thrips*), *Riphiphorothrips cruentatus, Scirtothrips* spp., *Scirtothrips citri* (citrus *thrips*), *Scirtothrips dorsalis* (yellow tea *thrips*), *Taeniothrips rhopalantennalis*, and *Thrips* spp.

In another embodiment, the invention disclosed in this document can be used to control Thysanura (bristletails). A non-exhaustive list of these pests includes, but is not limited to, *Lepisma* spp. (silverfish) and *Thermobia* spp. (firebrats).

In another embodiment, the invention disclosed in this document can be used to control Acarina (mites and ticks). A non-exhaustive list of these pests includes, but is not limited to, *Acarapsis woodi* (tracheal mite of honeybees), *Acarus* spp. (food mites), *Acarus siro* (grain mite), *Aceria mangiferae* (mango bud mite), *Aculops* spp., *Aculops lycopersici* (tomato russet mite), *Aculops pelekasi, Aculus pelekassi, Aculus schlechtendali* (apple rust mite), *Amblyomma americanum* (lone star tick), *Boophilus* spp. (ticks), *Brevipalpus obovatus* (privet mite), *Brevipalpus phoenicis* (red and black flat mite), *Demodex* spp. (mange mites), *Dermacentor* spp. (hard ticks), *Dermacentor variabilis* (american dog tick), *Dermatophagoides pteronyssinus* (house dust mite), *Eotetranycus* spp., *Eotetranychus carpini* (yellow spider mite), *Epitimerus* spp., *Eriophyes* spp., *Ixodes* spp. (ticks), *Metatetranycus* spp., *Notoedres cati, Oligonychus* spp., *Oligonychus coffee, Oligonychus ilicus* (southern red mite), *Panonychus* spp., *Panonychus citri* (citrus red mite), *Panonychus ulmi* (European red mite), *Phyllocoptruta oleivora* (citrus rust mite), *Polyphagotarsonemun latus* (broad mite), *Rhipicephalus sanguineus* (brown dog tick), *Rhizoglyphus* spp. (bulb mites), *Sarcoptes scabiei* (itch mite), *Tegolophus perseaflorae, Tetranychus* spp., *Tetranychus urticae* (twospotted spider mite), and *Varroa destructor* (honey bee mite).

In another embodiment, the invention disclosed in this document can be used to control Nematoda (nematodes). A non-exhaustive list of these pests includes, but is not limited to, *Aphelenchoides* spp. (bud and leaf & pine wood nematodes), *Belonolaimus* spp. (sting nematodes), *Criconemella* spp. (ring nematodes), *Dirofilaria immitis* (dog heartwom), *Ditylenchus* spp. (stem and bulb nematodes), *Heterodera* spp. (cyst nematodes), *Heterodera zeae* (corn cyst nematode), *Hirschmanniella* spp. (root nematodes), *Hoplolaimus* spp. (lance nematodes), *Meloidogyne* spp. (root knot nematodes), *Meloidogyne incognita* (root knot nematode), *Onchocerca volvulus* (hook-tail worm), *Pratylenchus* spp. (lesion nematodes), *Radopholus* spp. (burrowing nematodes), and *Rotylenchus reniformis* (kidney-shaped nematode).

In another embodiment, the invention disclosed in this document can be used to control Symphyla (symphylans). A non-exhaustive list of these pests includes, but is not limited to, *Scutigerella immaculata.*

For more detailed information consult "Handbook of Pest Control—The Behavior, Life History, and Control of Household Pests" by Arnold Mallis, $9^{th}$ Edition, copyright 2004 by GIE Media Inc.

Mixtures

Some of the pesticides that can be employed beneficially in combination with the invention disclosed in this document include, but are not limited to the following:

1,2 dichloropropane, 1,3 dichloropropene, abamectin, acephate, acequinocyl, acetamiprid, acethion, acetoprole, acrinathrin, acrylonitrile, alanycarb, aldicarb, aldoxycarb, aldrin, allethrin, allosamidin, allyxycarb, alpha cypermethrin, alpha ecdysone, amidithion, amidoflumet, aminocarb, amiton, amitraz, anabasine, arsenous oxide, athidathion, azadirachtin, azamethiphos, azinphos ethyl, azinphos methyl, azobenzene, azocyclotin, azothoate, barium hexafluorosilicate, barthrin, benclothiaz, bendiocarb, benfuracarb, benomyl, benoxafos, bensultap, benzoximate, benzyl benzoate, beta cyfluthrin, beta cypermethrin, bifenazate, bifenthrin, binapacryl, bioallethrin, bioethanomethrin, biopermethrin, bistrifluron, borax, boric acid, bromfenvinfos, bromo DDT, bromocyclen, bromophos, bromophos ethyl, bromopropylate, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, chinomethionat, chlorantraniliprole, chlorbenside, chlorbicyclen, chlordane, chlordecone, chlordimeform, chlorethoxyfos, chlorfenapyr, chlorfenethol, chlorfenson, chlorfensulphide, chlorfenvinphos, chlorfluazuron, chlormephos, chlorobenzilate, chloroform, chloromebuform, chloromethiuron, chloropicrin, chloropropylate, chlorphoxim, chlorprazophos, chlorpyrifos, chlorpyrifos methyl, chlorthiophos, chromafenozide, cinerin I, cinerin II, cismethrin, cloethocarb, clofentezine, closantel, clothianidin, copper acetoarsenite, copper arsenate, copper naphthenate, copper oleate, coumaphos, coumithoate, crotamiton, crotoxyphos, cruentaren A &B, crufomate, cryolite, cyanofenphos, cyanophos, cyanthoate, cyclethrin, cycloprothrin, cyenopyrafen, cyflumetofen, cyfluthrin, cyhalothrin, cyhexatin, cypermethrin, cyphenothrin, cyromazine, cythioate, d-limonene, dazomet, DBCP, DCIP, DDT, decarbofuran, deltamethrin, demephion, demephion O, demephion S, demeton, demeton methyl, demeton O, demeton O methyl, demeton S, demeton S methyl, demeton S methylsulphon, diafenthiuron, dialifos, diamidafos, diazinon, dicapthon, dichlofenthion, dichlofluanid, dichlorvos, dicofol, dicresyl, dicrotophos, dicyclanil, dieldrin, dienochlor, diflovidazin, diflubenzuron, dilor, dimefluthrin, dimefox, dimetan, dimethoate, dimethrin, dimethylvinphos, dimetilan, dinex, dinobuton, dinocap, dinocap 4, dinocap 6, dinocton, dinopenton, dinoprop, dinosam, dinosulfon, dinotefuran, dinoterbon, diofenolan, dioxabenzofos, dioxacarb, dioxathion, diphenyl sulfone, disulfuram, disulfoton, dithicrofos, DNOC, dofenapyn, doramectin, ecdysterone, emamectin, EMPC, empenthrin, endosulfan, endothion, endrin, EPN, epofenonane, eprinomectin, esfenvalerate, etaphos, ethiofencarb, ethion, ethiprole, ethoate methyl, ethoprophos, ethyl DDD, ethyl formate, ethylene dibromide, ethylene dichloride, ethylene oxide, etofenprox, etoxazole, etrimfos, EXD, famphur, fenamiphos, fenazaflor, fenazaquin, fenbutatin oxide, fenchlorphos, fenethacarb, fenfluthrin, fenitrothion, fenobucarb, fenothiocarb, fenoxacrim, fenoxycarb, fenpirithrin, fenpropathrin, fenpyroximate, fenson, fensulfothion, fenthion, fenthion ethyl, fentrifanil, fenvalerate, fipronil, flonicamid, fluacrypyrim, fluazuron, flubendiamide, flubenzimine, flucofuron, flucycloxuron, flucythrinate, fluenetil, flufenerim, flufenoxuron, flufenprox, flumethrin, fluorbenside, fluvalinate, fonofos, formetanate, formothion, formparanate, fosmethilan, fospirate, fosthiazate, fosthietan, fosthietan, furathiocarb, furethrin, furfural, gamma cyhalothrin, gamma HCH, halfenprox, halofenozide, HCH, HEOD, heptachlor, heptenophos, heterophos, hexaflumuron, hexythiazox, HHDN, hydramethylnon, hydrogen cyanide, hydroprene, hyquincarb, imicyafos, imidacloprid, imiprothrin, indoxacarb, iodomethane, IPSP, isamidofos, isazofos, isobenzan, isocarbophos, isodrin, isofenphos, isoprocarb, isoprothiolane, isothioate, isoxathion, ivermectin jasmolin I, jasmolin II, jodfenphos, juvenile hormone I, juvenile hormone II, juvenile hormone III, kelevan, kinoprene, lambda cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfen, mesulfenfos, metaflumizone, metam, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, MNAF, monocrotophos, morphothion, moxidectin, naftalofos, naled, naphthalene, nicotine, nifluridide, nikkomycins, nitenpyram, nithiazine, nitrilacarb, novaluron, noviflumuron, omethoate, oxamyl, oxydemeton methyl, oxydeprofos, oxydisulfoton, paradichlorobenzene, parathion, parathion methyl, penfluoron, pentachlorophenol, permethrin, phenkapton, phenothrin, phenthoate, phorate, phosalone, phosfolan, phosmet, phosnichlor, phosphamidon, phosphine, phosphocarb, phoxim, phoxim methyl, pirimetaphos, pirimicarb, pirimiphos ethyl, pirimiphos methyl, potassium arsenite, potassium thiocyanate, pp' DDT, prallethrin, precocene I, precocene II, precocene III, primidophos, proclonol, profenofos, profluthrin, promacyl, promecarb, propaphos, propargite, propetamphos, propoxur, prothidathion, prothiofos, prothoate, protrifenbute, pyraclofos, pyraflumitrole, pyrazophos, pyresmethrin, pyrethrin I, pyrethrin II, pyridaben, pyridalyl, pyridaphenthion, pyrifluquinazon, pyrimidifen, pyrimitate, pyriprole, pyriproxyfen, quassia, quinalphos, quinalphos, quinalphos methyl, quinothion, quantifies, rafoxanide, resmethrin, rotenone, ryania, sabadilla, schradan, selamectin, silafluofen, sodium arsenite, sodium fluoride, sodium hexafluorosilicate, sodium thiocyanate, sophamide, spinetoram, spinosad, spirodiclofen, spiromesifen, spirotetramat, sulcofuron, sulfuram, sulfluramid, sulfotep, sulfur, sulfuryl fluoride, sulprofos, tau fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetradifon, tetramethrin, tetranactin, tetrasul, theta cypermethrin, thiacloprid, thiamethoxam, thicrofos, thiocarboxime, thiocyclam, thiodicarb, thiofanox, thiometon, thionazin, thioquinox, thiosultap, thuringiensin, tolfenpyrad, tralomethrin, transfluthrin, transpermethrin, triarathene, triazamate, triazophos, trichlorfon, trichlormetaphos 3, trichloronat, trifenofos, triflumuron, trimethacarb, triprene, vamidonothion, vamidothion, vaniliprole, vaniliprole, XMC, xylylcarb, zeta cypermethrin and zolaprofos.

Additionally, any combination of the above pesticides can be used.

The invention disclosed in this document can also be used with herbicides and fungicides, both for reasons of economy and synergy.

The invention disclosed in this document can be used with antimicrobials, bactericides, defoliants, safeners, synergists, algaecides, attractants, desiccants, pheromones, repellants, animal dips, avicides, disinfectants, semiochemicals, and molluscicides (these categories not necessarily mutually exclusive) for reasons of economy, and synergy.

For more information consult "Compendium of Pesticide Common Names" located at http://www.alanwood.net/pesticides/index.html as of the filing date of this document. Also consult "The Pesticide Manual" 14$^{th}$ Edition, edited by C D S Tomlin, copyright 2006 by British Crop Production Council.

Synergistic Mixtures

The invention disclosed in this document can be used with other compounds such as the ones mentioned under the heading "Mixtures" to form synergistic mixtures where the mode of action of the compounds in the mixtures are the same, similar, or different.

Examples of mode of actions include, but are not limited to: acetyl choline esterase inhibitor; sodium channel modulator; chitin biosynthesis inhibitor; GABA-gated chloride channel antagonist; GABA and glutamate-gated chloride channel agonist; acetyl choline receptor agonist; MET I inhibitor; Mg-stimulated ATPase inhibitor; nicotinic acetylcholine receptor; Midgut membrane disrupter; and oxidative phosphorylation disrupter.

Additionally, the following compounds are known as synergists and can be used with the invention disclosed in this document: piperonyl butoxide, piprotal, propyl isome, sesamex, sesamolin, and sulfoxide.

Formulations

A pesticide is rarely suitable for application in its pure form. It is usually necessary to add other substances so that the pesticide can be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra low volume solutions.

For further information on formulation types see "Catalogue of pesticide formulation types and international coding system" Technical Monograph n° 2, 5$^{th}$ Edition by CropLife International (2002).

Pesticides are applied most often as aqueous suspensions or emulsions prepared from concentrated formulations of such pesticides. Such water-soluble, water-suspendable, or emulsifiable formulations, are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually chosen from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and nonionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional anionic and nonionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums, may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to 3 mm. Such compositions may also be formulated by making a dough or paste of the carrier and compound and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. They can be applied as a seed dressing, or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. They are use in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings or in special chambers.

Pesticides can be microencapsulated by suspending the pesticide particles or droplets in plastic polymers of various types. By altering the chemistry of the polymer or by changing factors in the processing, microcapsules can be formed of various sizes, solubility, wall thicknesses, and degrees of penetrability. These factors govern the speed with which the active ingredient within is released, which. in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer comprising: (1) at least one non-ionic lipophilic surface-active agent, (2) at least one non-ionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007, having patent application Ser. No. 11/495,228. For ease of use this embodiment will be referred to as "OIWE".

For further information consult "Insect Pest Management" $2^{nd}$ Edition by D. Dent, copyright CAB International (2000). Additionally, for more detailed information consult "Handbook of Pest Control—The Behavior, Life History, and Control of Household Pests" by Arnold Mallis, $9^{th}$ Edition, copyright 2004 by GIE Media Inc.

Other Formulation Components

Generally, the invention disclosed in this document when used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, antifoam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulphate; sodium dioctyl sulphosuccinate; alkyl phenol ethoxylates; and aliphatic alcohol ethoxylates.

A dispersing agent is a substance which adsorbs onto the surface of a particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulphonates. For suspension concentrates, very good adsorption and stabilization are obtained using polyelectrolytes, such as sodium naphthalene sulphonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates, In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulphonates; sodium naphthalene sulphonate formaldehyde condensates; tristyrylphenol ethoxylate phosphate esters; aliphatic alcohol ethoxylates; alky ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with 12 or more ethylene oxide units and the oil-soluble calcium salt of dodecylbenzene sulphonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilized water-insoluble materials inside the hydrophobic part of the micelle. The type of surfactants usually used for solubilization are non-ionics: sorbitan monooleates; sorbitan monooleate ethoxylates; and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alky ethoxylates; linear aliphatic alcohol ethoxylates; aliphatic amine ethoxylates.

A carrier or diluent in an agricultural formulation is a material added to the pesticide to give a product of the required strength. Carriers arc usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, ULV formulations, and to a lesser extent granular formulations. Sometimes mixtures of solvents are used. The first main groups of solvents are aliphatic paraffinic oils such as kerosene or refined paraffins. The second main group and the most common comprises the aromatic solvents such as xylene and higher molecular weight fractions of $C_9$ and $C_{10}$ aromatic solvents. Chlorinated hydrocarbons are useful as cosolvents to prevent crystallization of pesticides when the formulation is emulsified into water. Alcohols are sometimes used as cosolvents to increase solvent power.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are limited to, montmorillonite, e.g. bentonite; magnesium aluminum silicate; and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms which cause spoilage of formulated products. Therefore preservation agents are used to eliminate or reduce their effect. Examples of such agents include, but are limited to propionic acid and its sodium salt; sorbic acid and its sodium or potassium salts; benzoic acid and its sodium salt; p-hydroxy benzoic acid sodium salt; methyl p-hydroxy benzoate; and 1,2-benzisothiazalin-3-one (BIT).

The presence of surfactants, which lower interfacial tension, often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane while the non-silicone anti-foam agents are water-insoluble oils, such as octanol and nonanol, or silica. In both cases, the function of the anti-foam agent is to displace the surfactant from the air-water interface.

For further information see "Chemistry and Technology of Agrochemical Formulations" edited by D. A. Knowles, copyright 1998 by Kluwer Academic Publishers. Also see "Insecticides in Agriculture and Environment—Retrospects and Prospects" by A. S. Perry, I. Yamamoto, I. Ishaaya, and R. Perry, copyright 1998 by Springer-Verlag.

APPLICATIONS

The actual amount of pesticide to be applied to loci of pests is generally not critical and can readily be determined by those skilled in the art. In general, concentrations from about 0.01 grams of pesticide per hectare to about 5000 grams of pesticide per hectare are expected to provide good control.

The locus to which a pesticide is applied can be any locus inhabited by an pest, for example, vegetable crops, fruit and nut trees, grape vines, ornamental plants, domesticated animals, the interior or exterior surfaces of buildings, and the soil around buildings. Controlling pests generally means that pest populations, activity, or both, are reduced in a locus. This can come about when: pest populations are repulsed from a locus; when pests are incapacitated, partially or completely, temporarily or permanently, in or around a locus; or pests are exterminated, in whole or in part, in or around a locus. Of course a combination of these results can occur. Generally, pest populations, activity, or both are desirably reduce more than fifty percent, preferably more than 90 percent, even more preferably 99 percent.

Generally, with baits, the baits are placed in the ground where, for example, termites can come into contact with the bait. Baits can also be applied to a surface of a building, (horizontal, vertical, or slant, surface) where, for example, ants, termites, cockroaches, and flies, can come into contact with the bait.

Because of the unique ability of the eggs of some pests to resist pesticides repeated applications may be desirable to control newly emerged larvae.

Systemic movement of pesticides in plants may be utilized to control pests on one portion of the plant by applying the pesticides to a different portion of the plant, or to a location where the root system of a plant can uptake pesticides. For example, control of foliar-feeding insects can be controlled by drip irrigation or furrow application, or by treating the seed before planting. Seed treatment can be applied to all types of seeds, including those from which plants genetically transformed to express specialized traits will germinate. Representative examples include those expressing proteins toxic to invertebrate pests, such as *Bacillus thuringiensis* or other insecticidal toxins, those expressing herbicide resistance, such as "Roundup Ready" seed, or those with "stacked" foreign genes expressing insecticidal toxins, herbicide resistance, nutrition-enhancement or any other beneficial traits. Furthermore, such seed treatments with the invention disclosed in this document can further enhance the ability of a plant to better withstand stressful growing conditions. This results in a healthier, more vigorous plant, which can lead to higher yields at harvest time.

It should be readily apparent that the invention can be used with plants genetically transformed to express specialized traits, such as *Bacillus thuringiensis* or other insecticidal toxins, or those expressing herbicide resistance, or those with "stacked" foreign genes expressing insecticidal toxins, herbicide resistance, nutrition-enhancement or any other beneficial traits. An example of such a use is spraying such plants with the invention disclosed in this document.

The invention disclosed in this document is suitable for controlling endoparasites and ectoparasites in the veterinary medicine sector or in the field of animal keeping. Compounds according to the invention are applied here in a known manner, such as by oral administration in the form of, for example, tablets, capsules, drinks, granules, by dermal application in the form of, for example, dipping, spraying, pouring on, spotting on, and dusting, and by parenteral administration in the form of, for example, an injection.

The invention disclosed in this document can also be employed advantageously in livestock keeping, for example, cattle, sheep, pigs, chickens, and geese. Suitable formulations are administered orally to the animals with the drinking water or feed. The dosages and formulations that are suitable depend on the species.

Before a pesticide can be used or sold commercially, such pesticide undergoes lengthy evaluation processes by various governmental authorities (local, regional, state, national, international). Voluminous data requirements are specified by regulatory authorities and must be addressed through data generation and submission by the product registrant or by another on the product registrant's behalf. These governmental authorities then review such data and if a determination of safety is concluded, provide the potential user or seller with product registration approval. Thereafter, in that locality where the product registration is granted and supported, such user or seller may use or sell such pesticide.

The headings in this document are for convenience only and must not be used to interpret any portion thereof.

What is claimed is:

1. A process of controlling pests, said process comprising applying a composition comprising a compound having the following formula

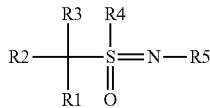

wherein
R1 is a substituted heterocyclyl, wherein the substituted heterocyclyl has one or more substituents independently selected from halo and haloalkyl;
R2 is alkyl;
R3 is hydrogen;
R4 is alkyl;
R5 is an unsubstituted heterocyclyl or a substituted heterocyclyl, wherein the substituted heterocyclyl has one or more substituents selected independently from alkenyl, alkenyloxy, alkoxy, alkyl, alkynyl, alkynyloxy, aryl, cycloalkenyl, cycloalkenyloxy, cycloalkyl, cycloalkoxy, halo, haloalkyl, heterocyclyl, —O⁻, CN, C1-C6 alkyl-O—C(=O)—, C1-C6 alkyl-O—C1-C6 alkyl, C1-C6 alkylthio-C1-C6 alkyl, and NO2, optionally, the substituents (that can be further substituted) on a substituted heterocyclyl are also substituted with one or more substituents independently selected from alkenyl, alkenyloxy, alkoxy, alkyl, alkynyl, alkynyloxy, aryl, cycloalkenyl, cycloalkenyloxy, cycloalkyl, cycloalkoxy, halo, haloalkyl, heterocyclyl, CN, C1-C6 alkyl-O—C(=O)—, and NO2;
to an area where control of pests of Homoptera is desired.

2. A process according to claim 1 wherein said composition further comprises at least one other insecticide.

3. A process according to claim 1 wherein said composition further comprises at least one herbicide, at least one fungicide, or at least one herbicide and fungicide.

4. A process according to claim 1 wherein said composition further comprises at least one of the following items—antimicrobials, bactericides, defoliants, safeners, synergists, algaecides, attractants, desiccants, pheromones, repellants, avicides, disinfectants, semiochemicals, or molluscicides.

5. A process according to claim 1 wherein said composition further comprises at least one of the following items: acetyl choline esterase inhibitor; sodium channel modulator; chitin biosynthesis inhibitor; GABA-gated chloride channel antagonist; GABA and glutamate-gated chloride channel agonist; acetyl choline receptor agonist; MET I inhibitor; Mg-stimulated ATPase inhibitor; nicotinic acetylcholine receptor; Midgut membrane disrupter; or oxidative phosphorylation disrupter.

6. A process according to claim 1 wherein said composition further comprises at least one of the following—piperonyl butoxide, piprotal, propyl isome, sesamex, sesamolin, or sulfoxide.

7. A process according to claim 1 wherein said composition is in the form of bait, concentrated emulsion, dust, emulsifiable concentrate, fumigant, gel, granule, microencapsulation, seed treatment, suspension concentrate, suspoemulsion, tablet, water soluble liquid, water dispersible granule, wettable powder, or ultra low volume solution.

* * * * *